US 11,116,914 B2

(12) United States Patent
Shahaf et al.

(10) Patent No.: US 11,116,914 B2
(45) Date of Patent: Sep. 14, 2021

(54) DEVICE AND METHOD FOR AEROSOLIZED DELIVERING OF SUBSTANCE TO A NATURAL ORIFICE OF THE BODY

(71) Applicant: SIPNOSE LTD., Yokne'am Ilit (IL)

(72) Inventors: Daniel Shahaf, M.P. Emek Ha-Yarden (IL); Iris Shichor, Zichron Yaakov (IL); David Napchi, Savion (IL)

(73) Assignee: SIPNOSE LTD., Yokne'am Ilit (IL)

( * ) Notice: Subject to any disclaimer, the term of this patent is extended or adjusted under 35 U.S.C. 154(b) by 1446 days.

(21) Appl. No.: 14/733,143

(22) Filed: Jun. 8, 2015

(65) Prior Publication Data

US 2016/0129205 A1    May 12, 2016

Related U.S. Application Data

(60) Provisional application No. 62/077,246, filed on Nov. 9, 2014, provisional application No. 62/117,986, filed on Feb. 19, 2015.

(51) Int. Cl.
*A61M 11/02* (2006.01)
*A61M 15/08* (2006.01)
(Continued)

(52) U.S. Cl.
CPC .......... *A61M 11/02* (2013.01); *A61M 15/003* (2014.02); *A61M 15/0091* (2013.01);
(Continued)

(58) Field of Classification Search
CPC .. A61M 11/00; A61M 11/001; A61M 11/006; A61M 11/007; A61M 11/008;
(Continued)

(56) References Cited

U.S. PATENT DOCUMENTS 462,990 A    11/1891  Oppenheimer
3,921,637 A   11/1975  Bennie et al.
(Continued)

FOREIGN PATENT DOCUMENTS

DE    20 2013 105 715 U1    2/2014
EP        1 752 176 A1       2/2007
(Continued)

OTHER PUBLICATIONS

Damm et al., "Intranasal Volume and Olfactory Function", Chemical Senses, 2002, pp. 831-839, vol. 27, Oxford University Press.
(Continued)

*Primary Examiner* — Colin W Stuart
(74) *Attorney, Agent, or Firm* — Foley & Lardner LLP

(57) ABSTRACT

A device for delivering a predetermined volume a substance within a body cavity. The device includes: at least one predefined volume sized and shaped to contain a predetermined volume the substance; a delivery end in fluid communication with a container; and at least one valve mechanically connected to the container and configurable between an active configuration in which the valve enables delivery of a volume of the substance and an inactive configuration, in which the valve prevents delivery.

38 Claims, 54 Drawing Sheets

(51) Int. Cl.
*A61M 15/00* (2006.01)
*A61M 11/00* (2006.01)
*A61M 31/00* (2006.01)

(52) U.S. Cl.
CPC ............ *A61M 15/08* (2013.01); *A61M 11/001* (2014.02); *A61M 15/0003* (2014.02); *A61M 15/0061* (2014.02); *A61M 15/0065* (2013.01); *A61M 15/0093* (2014.02); *A61M 31/00* (2013.01); *A61M 2202/04* (2013.01); *A61M 2202/064* (2013.01); *A61M 2205/073* (2013.01); *A61M 2205/7509* (2013.01); *A61M 2205/7518* (2013.01); *A61M 2205/7545* (2013.01); *A61M 2206/16* (2013.01); *A61M 2209/02* (2013.01); *A61M 2210/065* (2013.01); *A61M 2210/0618* (2013.01); *A61M 2210/0625* (2013.01); *A61M 2210/0662* (2013.01); *A61M 2210/1089* (2013.01); *A61M 2210/1475* (2013.01)

(58) Field of Classification Search
CPC ...... A61M 11/02; A61M 11/06; A61M 15/00; A61M 15/0001; A61M 15/002; A61M 15/0028; A61M 15/003; A61M 15/0003; A61M 15/0031; A61M 15/0043; A61M 15/0061; A61M 15/0063; A61M 15/0091; A61M 15/0093; A61M 15/0095; A61M 15/08; A61M 31/00; A61M 2202/04; A61M 2202/064; A61M 2205/073; A61M 2206/16; A61M 2209/02; A61M 2210/0618; A61M 2210/0625; A61M 2210/065; A61M 2210/0662
See application file for complete search history.

(56) References Cited

U.S. PATENT DOCUMENTS

| | | | |
|---|---|---|---|
| 4,114,615 | A | 9/1978 | Wetterlin |
| 4,620,670 | A | 11/1986 | Hughes |
| 5,740,794 | A | 4/1998 | Smith et al. |
| 6,398,074 | B1 | 6/2002 | Bruna et al. |
| 7,497,390 | B2 | 3/2009 | Beller |
| 7,726,308 | B1 | 6/2010 | Flora |
| 7,802,569 | B2 | 9/2010 | Yeates et al. |
| 7,900,659 | B2 | 3/2011 | Whitley et al. |
| 2002/0023641 | A1 | 2/2002 | Stadelhofer |
| 2002/0092520 | A1 | 7/2002 | Casper et al. |
| 2003/0079743 | A1 | 5/2003 | Genova et al. |
| 2003/0187404 | A1 | 10/2003 | Waldenburg |
| 2005/0028812 | A1 | 2/2005 | Djupesland |
| 2006/0067911 | A1 | 3/2006 | Nilsson et al. |
| 2006/0107957 | A1* | 5/2006 | Djupesland ............ A61M 11/00 128/206.11 |
| 2006/0151629 | A1 | 7/2006 | Vedrine et al. |
| 2006/0213514 | A1* | 9/2006 | Price .................. A61M 15/0043 128/203.15 |
| 2007/0060868 | A1 | 3/2007 | Tsutsui |
| 2007/0125371 | A1* | 6/2007 | Djupesland ............ A61M 15/00 128/200.14 |
| 2007/0154407 | A1* | 7/2007 | Peters .................. A61K 9/0078 424/46 |
| 2008/0092887 | A1 | 4/2008 | Hodson et al. |
| 2009/0285849 | A1 | 11/2009 | Barsanti et al. |
| 2009/0314293 | A1* | 12/2009 | Djupesland ............ A61M 11/00 128/203.18 |
| 2010/0282246 | A1 | 11/2010 | Djupesland et al. |
| 2011/0048414 | A1 | 3/2011 | Hoekman et al. |
| 2011/0088690 | A1 | 4/2011 | Djupesland et al. |
| 2011/0168172 | A1 | 7/2011 | Patton et al. |
| 2011/0283996 | A1 | 11/2011 | Abrams |
| 2012/0291779 | A1* | 11/2012 | Haartsen ................. G01F 1/684 128/203.12 |
| 2013/0096495 | A1 | 4/2013 | Holmqvist et al. |
| 2013/0180524 | A1 | 7/2013 | Shahaf et al. |
| 2013/0267864 | A1* | 10/2013 | Addington ........... A61B 5/4839 600/538 |
| 2013/0299607 | A1* | 11/2013 | Wilkerson .......... B05B 17/0646 239/328 |
| 2014/0060532 | A1 | 3/2014 | Hodges et al. |
| 2015/0122257 | A1* | 5/2015 | Winkler ............ A61M 15/0035 128/203.15 |
| 2015/0144129 | A1 | 5/2015 | Djupesland et al. |
| 2015/0174343 | A1* | 6/2015 | Muellinger ............ A61M 11/06 128/200.16 |
| 2015/0209325 | A1 | 7/2015 | Najarian et al. |
| 2015/0297845 | A1 | 10/2015 | Shahaf et al. |
| 2016/0129205 | A1 | 5/2016 | Shahaf et al. |
| 2019/0015613 | A1 | 1/2019 | Shahaf et al. |
| 2020/0289768 | A1 | 9/2020 | Shahaf et al. |
| 2020/0306463 | A1 | 10/2020 | Shahaf et al. |

FOREIGN PATENT DOCUMENTS

| | | | |
|---|---|---|---|
| EP | 2 030 645 | A1 | 3/2009 |
| GB | 0 724 974 | A | 2/1955 |
| GB | 2 415 376 | A | 12/2005 |
| WO | WO-90/12567 | A1 | 11/1990 |
| WO | WO-2012/029064 | A1 | 3/2012 |
| WO | WO-2013128447 | A1 * | 9/2013 |
| WO | WO 2015/025324 | A1 | 2/2015 |
| WO | WO-2016/199135 | A1 | 12/2016 |
| WO | WO-2019/003216 | A1 | 1/2019 |
| WO | WO-2019/220443 | A1 | 11/2019 |

OTHER PUBLICATIONS

Derendorf et al., "Molecular and clinical pharmacology of intranasal corticosteroids: clinical and therapeutic implications", Allergy, 2008, pp. 1292-1300, vol. 63, 2008 Blackwell Munksgaard.
Doose et al., "Single-dose pharmacokinetics and effect of food on the bioavailability of topiramate, a novel antiepileptic drug", Journal of Clinical Pharmacology, 1996, pp. 884-891, vol. 36.
Ganger et al., "Tailoring Formulations for Intranasal Nose-to-Brain Delivery: A Review on Architecture, Physico-Chemical Characteristics and Mucociliary Clearance of the Nasal Olfactory Mucosa", Pharmaceutics, 2018, pp. 1-28, vol. 10, No. 116.
International Preliminary Report on Patentability for International Application No. PCT/IL2014/050752, dated Feb. 23, 2016.
International Search Report & International Written Opinion of the International Searching Authority issued in International Application No. PCT/IL2014/050752, dated Dec. 18, 2014.
Khan et al., "Progress in brain targeting drug delivery system by nasal route", Journal of Controlled Release, 2017, pp. 364-389, vol. 268, Elsevier B.V.
Lammi et al., "Treatment with intranasal iloprost reduces disease manifestations in a murine model of previously established COPD", The American Journal of Physiology—Lung Cellular and Molecular Physiology, 2016, pp. L630-L638, vol. 310, 2016 American Physiological Society.
Leombruni et al., "Treatment of obese patients with binge eating disorder using topiramate: a review", Neuropsychiatric Disease and Treatment, 2009, pp. 385-392, vol. 5, Dove Medical Press Ltd.
Massolt et al., "Appetite suppression through smelling of dark chocolate correlates with changes in ghrelin in young women", Regulatory Peptides, 2010, pp. 81-86, vol. 161, 2010 Elsevier B.V.
Puhakka et al., "The common cold: Effects of intranasal fluticasone propionate treatment", The Journal of Allergy and Clinical Immunology, 1998, pp. 726-731, vol. 101, No. 6, Part 1, Mosby, Inc.
Ramaekers et al., "Odors: appetizing or satiating? Development of appetite during odor exposure over time", International Journal of Obesity, 2014, pp. 650-656, vol. 38, 2014 Macmillan Publishers Limited.
Scheibe et al., "Intranasal Administration of Drugs", Archives of Otolaryngology—Head & Neck Surgery, Jun. 2008, pp. 643-646, vol. 134, No. 6, 2008 American Medical Association.

(56) References Cited

OTHER PUBLICATIONS

Schiffman et al., "Taste and smell perception affect appetite and immunity in the elderly", European Journal of Clinical Nutrition, 2000, pp. S54-S63, Suppl 3, 2000 Macmillan Publishers Ltd.

Schriever et al., "Size of nostril opening as a measure of intranasal volume", Physiology & Behavior, 2013, pp. 3-5, vol. 110-111, 2012 Elsevier Inc.

Yeomans, "Olfactory influences on appetite and satiety in humans", Physiology and Behavior, 2006, pp. 1-14, vol. 89, No. 1.

* cited by examiner

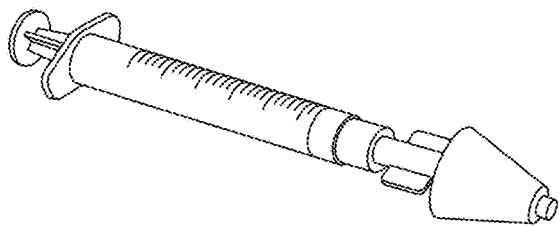
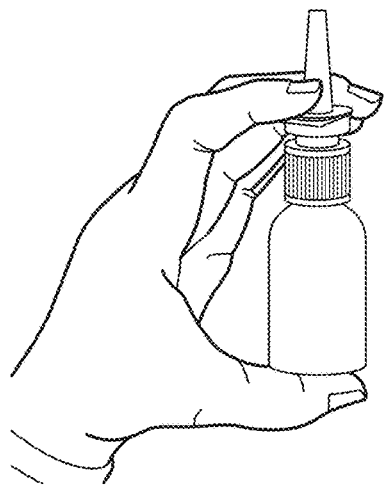
Prior Art
Fig. 1A
Prior Art
Fig. 1B
Prior Art
Fig. 1C
Prior Art
Fig. 1D

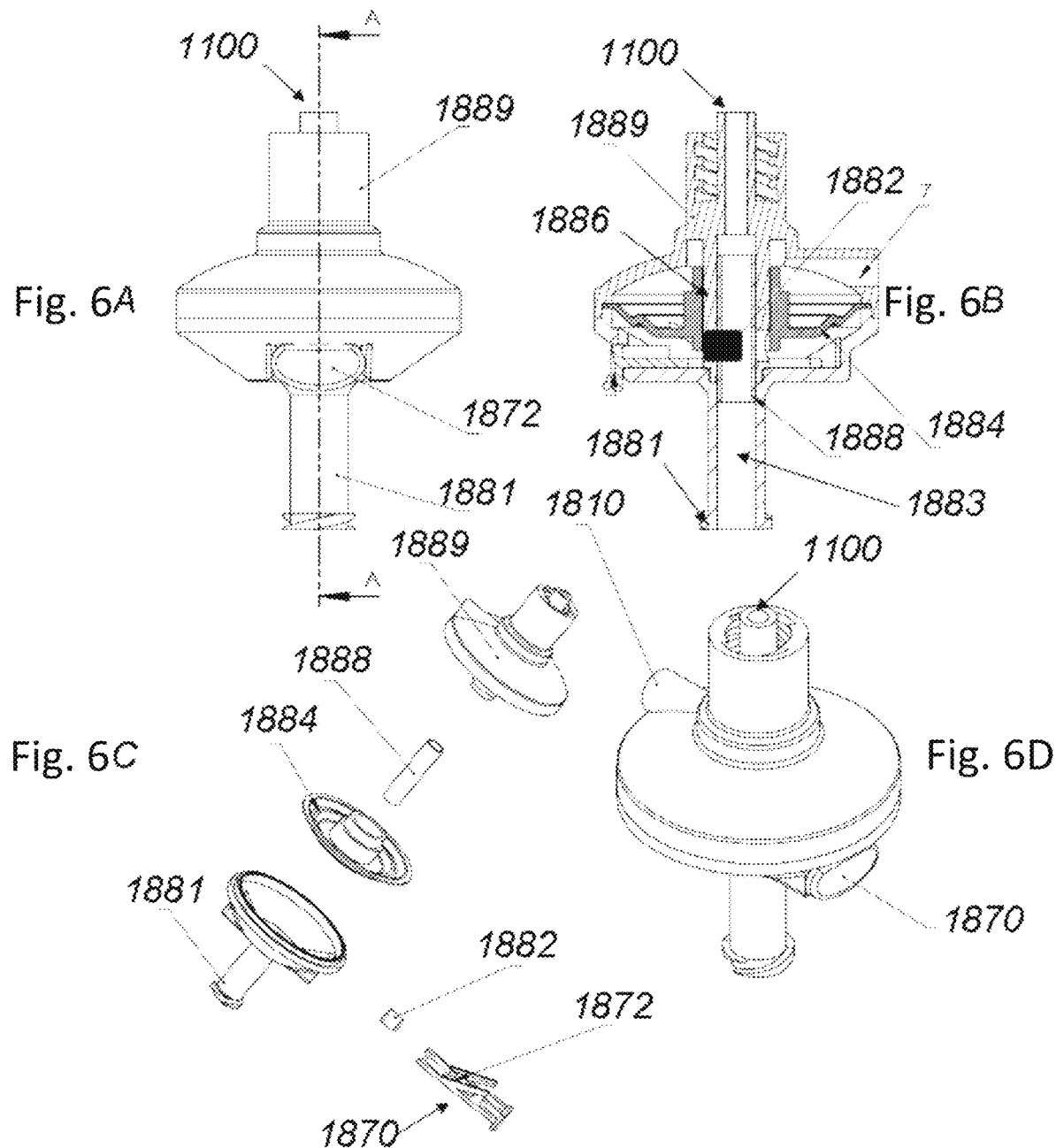

| Operating Conditions | Before Activation | After Activation |
|---|---|---|
| 1 | | |
| 2 | | |
| 3 | | |

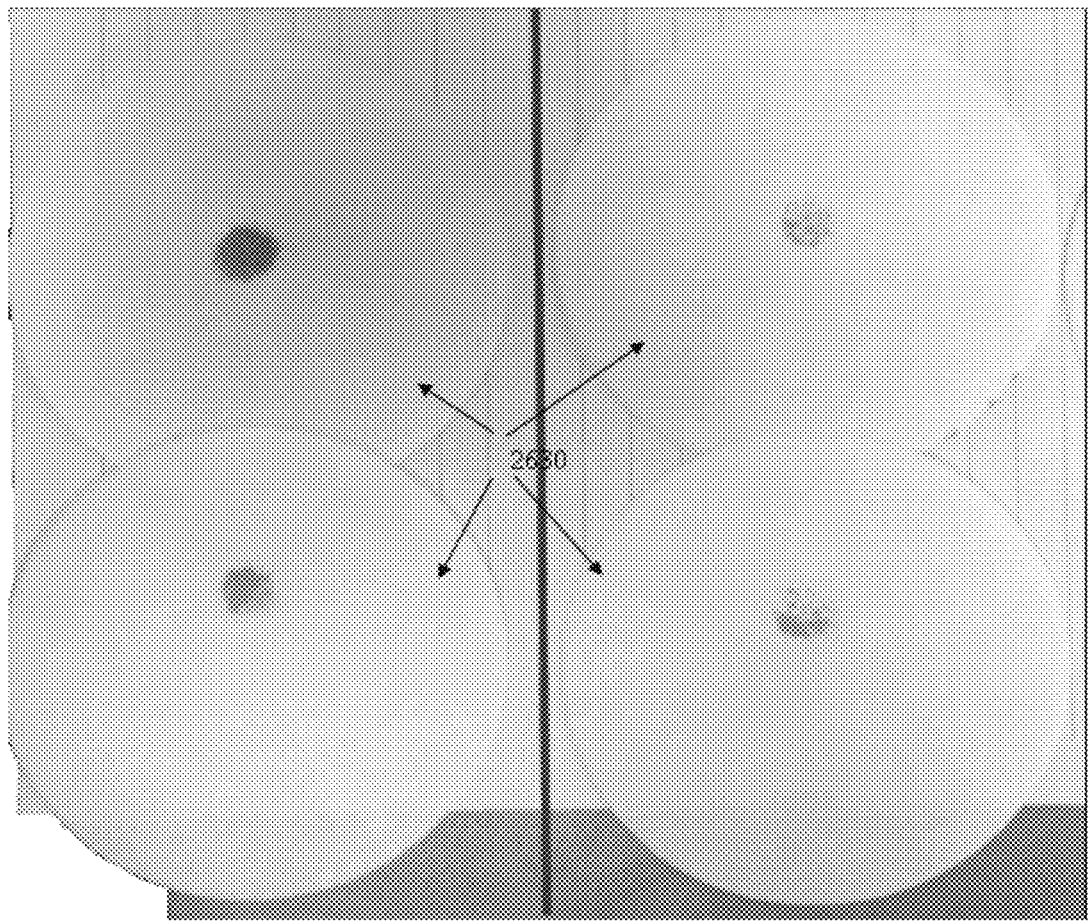
Fig. 13A          Fig. 13B
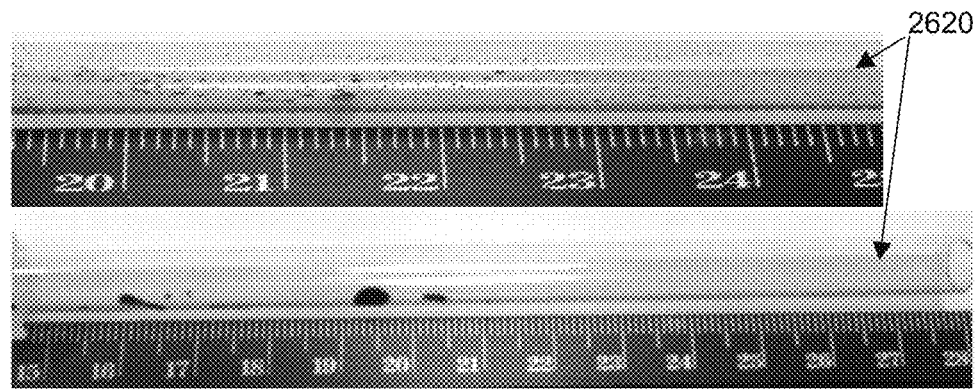
Fig. 14A
Fig. 14B

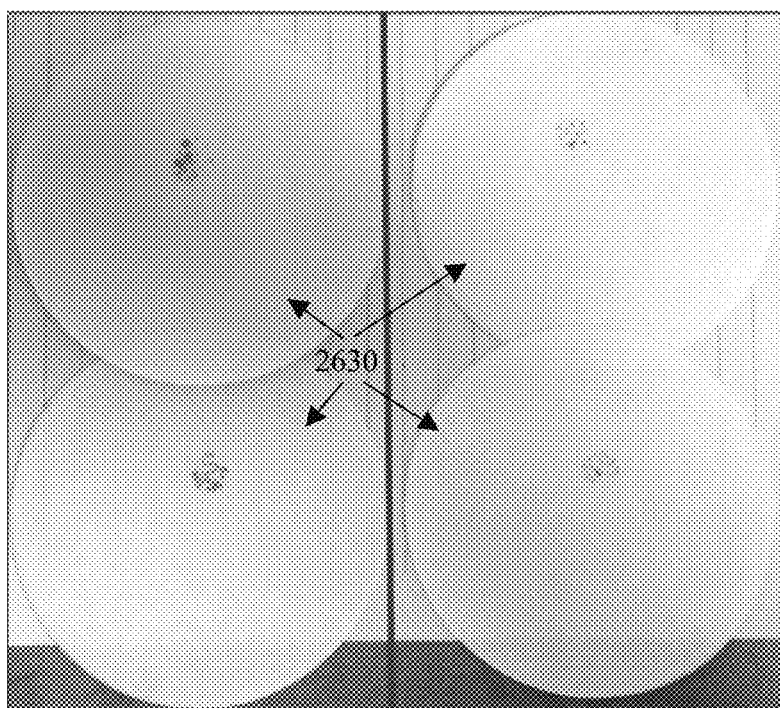
Fig. 15A   Fig. 15B
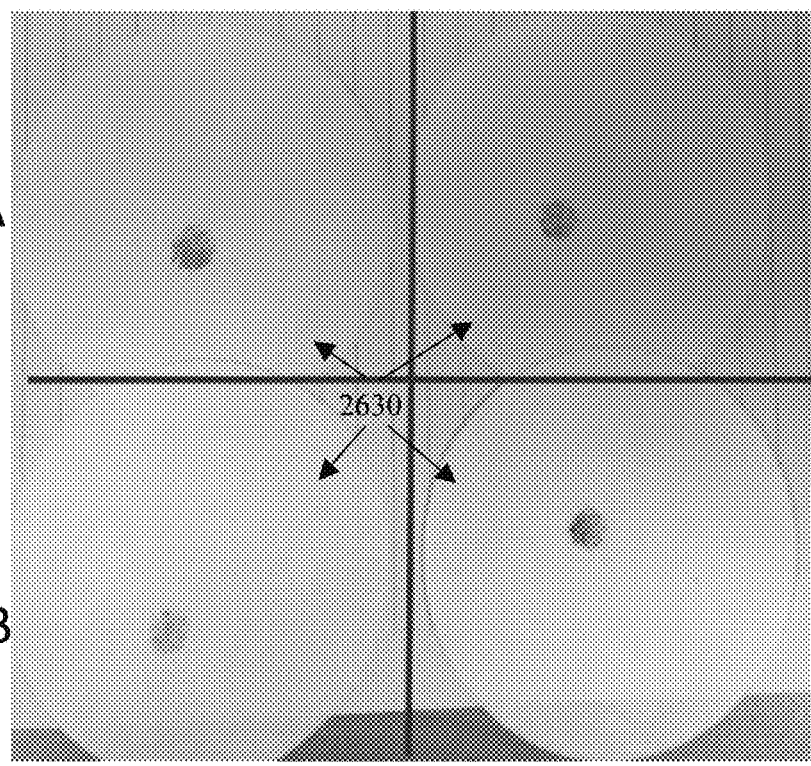
Fig. 16A   Fig. 16C
Fig. 16B   Fig. 16D

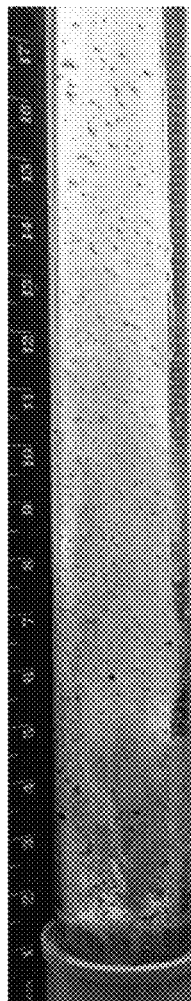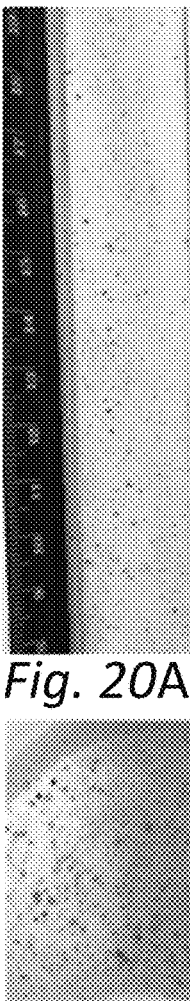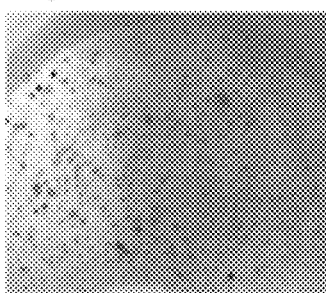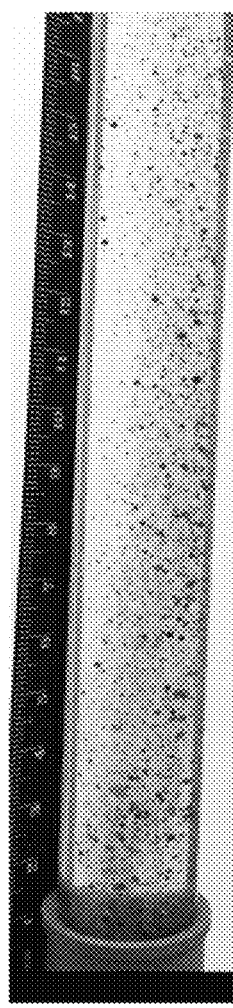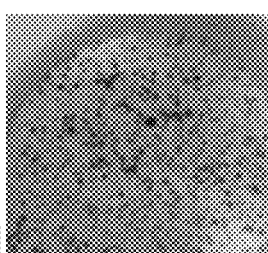
Fig. 20A1    Fig. 20B              Fig. 20C    Fig. 20D

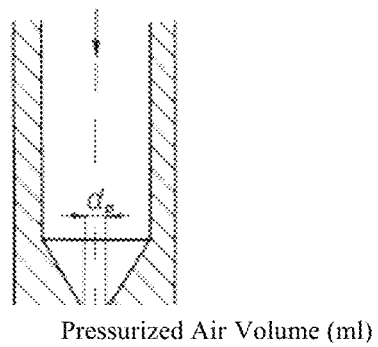
Pressurized Air Volume (ml)
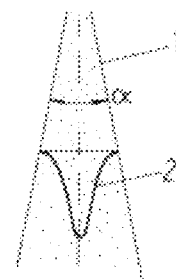
Fig. 35
  35°
Fig. 36B 27°
Fig. 36C 8.7°

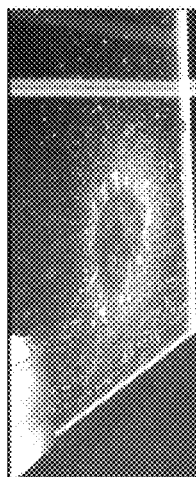 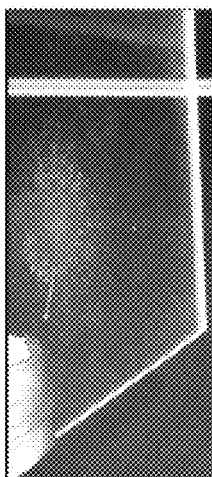 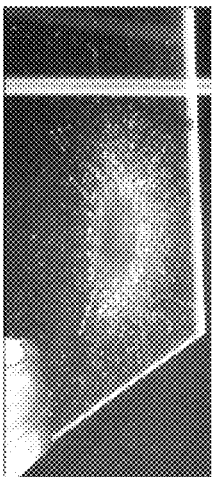 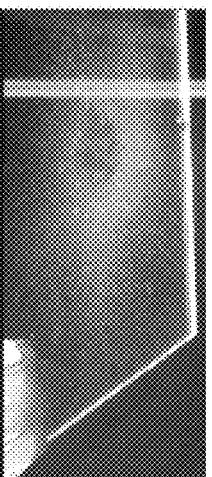 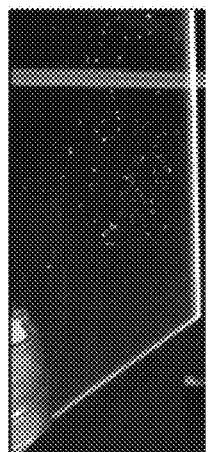
Fig. 39A  Fig. 39B  Fig. 39C  Fig. 39D  Fig. 39E
 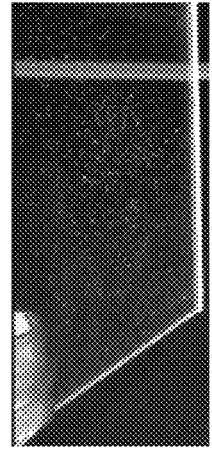 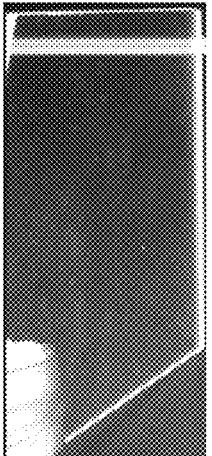 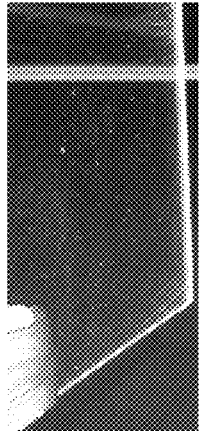 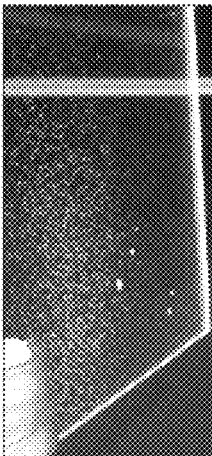
Fig. 39F  Fig. 39G  Fig. 39H  Fig. 39I  Fig. 39J

Effect of Pressure on Release Time

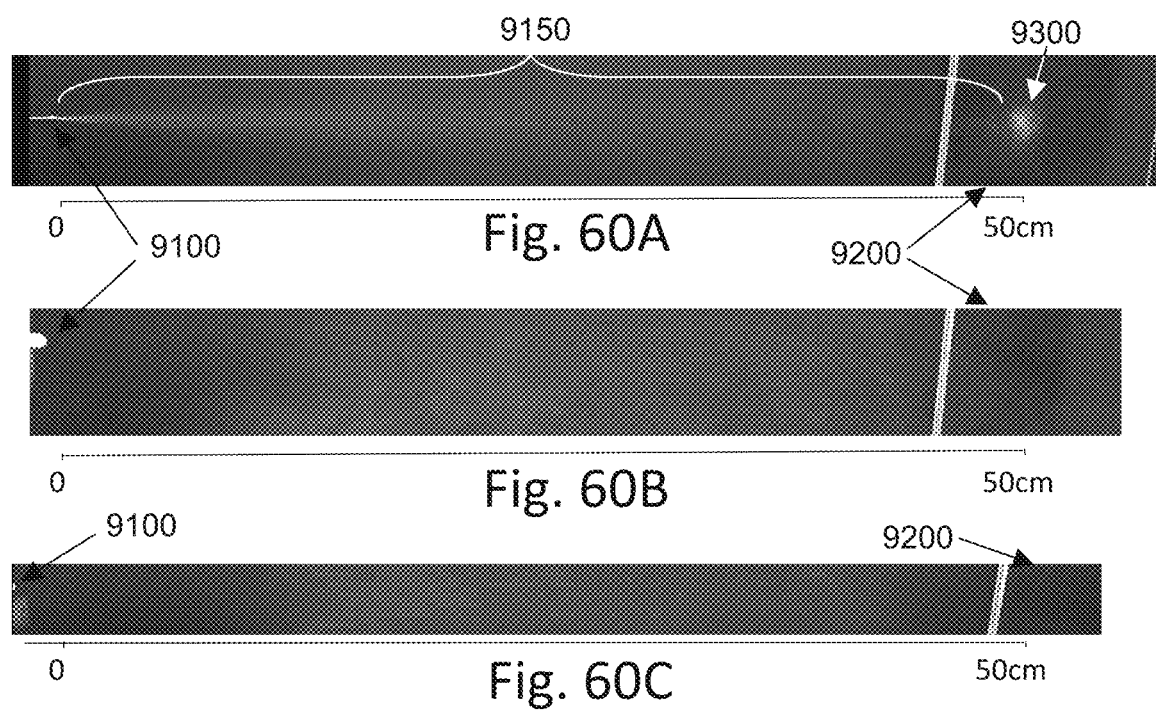

Fig. 61A
Fig. 61B
Fig. 61C
Fig. 61D
Fig. 61E
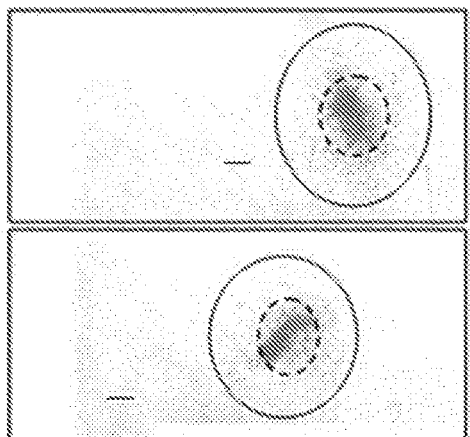
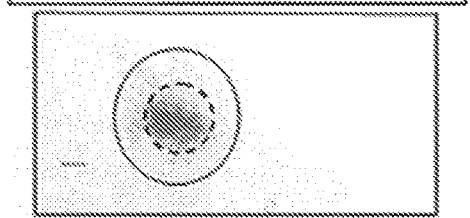
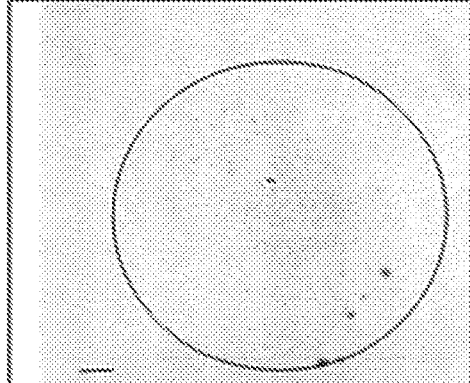
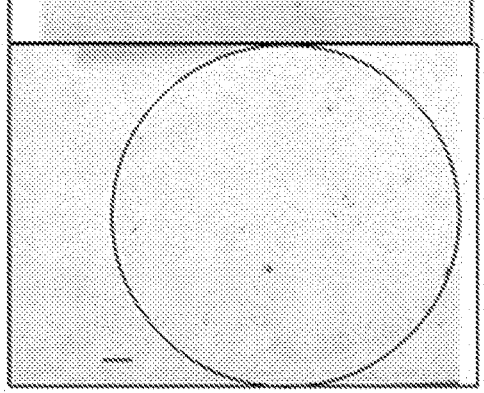

DEVICE AND METHOD FOR AEROSOLIZED DELIVERING OF SUBSTANCE TO A NATURAL ORIFICE OF THE BODY

CROSS REFERENCE TO RELATED PATENT APPLICATIONS

The present application claims the benefit of and priority to U.S. Provisional Patent Application No. 62/117,986, filed Feb. 19, 2015, and U.S. Provisional Patent Application No. 62/077,246, filed Nov. 9, 2014, the entire disclosures of which are incorporated herein by reference.

FIELD OF THE INVENTION

The present invention generally pertains to a system for delivering aerosolized substance to a natural orifice of the body.

BACKGROUND OF THE INVENTION

Many devices of the prior art focus on a mechanism to allow better aerosol formation and better dispersion in the nasal cavity. Other mechanisms for better delivery focus on special formulations that include materials and structures to allow better absorption in the target tissue.

Each of these strategies has its advantages and disadvantages. For example, improvements to the delivery device can improve bringing the material to the desired area, but neglect the need to enhance the absorption of the compound into and through the mucosal layer. On the other hand, improvements to the composition, the formulation or both can improve absorption into and through the mucosal layer, but may well neglect the difficulty of delivering a sufficient amount of the material to the desired tissue.

It is therefore a long felt need to provide a system which can be optimized for efficient delivery of a substance to a target site, said optimization neglecting neither the need to bring sufficient material to the target site, nor the need to ensure adequate absorption into and through the mucosal layer.

SUMMARY OF THE INVENTION

It is an object of the present invention to disclose a system and method for delivering aerosolized substance to a natural orifice of the body It is another object of the present invention to disclose a device for delivering a predetermined volume $V_{sub}$ [ml] of at least one substance, within at least one body cavity of a subject, the device comprising:
a. at least one predefined volume sized and shaped for containing said predetermined volume $V_{sub}$ [ml] of at least one substance;
b. a delivery end for placement in proximity to the body cavity, the delivery end being in fluid communication with the container; the delivery end comprising at least one orifice of diameter D [mm];
c. at least one valve mechanically connectable to the container, characterized by at least two configurations: (i) an ACTIVE CONFIGURATION in which the valve enables delivery of a predetermined volume $V_{sub}$ [ml] of the substance from the container to the body cavity via the delivery end; and, (ii) an INACTIVE CONFIGURATION, in which the valve prevents delivery of the predetermined volume $V_{sub}$ [ml] of the substance from the container to the body cavity;
the valve is reconfigurable from the INACTIVE CONFIGURATION to the ACTIVE CONFIGURATION, and vice versa, within a predetermined period of time, dT, in response to activation of the same; and
d. a fluid tight chamber configured to contain a predetermined volume $V_{gas}$ [ml] of pressurized gas at a predetermined pressure, $P_{gas}$ [barg];
the device is configured, once the valve is reconfigured from the INACTIVE CONFIGURATION to the ACTIVE CONFIGURATION, to entrain the substance by the pressurized gas, and deliver the same via the orifice in the delivery end within the body cavity;
wherein the device is configured to deliver the predetermined volume $V_{sub}$ [ml] of the substance and the predetermined volume $V_{gas}$ of the pressurized gas through the orifice of diameter D [mm] in (a) pressure rate of $dP_{gas}/dT$; (b) volume rate of $dV_{gas}/dT$; and (c) volume rate of $dV_{sub}/dT$; further wherein at least one of the following is held true:
(a) $P_{gas}$ is in the range of about 1-10 barg;
(b) $V_{gas}$ is in the range of about 1-21 ml;
(c) $V_{sub}$ is in the range of about 0.01-7 ml;
(d) D is in the range of 0.2-6 mm;
(e) the pressure rate, $$\frac{dP}{dT} \to \infty;$$

(f) the pressure rate $dP_{gas}/dT$ is greater than about 0.001 barg/ms;
(g) the volume rate $dV_{sub}/dT$ is greater than about 0.0001 ml/ms;
(h) the volume rate $dV_{gas}/dT$ is greater than about 0.001 ml/ms;
(i) the predetermined period of time, $dT \to 0$; and
(j) dT is in the range of about 0 to 500 millisecond.

It is another object of the present invention to disclose the device, wherein at least one of the following is true:
a. the body orifice is a nasal cavity, the mouth, the throat, an ear, the vagina, the rectum, the urethra, and any combination thereof
b. viscosity $\eta$ of the substance is in the range of about $1 \times 10^{-3}$ poise to about 1 poise;
c. DV50 diameter of particles of the substance, after exit from said device, is less than about 100 µm;
d. DV90 diameter of the particles is less than about 1000 µm;
e. a full width of a plume of aerosol comprising said substance and said gas subtends an angle $\theta$ of less than about 25°;
f. particles in the plume have velocities in a range of about 5 m/s to 50 m/s;
g. the pressurized gas comprises air, nitrogen, oxygen, carbon dioxide, helium, neon, xenon and any combination thereof;
h. during dispensing of the at least one substance, a mixture of the predetermined volume $V_{gas}$ [ml] of the pressurized gas and the predetermined volume $V_{sub}$ [ml] of the substance entrained within it forms a plume of aerosol; the aerosol having a predetermined distribution, the distribution being either homogeneous or heterogeneous, the heterogeneous distribution is selected from a group consisting of: an arbitrary distribution, a distribution in which the density of at least one substance within the mixture follows a predetermined pattern, and any combination thereof; characteristics of the aerosol selected from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof;

i. at least one substance is selected from a group consisting of a gas, a liquid, a powder, an aerosol, a slurry, a gel, a suspension and any combination thereof; and j. at least one substance is stored under either an inert atmosphere or under vacuum to prevent reactions during storage.

It is another object of the present invention to disclose the device, wherein said volume is a container.

It is another object of the present invention to disclose the device, wherein the container is a capsule having a main longitudinal axis, the capsule comprising a number n of compartments, the capsule configured to contain the predetermined volume $V_{sub}$ [ml] of the at least one substance, the volume $V_{sub}$ [ml] of the at least one substance containable in at least one of the n compartments; at least one of the following being true:

a. the number n of compartments is an integer greater than or equal to 1; at least one compartment has cross-section with shape selected from a group consisting of: wedge shaped, circular, oval, elliptical, polygonal, annular, and any combination thereof;

b. for the number n of compartments being an integer greater than 1, at least two compartments have different volumes;

c. for the number n of compartments being an integer greater than 1, at least two compartments have the same volume;

d. for the number n of compartments being an integer greater than 1, at least two compartments have different cross-sectional areas;

e. for the number n of compartments being an integer greater than 1, at least two compartments have the same cross-sectional area;

f. for the number n of compartments being an integer greater than 1, at least two compartments contain different substances;

g. for the number n of compartments being an integer greater than 1, at least two compartments contain the same substance;

h. for the number n of compartments being an integer greater than 1, at least two compartments are disposed coaxially around the main longitudinal axis of the capsule;

i. for the number n of compartments being an integer greater than 1, at least two compartments are disposed sequentially along the main longitudinal axis of the capsule;

j. for the number n of compartments greater than 1, the plurality of substances mix during dispensing; and k. for the number n of compartments greater than 1, the plurality of substances react during dispensing.

It is another object of the present invention to disclose the device, wherein the container comprises a port fluidly connectable to the exterior of the device, the port configured such that at least one substance is insertable into the chamber via the port.

It is another object of the present invention to disclose the device, wherein the device comprises a port cover configured to provide an air-tight closure for the port, the port cover slidable along the device, rotatable around the device, rotatable around a hinge on the exterior of the device and any combination thereof.

It is another object of the present invention to disclose the device, wherein, when the substance is delivered into a tube, at least one of the following is true:

a. the distance L travelled down the tube is L and L is substantially independent of said viscosity η of said substance;

b. the distance L travelled down the tube is L, where $L=a_{1a}P+b_{1a}$, the units of L are cm and the units of P are barg, $a_{1a}$ is in a range of about 0 to about 70 and $b_{1a}$ is in a range of about 0 to about 130;

c. L is substantially independent of $V_{sub}$;

d. the distance travelled down the tube is L, $L=a_{1b}P^3-b_{1b}P^2+c_{1b}P$; the units of L are cm and the units of P are barg, $a_{1b}$ is in a range of about 2 to about 6, $b_{1b}$ is in a range of about −20 to about −60 and $c_{1b}$ is in a range of about 70 to about 230;

e. the distance travelled down the tube is L, $L=a_{1c}P^{b1c}$; the units of L are cm and the units of P are barg, $a_{1c}$ is in a range of about 71 to about 120 and $b_{1c}$ is in a range of about 0.30 to 0.63;

f. the distance travelled down the tube is L, $L=a_{2a}/(1+b_{2a}\exp(-c_{2a}D))$; the units of L are cm and the units of P are barg, $a_{2a}$ is in a range of about 325 to about 363, $b_{2a}$ is in a range of about −47 to about 163 and $c_{2a}$ is in a range of about 7 to about 15;

g. the distance travelled down the tube is L, $L=a_{2b}D^2+b_{2b}D+c_{2b}$; the units of L are cm and the units of P are barg, $a_{2b}$ is in a range of about −928 to about −229, $b_{2b}$ is in a range of about 600 to about 1378 and $c_{2b}$ is in a range of about −160 to about 15;

h. the distance travelled down the tube is L, $L=a_{3a}V_{sub}+b_{3a}$; the units of L are cm and the units of P are barg, $a_{3a}$ is in a range of about 0.55 to about 0.59 and $b_{3a}$ is in a range of about 96 to about 467;

i. the distance travelled down the tube is L, $L=a_{5a}V_{gas}+b_{5a}$; the units of L are cm and the units of P are barg, $a_{5a}$ is in a range of about 3.7 to about 13.5 and $b_{5a}$ is in a range of about 152 to about 248;

j. the distance travelled down the tube is L, $L=b5b\,V_{gas}/(a_{5b}+V_{gas})$; the units of L are cm and the units of P are barg, $a_{5b}$ is in a range of about −0.18 to about 5.3 and $b_{5b}$ is in a range of about 268 to about 498; and k. the distance travelled down the tube is L, $L=a_{5c}V_{gas}b_{5c}$; the units of L are cm and the units of P are barg, $a_{5c}$ is in a range of about −19 to about 250 and $b_{5c}$ is in a range of about −0.09 to about 0.9.

It is another object of the present invention to disclose a device for delivering a predetermined amount $M_{sub}$ [mg] of at least one substance within at least one body cavity of a subject, the device comprising:

a. at least one predefined volume sized and shaped for containing the predetermined amount $M_{sub}$ [mg] of the at least one substance;

b. a delivery end for placement in proximity to the body cavity, the aid delivery end being in fluid communication with the container; the delivery end comprising at least one orifice of diameter D [mm];

c. at least one valve mechanically connectable to the container, characterized by at least two configurations: (i) an ACTIVE CONFIGURATION in which the valve enables delivery of a predetermined amount $M_{sub}$ [mg] of the substance from the container to the body cavity via the delivery end; and, (ii) an INACTIVE CONFIGURATION, in which the valve prevents delivery of the predetermined amount $M_{sub}$ [mg] of the substance from the container to the body cavity;

the valve is reconfigurable from the INACTIVE CONFIGURATION to the ACTIVE CONFIGURATION, and vice versa, within a predetermined period of time, dT, in response to activation of the same; and d. a fluid tight chamber configured to contain a predetermined volume $V_{gas}$ [ml] of pressurized gas at a predetermined pressure, $P_{gas}$ [barg];

the device is configured, once the valve is reconfigured from the INACTIVE CONFIGURATION to the ACTIVE CONFIGURATION, to entrain the substance by the pressurized gas, and deliver the same via the orifice in the delivery end within the body cavity;

wherein the device is configured to deliver the predetermined amount $M_{sub}$ [mg] of the substance and the predetermined volume $V_{gas}$ of the pressurized gas through the orifice of diameter D [mm] in a pressure rate of $dP_{gas}/dT$; further wherein at least one of the following is held true:

(a) $P_{gas}$ is in the range of about 1-10 barg;
(b) $V_{gas}$ is in the range of about 1-21 ml;
(c) $M_{sub}$ is in the range of about 0.01-1000 mg;
(d) D is in the range of 0.2-6 mm;
(e) the pressure rate, $$\frac{dP}{dT} \to \infty;$$

(f) the pressure rate is greater than about 0.001 barg/ms;
(g) the amount rate $dM_{sub}/dT$ is greater than about 0.0001 mg/ms;
(h) the volume rate $dV_{gas}/dT$ is greater than about 0.001 ml/ms;
(i) the predetermined period of time, $dT \to 0$; and
(j) dT is in the range of about 0 to 500 millisecond.

It is another object of the present invention to disclose the device, wherein at least one of the following is true:

a. the body orifice is a nasal cavity, the mouth, the throat, an ear, the vagina, the rectum, the urethra, and any combination thereof;
b. viscosity η of the substance is in a range of about $1 \times 10^{-3}$ poise to about 1 poise.
c. DV50 diameter of particles of the substance, after exit from the device, is less than about 100 μm;
d. DV90 diameter of the particles of the substance, after exit from the device, is less than about 1000 μm;
e. the full width of the plume of aerosol comprising the substance and the gas subtends an angle θ of less than about 25°;
f. particles in the plume have velocities in the range of about 5 m/s to 50 m/s;
g. the pressurized gas comprises air, nitrogen, oxygen, carbon dioxide, helium, neon, xenon and any combination thereof
h. during dispensing of the at least one substance, a mixture of the predetermined volume $V_{gas}$ [ml] of the pressurized gas with the predetermined mass $M_{sub}$ [mg] of the substance entrained within it forms a plume of aerosol, the aerosol having a predetermined distribution, the distribution being either homogeneous or heterogeneous, the heterogeneous distribution is selected from a group consisting of: an arbitrary distribution, a distribution in which the density of the at least one substance within the mixture follows a predetermined pattern, and any combination thereof; characteristics of the aerosol selected from a group consisting of: particle size, particle shape, particle distribution, and any combination thereof, are determinable from characteristics of the device selected from a group consisting of: predetermined volume of the pressurized gas, predetermined volume of the substance, predetermined pressure of the pressurized gas, predetermined orifice size, and any combination thereof;
i. at least one substance is selected from a group consisting of a gas, a liquid, a powder, an aerosol, a slurry, a gel, a suspension and any combination thereof;
j. at least one substance is stored under either an inert atmosphere or under vacuum to prevent reactions during storage; and
k. a dose-response curve is substantially linear for brain concentration of the substance when administered nasally via the device;
l. a dose-response curve for brain concentration having a fit selected from a group consisting of: logarithmic, parabolic, exponential, sigmoid, power-low, and any combination thereof; of said substance when administered nasally via said device.

It is another object of the present invention to disclose the device, wherein said volume is a container.

It is another object of the present invention to disclose the device, wherein the container is a capsule having a main longitudinal axis, the capsule comprising a number n of compartments, the capsule configured to contain the predetermined mass $M_{sub}$ [mg] of the at least one substance, the mass $M_{sub}$ [mg] of the at least one substance containable in at least one of the n compartments; at least one of the following being true:

a. the number n of compartments is an integer greater than or equal to 1; at least one compartment has cross-section with shape selected from a group consisting of: wedge shaped, circular, oval, elliptical, polygonal, annular, and any combination thereof;
b. for the number n of compartments being an integer greater than 1, at least two compartments have different volumes;
c. for the number n of compartments being an integer greater than 1, at least two compartments have the same volume;
d. for the number n of compartments being an integer greater than 1, at least two compartments have different cross-sectional areas;
e. for the number n of compartments being an integer greater than 1, at least two compartments have the same cross-sectional area;
f. for the number n of compartments being an integer greater than 1, at least two compartments contain different substances;
g. for the number n of compartments being an integer greater than 1, at least two compartments contain the same substance;
h. for the number n of compartments being an integer greater than 1, at least two compartments are disposed coaxially around the main longitudinal axis of the capsule;
i. for the number n of compartments being an integer greater than 1, at least two compartments are disposed sequentially along the main longitudinal axis of the capsule;
j. for the number n of compartments greater than 1, the plurality of substances mix during dispensing; and
k. for the number n of compartments greater than 1, the plurality of substances react during dispensing.

It is another object of the present invention to disclose the device, wherein the container comprises a port fluidly connectable to the exterior of the device, the port configured such that a substance is insertable into the chamber via the port.

It is another object of the present invention to disclose the device, wherein the device comprises a port cover configured to provide an air-tight closure for the port, the port cover slidable along the device, rotatable around the device, rotatable around a hinge on the exterior of the device and any combination thereof.

It is another object of the present invention to disclose the device, wherein, when the substance is delivered into a tube, at least one of the following is true:
a. the distance travelled down the tube is L and L is substantially independent of the viscosity η of the substance;
b. the distance travelled down the tube is L, where $L=a_{6a}P+b_{6a}$; the units of L are cm and the units of P are barg, $a_{6a}$ is in a range of about 0 to about 116 and $b_{6a}$ is in a range of about 0 to about 306;
c. the distance travelled down the tube is L, where $L=a_{6b}P^3-b_{6b}P^2+c_{6b}P$; the units of L are cm and the units of P are barg, $a_{6b}$ is in a range of about 6.5 to about 9.75, $b_{6b}$ is in a range of about −65 to about −97.5 and $c_{6b}$ is in a range of about 202 to about 303;
d. the distance travelled down the tube is L, where $L=a_{6c}P^{b6c}$; the units of L are cm and the units of P are barg, $a_{6c}$ is in a range of about 0 to about 902 and $b_{6c}$ is in a range of about 0 to about 3.72;
e. the distance travelled down the tube is L, where $L=a_{7a}V_{gas}+b_{7a}$; the units of L are cm and the units of P are barg, $a_{7a}$ is in a range of about 0 to about 10 and $b_{7a}$ is in a range of about 165 to about 282;
f. the distance travelled down the tube is L, where $L=b_{7b}V_{gas}/(a_{7b}+V_{gas})$; the units of L are cm and the units of P are barg, $a_{1a}$ is in a range of about −0.26 to about 2.05 and $b_{7b}$ is in a range of about 235 to about 350; and
g. the distance travelled down the tube is L, where $L=a_{7c}V_{gas}^{b7c}$; the units of L are cm and the units of P are barg, $a_{7c}$ is in a range of about 0 to about 320 and $b_{7c}$ is in a range of about 0 to about 0.96.

It is another object of the present invention to disclose a method of delivering a predetermined volume $V_{sub}$ [ml] of at least one substance within at least one body cavity of a subject, comprising:
a. providing a device comprising:
  i. a least one predefined volume sized and shaped for containing the predetermined volume $V_{sub}$ [ml] of the at least one substance;
  ii. a delivery end in fluid communication with the container; the delivery end comprising at least one orifice of diameter D [mm];
  iii. at least one valve mechanically connected to the container, characterized by at least two configurations: (i) an ACTIVE CONFIGURATION in which the valve enables delivery of the predetermined volume $V_{sub}$ [ml] of the substance from the container to the body cavity via the delivery end; and, (ii) an INACTIVE CONFIGURATION, in which the valve prevents delivery of the predetermined volume $V_{sub}$ [ml] of the substance from the container to the body cavity;
    the valve is reconfigurable from the INACTIVE CONFIGURATION to the ACTIVE CONFIGURATION, and vice versa, within a predetermined period of time, dT, in response to activation of the same; and
  iv. a fluid tight chamber configured to contain predetermined volume $V_{gas}$ [ml] of pressurized gas at a predetermined pressure, $P_{gas}$ [barg];
b. emplacing the substance in the predefined volume;
c. setting the valve in the inactive configuration;
d. pressurizing the fluid-tight chamber with the gas to the predetermined pressure;
e. placing the delivery end in proximity to the body cavity;
f. reconfiguring the valve from the INACTIVE CONFIGURATION to the ACTIVE CONFIGURATION thereby entraining the substance in the predetermined volume $V_{gas}$ of the pressurized gas; thereby
g. delivering the predetermined volume $V_{sub}$ [ml] of the substance and the predetermined volume $V_{gas}$ of the pressurized gas through the orifice of diameter D [mm] in a pressure rate of $dP_{gas}/dT$;
wherein at least one of the following is held true:
(a) $P_{gas}$ is in the range of about 1-10 barg;
(b) $V_{gas}$ is in the range of about 1-21 ml;
(c) $V_{sub}$ is in the range of about 0.01-7 ml;
(d) D is in the range of 0.2-6 mm;
(f) the pressure rate, $$\frac{dP}{dT} \to \infty;$$

(g) the pressure rate is greater than about 0.001 barg/ms;
(h) the volume rate $dV_{sub}/dT$ is greater than about 0.0001 ml/ms;
(i) the volume rate $dV_{gas}/dT$ is greater than about 0.001 ml/ms;
(j) the predetermined period of time, dT→0; and
(k) dT is in the range of about 0 to 500 millisecond.

It is another object of the present invention to disclose the method, additionally comprising at least one of the following steps:
a. selecting the body orifice from a group consisting of a nasal cavity, the mouth, the throat, an ear, the vagina, the rectum, the urethra, and any combination thereof;
b. selecting viscosity η of the substance to be in the range of about $1\times10^{-3}$ poise to about 1 poise;
c. characterizing particles of said substance in a delivered aerosol, said aerosol a mixture of said at least one substance and said gas, by a DV50 diameter, said DV50 diameter being less than about 100 μm;
d. characterizing said particles by a DV90 diameter of less than about 1000 μm;
e. characterizing a plume of said aerosol by a plume angle θ, said plume angle θ subtending the full width of said plume, said plume angle θ subtending an angle of less than about 25';
f. characterizing velocities of particles in said plume as being in a range of about 5 m/s to 50 m/s;
g. selecting said gas from a group consisting of: air, nitrogen, oxygen, carbon dioxide, helium, neon, xenon and any combination thereof;
h. dispensing said at least one substance, and during said step of dispensing, forming a plume of aerosol with predetermined distribution from a mixture of the predetermined volume $V_{gas}$ [ml] of said pressurized gas and said predetermined volume $V_{sub}$ [ml] entrained within it; selecting said predetermined distribution from a group consisting of: a homogeneous distribution, a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined volume of said substance, said predetermined pressure of said pressurized gas, said predetermined orifice size, and any combination thereof;
i. selecting said substance from a group consisting of: a gas, a liquid, a powder, a slurry, a gel, a suspension, and any combination thereof;
j. storing at least one said substance under either an inert atmosphere or under vacuum, thereby preventing reactions during storage; and
k. characterizing a dose-response curve for brain concentration of said substance to be of substantially linear form;
l. a dose-response curve for brain concentration having a fit selected from a group consisting of logarithmic, parabolic, exponential, sigmoid, power-low, and any combination thereof; of said substance when administered nasally via said device.

It is another object of the present invention to disclose the method, wherein said volume is a container.

It is another object of the present invention to disclose the method, additionally comprising steps of providing the container comprising a capsule having a main longitudinal axis, the capsule comprising a number n of compartments, configuring the capsule to contain the predetermined volume $V_{sub}$ [ml] of the at least one substance, containing the volume $V_{sub}$ [ml] of the substance in at least one of the n compartments; additionally comprising at least one of the following steps:
a. providing the capsule with n compartments; n is an integer greater than or equal to 1;
b. selecting the cross-sectional shape of at least one of the n compartments from a group consisting of: wedge shaped, circular, oval, elliptical, polygonal, annular, and any combination thereof;
c. for the number n of compartments being an integer greater than 1, providing at least two of the plurality of compartments having different volumes;
d. for the number n of compartments being an integer greater than 1, providing at least two compartments having the same volume;
e. for the number n of compartments being an integer greater than 1, providing at least two compartments having different cross-sectional areas;
f. for the number n of compartments being an integer greater than 1, providing at least two compartments having the same cross-sectional area;
g. for the number n of compartments being an integer greater than 1, providing at least two compartments containing different substances;
h. for the number n of compartments being an integer greater than 1, providing at least two compartments containing the same substance;
i. for the number n of compartments being an integer greater than 1, disposing the plurality of compartments coaxially around the main longitudinal axis of the capsule;
j. for the number n of compartments being an integer greater than 1, disposing the plurality of compartments sequentially along the main longitudinal axis of the capsule;
k. for the number n of compartments being an integer greater than 1, mixing the plurality of substances during dispensing; and
l. for the number n of compartments being an integer greater than 1, reacting the plurality of substances during dispensing.

It is another object of the present invention to disclose the method, additionally comprising step of inserting the predetermined volume $V_{sub}$ [ml] of the at least one substance into the container via a port fluidly connectable to the exterior of the device.

It is another object of the present invention to disclose the method, additionally comprising step of providing an airtight closure for the port, and of moving the port cover relative to the device in at least one motion selected from a group consisting of: sliding the port cover along the device, rotating the port cover around the device, rotating the port cover around a hinge on the exterior of the device and any combination thereof.

It is another object of the present invention to disclose the method, additionally comprising steps of delivering the substance into a tube and measuring the distance L the substance travels down the tube; and additionally comprising at least one of the following steps:
a. selecting viscosity η such that L is substantially independent of viscosity η of the substance;
b. selecting $V_{sub}$ such that L is substantially independent of $V_{sub}$;
c. $L=a_{1a}P+b_{1a}$ and selecting $a_{1a}$ to be in a range of about 0 to about 70 and $b_{1a}$ to be in a range of about 0 to about 130, where L is in cm and P is in barg;
d. $L=a_{1b}P^3-b_{1b}P^2+c_{1b}P$ and selecting $a_{1b}$ to be in a range of about 2 to about 6, $b_{1b}$ to be in a range of about −20 to about −60 and $c_{1b}$ to be in a range of about 70 to about 230, where L is in cm and P is in barg;
e. $L=a_{1c}P^{b1c}$ and selecting $a_{1c}$ to be in a range of about 71 to about 120 and $b_{1c}$ to be in a range of about 0.30 to 0.63, where L is in cm and P is in barg;
f. $L=a_{2a}/(1+b_{2a}\exp(-c_{2a}D))$ and selecting $a_{2a}$ to be in a range of about 325 to about 363, $b_{2a}$ to be in a range of about −47 to about 163 and $c_{2a}$ to be in a range of about 7 to about 15, where L is in cm and P is in barg;
g. $L=a_{2b}D^2+b_{2b}D+c2b$ and selecting $a_{2b}$ to be in a range of about 928 to about −229, $b_{2b}$ to be in a range of about 600 to about 1378 and $c_{2b}$ to be in a range of about −160 to about 15, where L is in cm and P is in barg;
h. $L=a_{3a}V_{sub}+b_{3a}$ and selecting $a_{3a}$ to be in a range of about −0.55 to about 0.59 and $b_{3a}$ to be in a range of about 96 to about 467, where L is in cm and P is in barg;
i. $L=a_{5a}V_{gas}+b_{5a}$ and selecting $a_{5a}$ to be in a range of about 3.7 to about 13.5 and $b_{5a}$ to be in a range of about 152 to about 248;
j. $L=b_{5b}V_{gas}/(a_{5b}+V_{gas})$ and selecting $a_{5b}$ to be in a range of about −0.18 to about 5.3 and $b_{5b}$ to be in a range of about 268 to about 498, where L is in cm and P is in barg; and
k. $L=a_{5c}V_{gas}^{b5c}$ and selecting $a_5$, to be in a range of about −19 to about 250 and $b_5$, to be in a range of about −0.09 to about 0.9, where L is in cm and P is in barg.

It is another object of the present invention to disclose a method of delivering a predetermined amount $M_{sub}$ [mg] of at least one substance within at least one body cavity of a subject, comprising:
a. providing a device comprising:
   i. at least one predefined volume sized and shaped for containing said predetermined amount $M_{sub}$ [mg] of said at least one substance;

ii. a delivery end in fluid communication with said container; said delivery end comprisings at least one orifice of diameter D [mm];

iii. at least one valve mechanically connected to said container, characterized by at least two configurations: (i) an ACTIVE CONFIGURATION in which said valve enables delivery of said predetermined amount $M_{sub}$ [mg] of said at least one substance from said container to said body cavity via said delivery end; and, (ii) an INACTIVE CONFIGURATION, in which said valve prevents delivery of said predetermined amount $M_{sub}$ [mg] of said substance from said container to said body cavity;

said valve is reconfigurable from said INACTIVE CONFIGURATION to said ACTIVE CONFIGURATION, and vice versa, within a predetermined period of time, dT, in response to activation of the same; and iv. a fluid tight chamber configured to contain predetermined volume $V_{gas}$ [ml] of pressurized gas at a predetermined pressure, $P_{gas}$ [barg];

b. emplacing said substance in said predefined volume;
c. setting said valve in said inactive configuration;
d. pressurizing said fluid-tight chamber with said gas to said predetermined pressure;
e. placing said delivery end in proximity to said body cavity;
f. reconfiguring said valve from said INACTIVE CONFIGURATION to said ACTIVE CONFIGURATION thereby entraining said substance in said predetermined volume $V_{gas}$ of said pressurized gas; thereby
g. delivering said predetermined amount $M_{sub}$ [mg] of said substance and said predetermined volume $V_{gas}$ of said pressurized gas through said orifice of diameter D [mm] in a pressure rate of $dP_{gas}/dT$;

wherein at least one of the following is held true:
(a) $P_{gas}$ is in the range of about 1-10 barg;
(b) $V_{gas}$ is in the range of about 1-21 ml;
(c) $M_{sub}$ is in the range of about 1-1000 mg;
(d) D is in the range of 0.2-6 mm;
(e) said pressure rate, $$\frac{dP}{dT} \to \infty;$$

(f) said pressure rate is greater than about 0.001 barg/ms;
(g) said amount rate $dM_{sub}/dT$ is greater than about 0.0001 mg/ms;
(h) said volume rate $dV_{gas}/dT$ is greater than about 0.001 ml/ms;
(i) said predetermined period of time $dT \to 0$; and
(j) dT is in the range of about 0 to 500 millisecond.

It is another object of the present invention to disclose the method, additionally comprising at least one of the following steps:
a. selecting said body orifice from a group consisting of a nasal cavity, the mouth, the throat, an ear, the vagina, the rectum, the urethra, and any combination thereof;
b. selecting viscosity η of said substance to be in a range of about $1 \times 10^{-3}$ poise to about 1 poise.
c. characterizing particles of said substance in a delivered aerosol, said aerosol a mixture of said at least one substance and said gas, by a DV50 diameter, said DV50 diameter being less than about 100 μm;
d. characterizing said particles by a DV90 diameter of less than about 1000 μm;
e. characterizing a plume of said aerosol by a plume angle θ, said plume angle θ subtending the full width of said plume, said plume angle θ subtending an angle of less than about 25';
f. characterizing velocities of particles in said plume as being in a range of about 5 m/s to 50 m/s;
g. selecting said gas from a group consisting of: air, nitrogen, oxygen, carbon dioxide, helium, neon, xenon and any combination thereof;

h. dispensing said at least one substance, and during said step of dispensing, forming a plume of aerosol with predetermined distribution from a mixture of the predetermined volume $V_{gas}$ [ml] of said pressurized gas and said predetermined amount $M_{sub}$ [mg] entrained within it; selecting said predetermined distribution from a group consisting of: a homogeneous distribution, a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined volume of said substance, said predetermined pressure of said pressurized gas, said predetermined orifice size, and any combination thereof;
i. selecting said substance from a group consisting of: a gas, a liquid, a powder, a slurry, a gel, a suspension, and any combination thereof;
j. storing at least one said substance under either an inert atmosphere or under vacuum, thereby preventing reactions during storage;
k. characterizing a dose-response curve for brain concentration of said substance to be of substantially linear form;
l. a dose-response curve for brain concentration having a fit selected from a group consisting of logarithmic, parabolic, exponential, sigmoid, power-low, and any combination thereof; of said substance when administered nasally via said device.

It is another object of the present invention to disclose the method, wherein said volume is a container.

It is another object of the present invention to disclose the method, additionally comprising step of providing said container comprising a capsule having a main longitudinal axis, said capsule comprising at least one compartment, said compartment configured to contain said predetermined amount $M_{sub}$ [mg] of said at least one substance.

It is another object of the present invention to disclose the method, additionally comprising at least one of the following steps:
a. providing said capsule with one compartment;
b. providing said capsule with n compartments; 11 is an integer greater than 1;
c. providing at least two of said plurality of said compartments having different volumes;
d. providing at least two said compartments having the same volume;
e. providing at least two said compartments having different cross-sectional areas;
f. providing at least two said compartments having the same cross-sectional area;
g. providing at least two of said compartments containing different substances;
h. providing at least two of said compartments containing the same substance;
i. disposing said plurality of compartments coaxially around said main longitudinal axis of said capsule;
j. disposing said plurality of compartments sequentially along said main longitudinal axis of said capsule;
k. mixing said plurality of substances during said dispensing; and
l. reacting said plurality of substances during said dispensing.

It is another object of the present invention to disclose the method as defined above, additionally comprising step of selecting the cross-sectional shape of said at least one compartment from a group consisting of: wedge shaped, circular, oval, elliptical, polygonal, annular, and any combination thereof.

It is another object of the present invention to disclose the method, additionally comprising step of inserting said predetermined amount $M_{sub}$ [mg] of said at least one substance into said container via a port fluidly connectable to the exterior of said device.

It is another object of the present invention to disclose the method, additionally comprising step of providing an airtight closure for said port, and of moving said port cover relative to said device in at least one motion selected from a group consisting of: sliding said port cover along said device, rotating said port cover around said device, rotating said port cover around a hinge on the exterior of said device and any combination thereof.

It is another object of the present invention to disclose the method, additionally comprising step of selecting said substance from a group consisting of a gas, a liquid, a powder, an aerosol, a slurry, a gel, a suspension and any combination thereof.

It is another object of the present invention to disclose the method, additionally comprising step of storing at least one said substance under either an inert atmosphere or under vacuum, thereby preventing reactions during storage.

It is another object of the present invention to disclose the method, additionally comprising step of selecting said viscosity $\eta$ such that, after steps of delivering said substance into a tube and measuring the distance L said substance travels down the tube, L is substantially independent of viscosity $\eta$ of said substance.

It is another object of the present invention to disclose the method, additionally comprising steps of delivering said substance into a tube, measuring the distance L said substance travels down the tube, $L=a_{6a}P+b_{6a}$ where L is in cm and P is in barg and selecting $a_{6a}$ to be in a range of about 0 to about 116 and $b_{6a}$ to be in a range of about 0 to about 306.

It is another object of the present invention to disclose the method, additionally comprising steps of delivering said substance into a tube, measuring the distance L said substance travels down the tube, $L=a_{6b}P^3-b_{6b}P^2+c_{6b}P$ where L is in cm and P is in barg and selecting $a_{6b}$ to be in a range of about 6.5 to about 9.75, $b_{6b}$ to be in a range of about −65 to about −97.5 and $c_{6b}$ to be in a range of about 202 to about 303.

It is another object of the present invention to disclose the method, additionally comprising steps of delivering said substance into a tube, measuring the distance L said substance travels down the tube, $L=a_{6c}P^{b6c}$ where L is in cm and P is in barg and selecting $a_{6c}$ to be in a range of about 0 to about 902 and $b_{6c}$ to be in a range of about 0 to about 3.72.

It is another object of the present invention to disclose the method, additionally comprising steps of delivering said substance into a tube, measuring the distance L said substance travels down the tube, $L=a_{7a}V_{gas}+b_{7a}$ and selecting $a_{7a}$ to be in a range of about 0 to about 10 and $b_{7a}$ to be in a range of about 165 to about 282.

It is another object of the present invention to disclose the method, additionally comprising steps of delivering said substance into a tube, measuring the distance L said substance travels down the tube, $L=b_{7b}V_{gas}/(a_{7b}+V_{gas})$ where L is in cm and P is in barg and selecting $a_{1a}$ to be in a range of about −0.26 to about 2.05 and $b_{7b}$ to be in a range of about 235 to about 350.

It is another object of the present invention to disclose the method, additionally comprising steps of delivering said substance into a tube, measuring the distance L said substance travels down the tube, L $a_{7c}V_{gas}^{b7c}$ where L is in cm and P is in barg and selecting $a_{7c}$ to be in a range of about 0 to about 320 and $b_{7c}$ to be in a range of about 0 to about 0.96.

It is another object of the present invention to disclose the method, additionally comprising step of calculating said pressure P from $P=a_{p1}V_{sub}^{-bp1}$, where L is in cm and P is in barg and $a_{p1}$ is in a range from 1 to 20,000 and $b_{p1}$ is in a range from 1 to 2.

It is another object of the present invention to disclose the method, additionally comprising step of calculating said release time T from $$T=a_{v2}+b_{v2}(V_{gas}+V_{sub}),$$

where $a_{v2}$ is in a range of −100 ms to 100 ms and $b_{v2}$ is in a range of −5 to 5, the units of $V_{gas}$ and $V_{sub}$ being ml, $V_{sub}$ being $M_{sub}m_{sub}$, where $m_{sub}$ is the molecular weight of the substance.

BRIEF DESCRIPTION OF THE DRAWINGS

The invention is herein described, by way of example only, with reference to the accompanying drawings, wherein:

FIGS. 1A-D show examples of the prior art;

FIG. 2 shows a cross-section of the face, illustrating zones in the nose from which material therein transfers to different parts of the body;

FIG. 3 illustrates an embodiment of a device of the present invention;

FIGS. 4A-E and 5 illustrate embodiments of capsules;

FIGS. 6A-D and 7A-C illustrate an embodiment of a device of the present invention;

FIGS. 8A-D and 9A-H illustrate embodiments of nozzles for devices of the present invention;

FIG. 10 illustrates an embodiment of the device of the present invention;

FIG. 11 illustrates the formation of an aerosol within the nozzle of the a device of the present invention;

FIG. 12 illustrates an experimental setup;

FIGS. 13A-B, 14A-B, 15A-B and 16A-D show the results of experiments using the setup;

FIGS. 17 and 18A-B show uptake of material to the olfactory epithelium using a SipNose device;

FIGS. 19A-D, 20A-D, 21A-D, 22A-C and 23A-C show results of discharge from devices into the base of an oil-filled column;

FIG. 24 shows pressure developed in a closed tube after discharge from devices into the tube;

FIGS. 25A-C show a nasal cast and results of discharge of devices into the nasal cast;

FIGS. 26A-C, 27A-B, 28A-B, 29, 30A-C, and 31-33 illustrate dependence of discharge depth on various device parameters;

FIG. 34 illustrates depth of penetration into a nasal cast;

FIG. 35 illustrates an orifice, identifying the plume angle;

FIGS. 36A-C illustrate plume angle for different devices;

FIGS. 37A-B illustrate amount of material exiting a nasal cast for different devices;

FIG. 38 illustrates an experimental setup;

FIGS. 39A-J show the results of experiments using the setup;

FIG. 40 shows the concentration of insulin in the brain;

FIGS. 41A-C show the concentration of insulin in the blood and brain;

FIGS. 42A-D, 43A-D, 44A-D, 45A-D, 46A-D, 47A-D, 48A-D, 49A-D, 50A-D, 51A-D, 52A-D, 53A-D, 54A-D and 55A-D illustrate time spaced particle size measurements;

Figure 62:
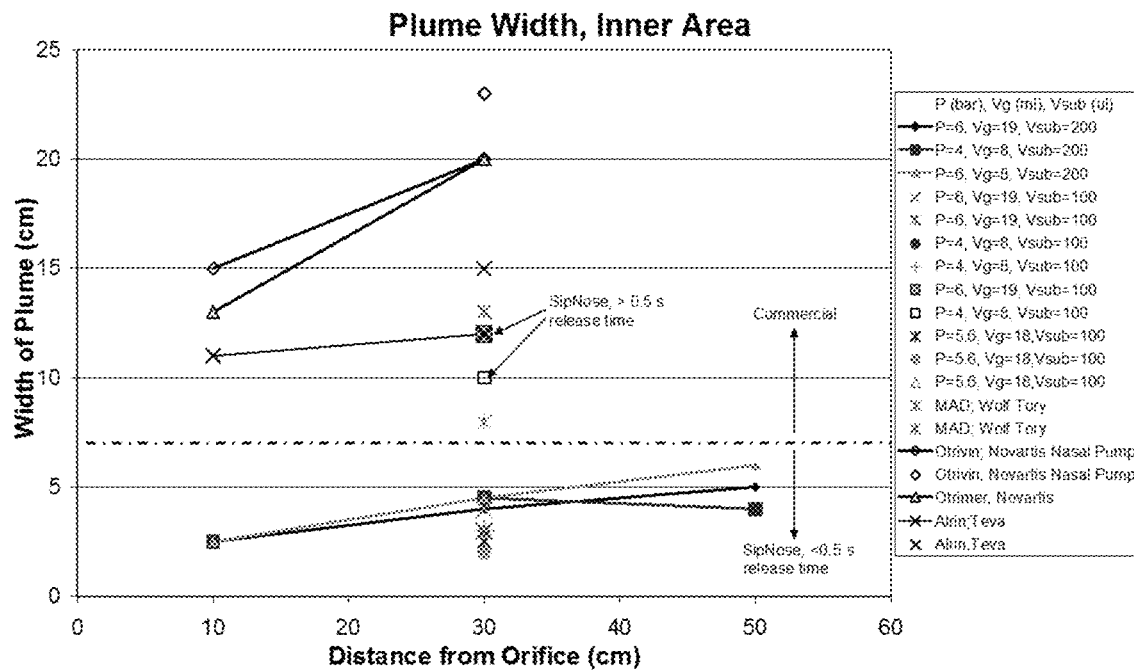
Figure 63:
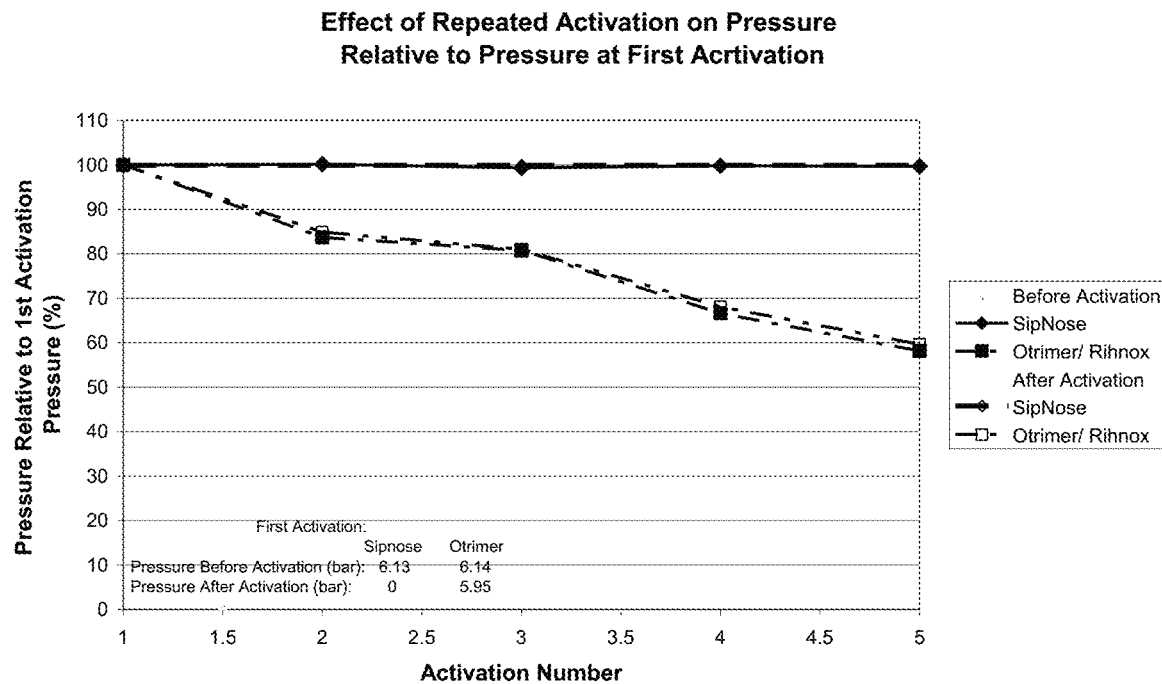

FIGS. 60A-C show the aerosol and its impingement on a screen;

FIGS. 61A-E show deposition of substance on a target;

FIG. 62 shows the effect of operating conditions on plume width;

FIG. 63 shows the effect of repeated activation on pressure;

FIG. 64 shows sleeping score after administration of Midazolam;

FIGS. 65-68 show responses of rats to administration of Midazolam; and

FIGS. 69A-B and 70 show EEG recordings in humans suffering from epileptic seizures before and after treatment.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a device capable of improving the transfer of medicament to a predetermined desired location and to provide a device capable of improving the delivery of medicament through the tissue.

In the present invention, a combination of parameters and forces such as pressure, gas/air volume orifice diameter enable the formation of optimized aerosol characteristics for both improved delivery of aerosol to the target area (such as the olfactory epithelium in the nasal cavity) and enhanced absorption at that area for better delivery to a desired tissue (such as the brain).

The term 'ul' or μm' hereinafter refers to the unit micro liters.

The term 'capsule' or 'container' hereinafter refers to a container configured to contain a flowable substance. The term flowable refers hereinafter to any liquid, gas, aerosol, powder and any combination thereof. It should be emphasized that the term capsule can also refer to a predefined volume within the same in which a flowable substance is placed. In other words, the predefined volume is sized and shaped to enclose a predefined volume of said substance.

The term 'plurality' hereinafter refers to an integer greater than or equal to one.

The term 'olfactory epithelium' hereinafter refers to a specialized epithelial tissue inside the nasal cavity. The olfactory epithelium lies in the upper top portion of the nasal cavity.

The term 'substance' hereinafter refers to any substance capable of flowing. Such a substance can be a granular material, including a powder; a liquid; a gel; a slurry; a suspension; and any combination thereof.

The term 'gas' refers to any fluid that can be readily compressed. Gases as used herein include, but are not limited to, air, nitrogen, oxygen, carbon dioxide, helium, neon, xenon and any combination thereof. Devices charged by hand will typically use air as the carrier gas.

The term 'channel' hereinafter refers to a passageway allowing passage of a fluid through at least a portion of a mixing mechanism. The channel can be disposed within a portion of the mixing mechanism, forming a closed bore; it can be on an exterior of a portion of the mixing mechanism, forming a groove on the portion of the mixing mechanism, and any combination thereof.

The term 'about' refers hereinafter to a range of 25% below or above the referred value.

The term 'biologic' or 'biologic response modifier' hereinafter refers to material manufactured in or extracted from biological sources such as a genetically engineered protein derived from human genes, or a biologically effective combination of such proteins.

All pressures herein are gauge pressures, relative to atmospheric pressure. Pressure units will be written herein using the standard abbreviation for "gauge', namely, "g". For example, atmospheric pressure is 0 barg and a pressure of 1 bar above atmospheric is 1 barg.

The term 'release time' refers hereinafter to the time for the drug and carrier gas to substantially completely exit the device. Typically, the release time is affected by the activation time and reflects the time for the device to reconfigure from the ACTIVE configuration to the INACTIVE configuration or vice versa.

The terms 'the device', 'the present device', 'the SipNose device' and 'SipNose' will be used interchangeably to refer to the device of the present invention.

In all of the embodiments of the device shown hereinbelow, identical numbers refer to identical functions.

All figures shown herein are illustrative and none is to scale.

The present invention teaches a device for delivering a predetermined amount of a substance, preferably comprising a medication or combination of medications, into a body orifice of a subject, the orifice comprising any of the body's natural orifices, including a nostril, the mouth, the ear, the throat, the urethra, the vagina, the rectum and any combination thereof. In preferred embodiments of the device, the device comprises a delivery mechanism and a medicament capsule, as described hereinbelow. The device can apply a broad range of drugs and materials to the nasal cavity for local effect, deliver a broad range of drugs and materials through the nasal cavity to the systemic circulation, deliver a broad range of drugs and materials through the nasal cavity to the central nerve system (CNS) the brain, spinal cord and associated nerves, and any combination thereof.

The drugs to be applied could be, but are not limited to, pharmaceuticals, natural compounds, biologics, hormones, peptides, proteins, viruses, cells, stem cells and any combination thereof.

However, it should be emphasized that the device can be provided alone as well as in combination with a capsule.

In some cases the capsule would be provided with a known medicament within the same and in other cases the capsule would be 'filled' with the medicament just before use.

In some embodiments of the present invention, the device operating characteristics and the substance characteristics can be jointly optimized to maximize uptake of the substance at the desired site. In preferred variants of such embodiments, uptake is further optimized by exploiting synergies between delivery characteristics generated by the device and by the formulation or composition of the delivered material In some embodiments, the substance comprises one or more agents to optimize delivery through the mucosal membrane by means of mucoadhesive agent and/or a permeability enhancer agent and/or a particulate formulation in the nano-particle or macro-particle range, and any combination thereof. In such embodiments, the combination of the device and substance enhance the delivery of the active agent to the target area (nasal epithelium and more specifically olfactory epithelium) and from there to the target tissue (for example the brain).

A non-limiting example is a composition comprising a drug to be delivered and at least one chemical permeation enhancer (CPE). In a preferred embodiment, the composition contains two or more CPEs which, by using a nasal delivery device, affect in an additive manner or behave synergistically to increase the permeability of the epithelium, while providing an acceptably low level of cytotoxicity to the cells. The concentration of the one or more CPEs is selected to provide the greatest amount of overall potential (OP). Additionally, the CPEs are selected based on the treatment. CPEs that behave primarily by transcellular transport are preferred for delivering drugs into epithelial cells. CPEs that behave primarily by paracellular transport are preferred for delivering drugs through epithelial cells. Also provided herein are mucoadhesive agents that enable the extension of the exposure period of the target tissue/mucus membrane to the active agent, for the enhancement of delivery of the active agent to and through the mucus membrane.

In contrast to prior-art nasal delivery devices and technologies, the devices of the present invention can produce a fine aerosol in the nasal cavity or other desired body orifice at the target area and at the location of the target tissue instead of producing the aerosol only within the device or immediately after exit from the device. Utilizing the pressure as a driving force and the air as a carrier allows the material to be released from the nozzle as a mixture of aerosol and a pre-aerosolized state. The properties of the resultant aerosol are typically dependent on the properties of the device and of the medium into which the device is discharged. The properties of the device which affect the aerosol characteristics are the delivery pressure, the volume of the delivery gas, the characteristics of its orifice and time to activate.

In some embodiments, the aerosol properties are fairly independent of the delivered substance, while, in other embodiments, the pressure, volume, orifice characteristics, and delivered substance properties can be co-optimized.

In prior-art devices the aerosol is produced in proximity exit of the device. Typically, the aerosol comprises a wide "fan" of aerosol and a low driving force. Therefore, large droplets typically deposit very close to the exit from the device, while smaller droplets tend to quickly contact the walls of the passage, so that deposition is typically predominantly close to the delivery end of the device, with little of the substance reaching desired sites deeper in the body orifice, such as the middle and superior turbinates of the nose.

In contrast, in the present device, the pre-aerosolized mixture of gas and substance exits the device with a significant driving force as a mixture of aerosol and pre-aerolized material (fluid or powder). When the preaerosolized material hits the walls of the nasal passages, it "explodes" into a fine aerosol that is capable of being driven by the pressure deep into the nasal passages to deposit in the desired region.

FIGS. 1A-D illustrate capsules of prior art intended to deliver medicaments to the nasal passages. FIG. 1A illustrates the LMA MAD nasal atomizer from Wolfe Tory, FIG. 1B illustrates a typical nasal pump, FIG. 1C illustrates a Simply Saline nasal spray, and FIG. 1D illustrates the Optinose breath powered delivery device.

Typical prior art devices release aerosolized medicament. However, all have severe limitations.

The LMA MAD nasal atomizer (FIG. 1A) comprises a syringe, so the dose size can be quite accurate, if the user is careful. However, the delivery pressure is provided by the user depressing a plunger, so that control of delivery speed and delivery pressure (and the droplet size) depend on how hard the user depresses the plunger, making these parameters hard to control. Furthermore, syringe plungers are subject to stick-slip behavior, especially at the start of depression, making the delivery parameter harder to control accurately.

Devices such as nasal pumps (FIG. 1B) typically do not provide a fixed dose per activation, as the delivery energy is provided by pressure exerted by a user during activation. Typically, there is a wide dispersion in the size of the droplets produced following user activation, making it difficult to accurately target the medicament to a desired location.

The Simply Saline Nasal Mist (FIG. 1C) comprises a pressurized container. A button is pressed to release a portion of the contents. Each activation reduces the pressure inside the container, thereby reducing the velocity and pressure of delivery and altering the droplet size. The length of activation time depends on the time the button remains depressed, so that there is little control of the amount delivered.

The Optinose breath powered delivery device (FIG. 1D) is breath-powered. It uses a capsule containing a single dose of the medicament, so dose size is well-controlled. However, delivery speed and delivery pressure (and the particulates dispersion) depend on how hard the user exhales into the device and how long the user continues to exhale. Furthermore, exhalation pressures are typically higher at the start of exhalation than at the end, so the delivery parameters will vary during delivery.

Unlike the device of the present invention, none of the prior-art devices provide accurate control of all of the delivery parameters, which include dose volume, carrier volume, pressure, and delivery velocity.

A further advantage of the device of the present invention (the SipNose device) is that, unlike the prior art devices, it can be configured to accurately deliver large volumes (>100 ul) at high pressure, such that the high-velocity aerosol can be as reliably and reproducibly produced for large volumes as for small.

Figure 2:
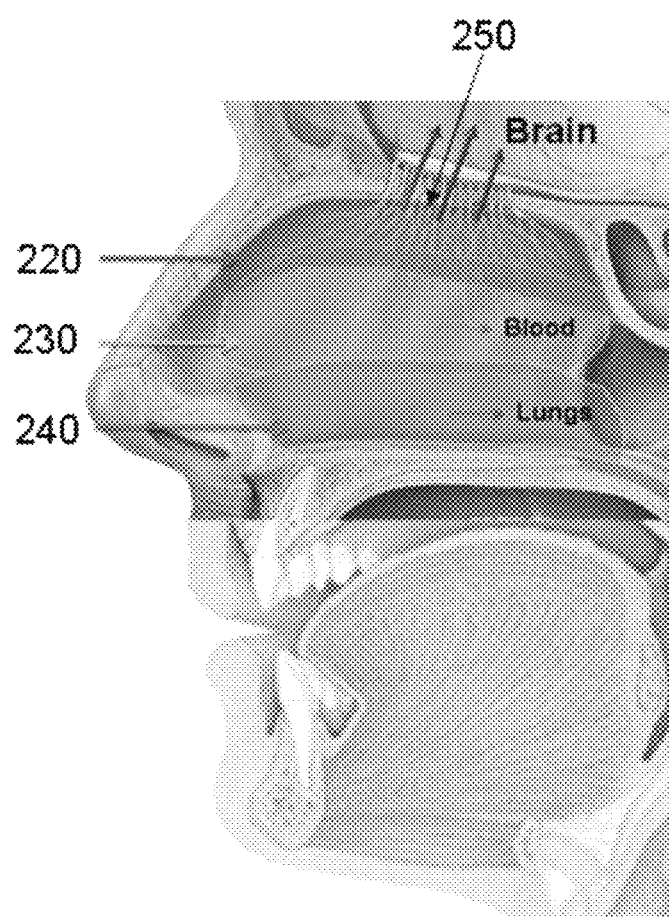

FIG. 2 illustrates locations for deposition of substances entering the nostrils. Typical locations are (a) deposition in the lungs after passage through the lower turbinates (240), thereby enabling transfer of the substance across the walls of the alveoli of the lungs; (b) deposition in the mucous membranes lining the nasal passages, especially the lower (240), and middle (230) turbinates, facilitating transfer of the substance to the blood; and (c) deposition in the olfactory epithelium mucous membranes of the upper turbinates (220) facilitating transfer, via the thin ethmoid bone (not shown) to the brain through the olfactory nerve endings (250) substance, typically as an aerosol, with the mixture of gas and substance entering the body orifice via the delivery end. Typically, discharge (delivery) time is less than about 500 ms.

The embodiments disclosed below disclose non-limiting examples of devices and methods for providing the predetermined volume of gas at the predetermined pressure.

Figure 3:
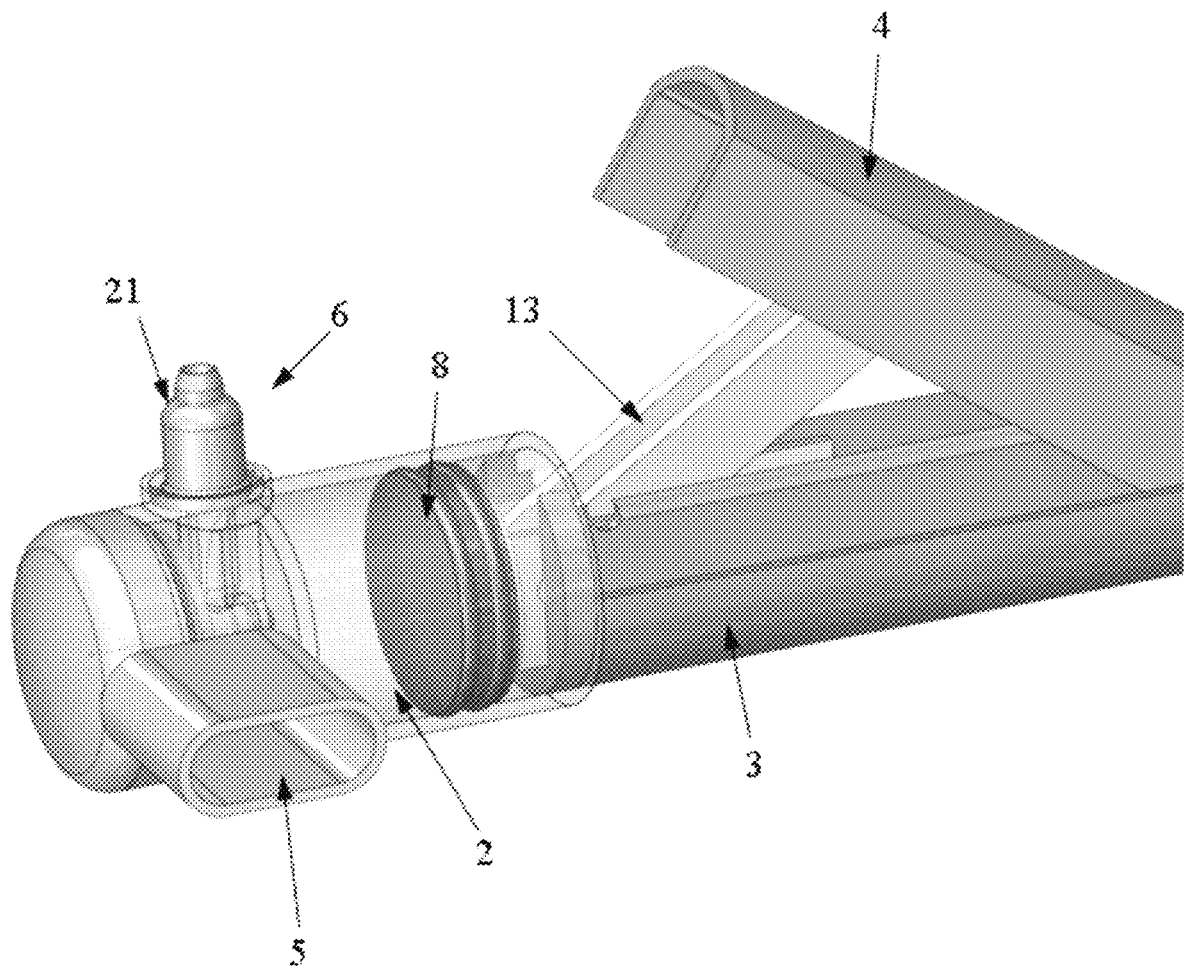

FIG. 3 shows an exemplary embodiment of the device. In the embodiment of FIG. 3, a piston (8) is used to compress the gas. The piston is moved by a lever (4) attached to the piston (8) by a rotatable connector (13). The piston (8) fits air-tightly and slidably in the air chamber (2). The lever (4) is rotatably attached to the handle (3) at its proximal end such that the distal end of the lever (4) can be pulled away from the handle (3) to retract the piston (8) toward the proximal end of the device and pull air into the air chamber (2) and the distal end of the lever (4) can be pushed toward from the handle (3) to extend the piston (8) toward the distal end of the device and compress the gas. In use, the mouthpiece (5) is placed in the mouth and the nosepiece (6) is placed in a nostril. Inhaling on the mouthpiece (5) activates the device (mechanism not shown), releasing the compressed gas from the air chamber (2), from whence it passes through the substance capsule (21) and exits the device through the distal end of the nosepiece (6).

The embodiments disclosed in FIG. 3 are typically configurable into four states: (a) a non-activated state where the valve is in its INACTIVE CONFIGURATION, the chamber contains non-pressurized gas, and the portion of the chamber in fluid connection with the valve is at a minimum, (b) a pre-activated state where the valve is in its INACTIVE CONFIGURATION, the chamber contains non-pressurized gas, and the portion of the chamber in fluid connection with the valve is at a maximum, in this stage the tip to be entered to the body orifice (the delivery end) can be under "vacuum" conditions or not, (c) a loaded configuration where the chamber contains a predetermined amount of pressurized gas and the valve is in its INACTIVE state, and (d) an activated state where the valve is in its ACTIVE state. Typically, the activated state discharges the device, with the mixture of gas and substance released from the device, entering the body orifice via the delivery end.

The characteristics of the aerosol, namely its size, shape and velocity, depend on the speed of exit of the gas from the chamber, the volume of air delivered, the characteristics of the delivery orifice and the activation time. The speed of exit of the gas from the chamber and the volume of air delivered depend on the pressure of the gas in the chamber in the loaded state, on the volume of the chamber in the loaded state, and on the characteristics of the fluid connection between the chamber and the delivery orifice. The less change there is in these characteristics during an activation and between activations, the more reliable and the more reproducible the device will be. Therefore, in controlling the characteristics of the fluid connection, the time taken to open the valve needs to be taken into consideration. In devices of the current invention, the valve opening times are both reproducible and short and are not in any way dependent on the user, so that the delivery comprises a short, reproducible, high velocity pulse of the gas.

The non-activated state and the loaded state appear identical; they differ in that, in the loaded state the chamber contains pressurized gas whereas, in the non-activated state, the chamber does not contain pressurized gas.

In some embodiments, including embodiments intended for use in emergencies or daily home use, the device is a single-use device with only two states, a loaded state and an activated state. The device is provided in the loaded state; activation of the trigger mechanism discharges the gas and substance.

In other embodiments, the device is provided in the pre-activated state. The user transforms the device into the loaded state, pressurizing the gas, and activates the trigger mechanism to discharge the gas and substance.

Capsules can be single-compartment or multi-compartment. Single-compartment capsules can comprise a flexible silicone tube, preferably sealed at both ends.

Multi-compartment capsules can contain different components of a substance in the different compartments; at least one compartment can contain a carrier gas, and any combination thereof.

In some embodiments, there is a single capsule for the carrier gas and the substance. Some embodiments have separate capsules for substance and gas.

Some embodiments have the gas held in a gas holding chamber. The gas holding chamber can be filled at the time of manufacture or can be filled to the predetermined pressure by a charging mechanism.

Some embodiments have the substance held in a holding chamber. The holding chamber can be filled at the time of manufacture or can be filled by a filling mechanism such as, but not limited to, a syringe.

It should be emphasized that the present invention refers to both one compartment capsules as well as multi-compartment capsules.

FIG. 4A-E shows exemplary embodiments of multi-compartment capsules.

In multi-compartment capsules, walls divide the capsule into compartments. The compartments can have approximately the same volume or different volumes, and the same thickness or different thicknesses; if circular, they can have the same diameter or different diameters. They can have the same area at the end faces, or different areas.

The compartments, taken together, can form a large fraction of the volume of the capsule, or they can form a small fraction of the volume of the capsule.

Compartment walls can be equally spaced, either angularly or linearly, or they can be unequally spaced. Spacings can be arbitrary, they can be regular, they can follow a pattern, and any combination thereof.

Compartments can be near the edge of the capsule or at other positions within the capsule.

Before use, the compartments are preferably hermetically sealed to prevent mixing of the substances contained therein.

Compartment walls can be substantially similar in shape to the capsule walls (for non-limiting example, lenticular walls within a lenticular capsule) or at least one of the compartments' walls' shape differs from the shape of the cross-section of the capsule. (For non-limiting example, a lenticular wall within a circular capsule.)

Compartment walls can be non-frangible or frangible. Frangible walls permit mixing or reaction of the contents of adjacent compartments before the substances leave the compartments.

Compartments can, but need not, have a frangible membrane at at least one end.

Any compartments can contain one substance or a mixture of substances; any two compartments can contain the same substance or mixture thereof, or different substances or mixtures thereof.

The material of any combination of capsule walls and compartment walls can be rigid, semi-flexible, flexible and any combination thereof. Flexible or semi-flexible compartment or capsule walls can reduce dead space—regions of low gas flow—in the air path during activation.

Figure 4A:
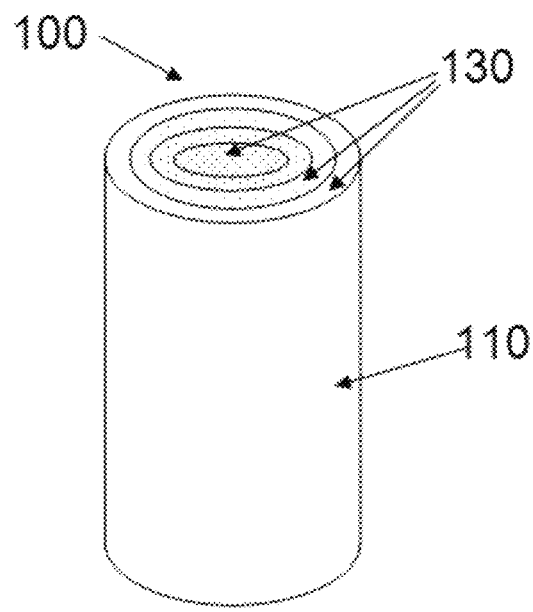

In the embodiment shown in FIG. 4A, the compartments (130) are coaxially disposed within the outer tegument (110), with the compartments nested within one another. The central compartment forms a cylinder and the remaining compartments, three in the exemplary embodiment of FIG. 4A, each forming an annulus of a cylinder. Nested compartments need not be coaxial.

Figure 4B:
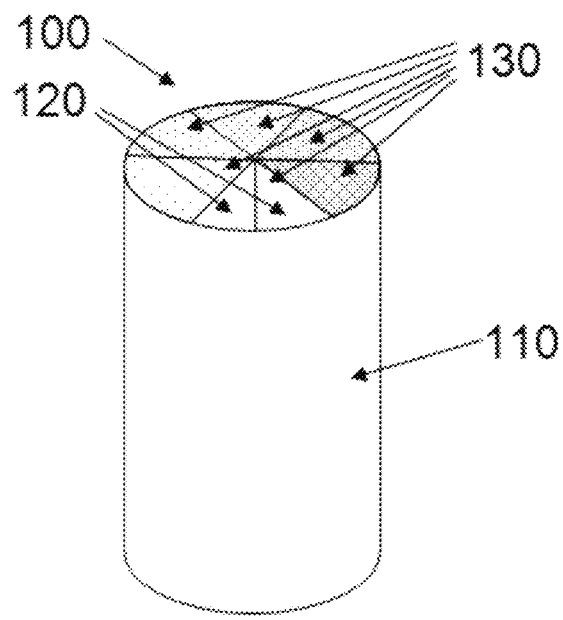

In the embodiment schematically illustrated in FIG. 4B, the capsule (100) comprises an outer tegument (110) enclosing n angularly disposed compartments (130) separated by walls (120), where n is less than about 10. In the embodiment shown in FIG. 4B, n is e.g., six.

Figure 4C:
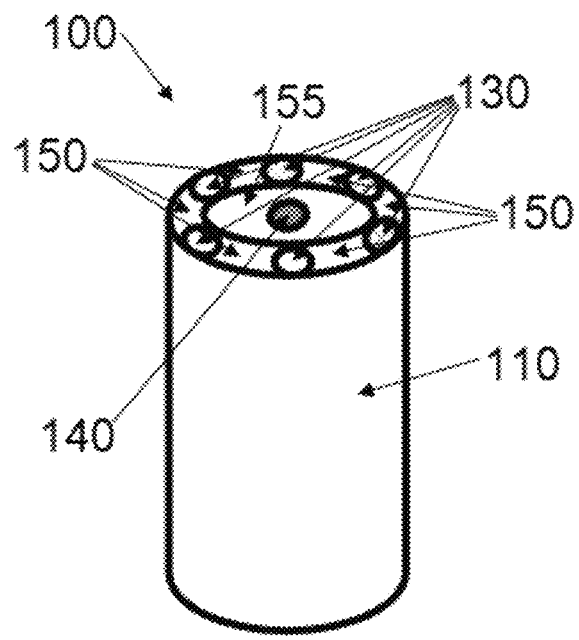

In the embodiment schematically illustrated in FIG. 4C, the capsule (100) comprises an outer tegument (110) enclosing six angularly disposed cylindrical compartments near the edge of the capsule (130), a central compartment (140), and auxiliary compartments (150, 155), for a total of 14 compartments.

In practice, the embodiment illustrated in FIG. 4C will have no more than about 20 compartments.

In some embodiments, there is no central compartment (140).

In the exemplary embodiment shown, the auxiliary compartments are hollow, containing a substance. In other embodiments, at least one of the auxiliary compartments (150, 155) is comprised of solid material, thereby forming part of the structure of the capsule.

In preferred embodiments, the central compartment (140) and the central auxiliary compartment (155) are solid, forming a solid central core for the structure. The remaining compartments (130, 150) comprise substance, where, in preferred embodiments, the compartments (130) contain a substance such as a medicament and the auxiliary compartments (150) contain a propellant, preferably compressed gas.

Figure 4D:
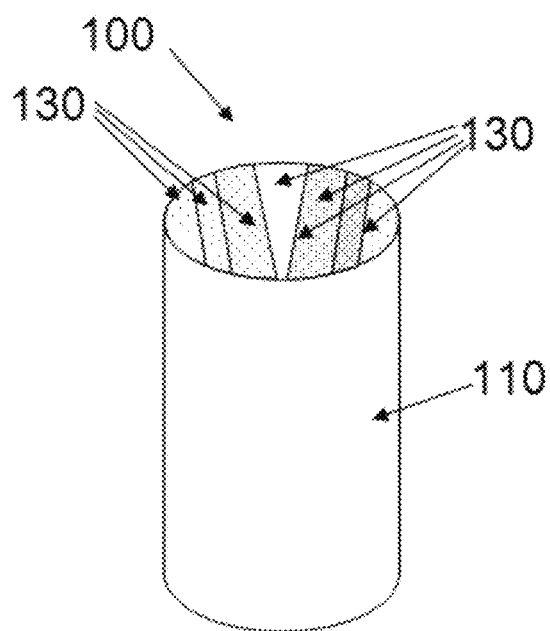

In the exemplary embodiment shown in FIG. 4D, the compartments (130) form slices within the outer tegument (110). In the exemplary embodiment of FIG. 4D, some of the slices have parallel sides, while the central slice is wedge-shaped; in other embodiments, all of slices have substantially parallel sides. In yet other embodiments, a plurality of slices are wedge-shaped. Slice-type capsules can have up to about 10 compartments.

Figure 4E:
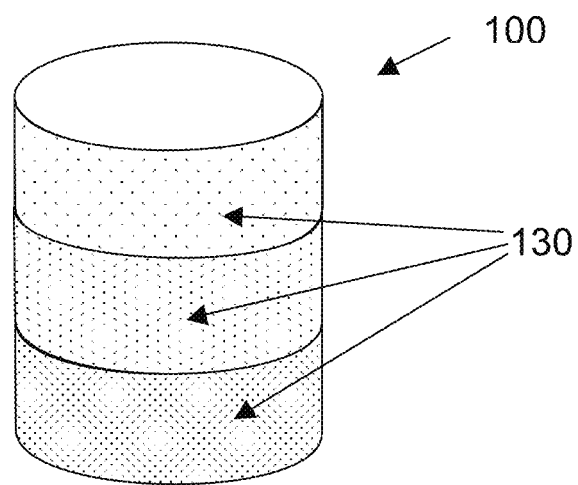

In the exemplary embodiment shown in FIG. 4E, the compartments (130) are arranged longitudinally, with the walls between the segments being frangible. Any number of such compartments can be used and the lengths of the compartments can differ.

These embodiments are merely exemplary; any combination of the above arrangements can be used.

In the exemplary embodiments shown, the walls separating the compartments are planar. In other embodiments, the walls can form a curve, either regular or irregularly shaped.

The main longitudinal axis of at least one of the compartments can be parallel to the main longitudinal axis of the capsule, it can be spirally disposed it can be at an angle to the main longitudinal axis of the capsule, and any combination thereof.

The main longitudinal axes of the compartments can be straight, they can form regular curve, they can form irregular curves, and any combination thereof. For any pair of compartments, the main longitudinal axes can be the same or they can be different.

In most embodiments, at least part of the upstream closure surface (not shown) and the downstream closure surface (not shown) of the capsule are frangible or otherwise removable, such that, when broken or otherwise removed, the medications can be delivered to the desired deposition site. In a variant of these embodiments, different portions at least one closure surface have different breaking strengths, such that the different portions can be broken at different times during delivery of the medication, enabling either differential mixing of medical formulations in different compartments or differential delivery of the medications in at least two of the compartments.

In some embodiments, at least part of the side surface of the capsule is frangible, enabling yet another mixing path or delivery path.

Capsules can be cylindrical with circular cross-section, as shown, cylindrical with oval, elliptical, lenticular, or polygonal cross-section, with the polygon having at least three sides and not more than about 20 sides. The polygon can be a regular or irregular.

Capsules can be spherical, elliptical, ovoid, pillow-shaped, football-shaped, stellate and any combination thereof. Capsules can form regular or irregular shapes.

Compartments can have substantially constant cross-section through the device or the cross-section can vary in area, in shape, or in any combination thereof.

Figure 5:
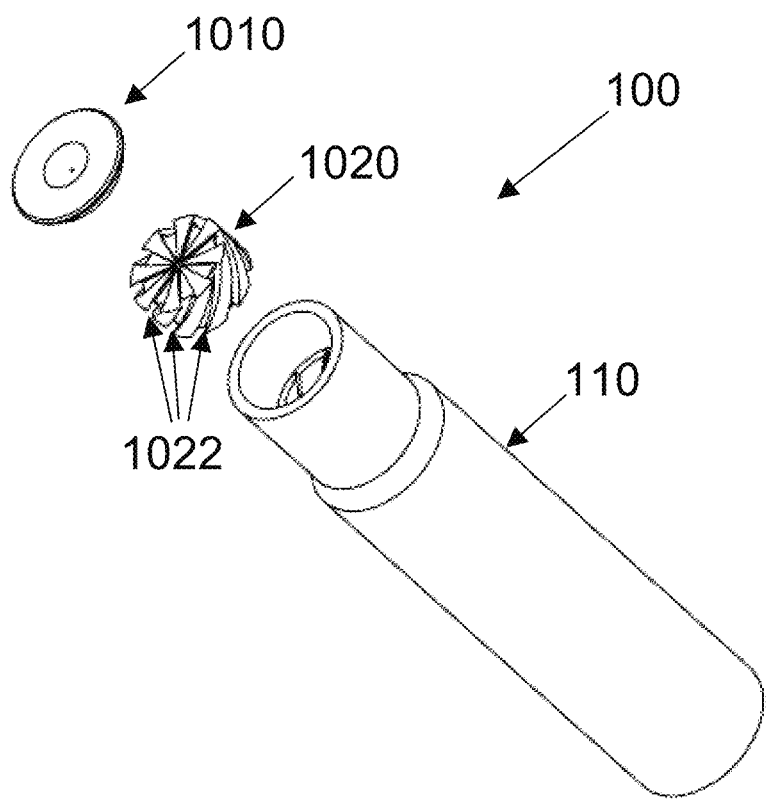

FIG. 5 shows a schematic of an exploded view of an exemplary embodiment of a mixing chamber in a capsule, the part of a capsule configured to mix components in a composition. In this exemplary embodiment, the tegument (110) of the capsule and the upstream closure surface (1010) of the capsule are shown. Also shown is a mixing mechanism (1020), in this case, a single-section mechanism. The substance compartments are not shown.

In this exemplary embodiment, the mixing mechanism (1020) comprises spirally-disposed air channels (1022) at the periphery of the mixing mechanism (1020). The central part of the mixing mechanism (1020) is solid, forcing the carrier gas and the substances to pass through the channels (1022). By narrowing the channel through which the gas passes and by changing the direction of the gas flow, mixing of the substances is enhanced. The mixing mechanism (1020) fits within the tegument (110) of the capsule (100) and mixing occurs within the capsule (100).

In some embodiments, a single channel is used. This can have a cross-section which is annular, circular, polygonal, lenticular, pie-shaped irregular, or any combination thereof. The channel main longitudinal axis can pass through any part of the capsule. Non-limiting examples include a circular cross-section with main longitudinal axis at the capsule center, and an annular cross-section at the periphery of the capsule, with main longitudinal axis at the capsule center.

In some embodiments, the capsule comprises two units, one comprising at least one substance and one comprising the mixing mechanism, such that the substances exit the compartments and are then mixed in the mixing mechanism.

In other embodiments, the mixing mechanism (1020) comprises channels disposed throughout its cross-section.

Channels can be arbitrarily arranged across a cross-section, regularly arranged across a cross-section, or irregularly arranged across a cross-section.

Channels can be linearly disposed, parallel to the main longitudinal axis of the capsule; or linear and disposed at an angle to the main longitudinal axis of the capsule.

The main longitudinal axis of at least one channel can be curved with respect to the main longitudinal axis of the mixing mechanism, with respect to an axis perpendicular to the main longitudinal axes, or any combination thereof.

Any combination of the above channel shapes can be used.

The shape of a channel cross-section can be substantially the same along the length of the channel, the shape can change along the length of the channel, the size of the cross-section can change along the length of the channel, and any combination thereof.

Shapes of the cross-sections of the channels can vary in the same manner along the length of the channel, or they can vary in different manners.

Shapes of the cross-sections of the channels can be the same for all the channels, or the shapes of the cross-sections of at least two channels can be different.

Sizes of the cross-sections of the channels can vary in the same manner along the length of the channel, or they can vary in different manners.

Sizes of the cross-sections of the channels can be the same for all the channels, or the sizes of the cross-sections of at least two channels can be different.

In some embodiments, the mixing mechanism (1020) comprises a plurality of longitudinal sections, with the sections having fluidly connected channels, but the channels are differently disposed longitudinally. For non-limiting example, a two-section device can have spirally disposed channels with left-handed spirals in the first section and right-handed spirals in the second section.

In some embodiments, there are different numbers of channels in the two sections. In other embodiments, there are the same number of channels in the two sections.

In other multi-section mixing mechanisms (1020), sections comprising channels are fluidly connected by substantially channel-free regions.

Mixing mechanisms can comprise between 1 and 10 regions. Individual regions can have any of the channel dispositions described hereinabove.

In some embodiments, mixing can be done by an integral mixing mechanism, either a single-section or a multi-section device. In other embodiments, mixing can be done by disposing a plurality of single-section mechanisms end-to-end, either abutting each other or with spacers to provide channel-free regions.

During the process of mixing, the first and second flowable substances can be mechanically mixed with each other and with the air or other gas, they can be reacted with each other, and any combination thereof.

In some embodiments, reaction of at least one flowable substance can be enhanced by a catalyst deposited on or part of the walls of the mixing region.

Criteria of the capsule, whether single-compartment or multi-compartment, can be optimized to include: ensuring that a single dose of the substance is delivered in its entirety, ensuring that the single dose contains the predetermined amount of the substance, ensuring that the dose is delivered to the desired region of the nose, and ensuring that delivery of the dose causes the minimum possible discomfort to the patient. Any combination of these criteria can be optimized for each particular combination giving rise to a different embodiment of the capsule.

The capsule can also be optimized for ease of insertion into a delivery device, for ease of removal from a delivery device, for stability of the contents during storage, for resistance of the capsule materials to environmental degradation, for resistance to undesired fracture, for reliability of use, for completeness of mixing, for completeness of reaction, and any combination thereof.

In some embodiments, the capsule comprises a filter configured to remove from the air at least one selected from a group consisting of particles, particulates, bacteria, viruses, moisture, and undesired gases before the air contacts the user. Such a filter, by preventing unpleasant odors or tastes from reaching the user and by preventing particles or particulates from reaching the user, can make the experience of using the device much more pleasant for the user and much safer. By removing bacteria and viruses, infection of the user can be prevented.

In some embodiments, the capsule contains only a single dose of the substance, the capsule being replaced after each use. In other embodiments, the capsule contains multiple doses of the substance, preferably packed separately, so that the dose is fresh for each use.

During dispensing of the substance, the gas passing through the capsule entrains the substances contained within the compartments such that the substances have a predetermined distribution within the dispensed mixture, where the predetermined distribution can be a homogeneous distribution or a heterogeneous distribution. Heterogeneous distributions can be: an arbitrary distribution, a distribution in which the dispersion of the at least one substance within the mixture follows a predetermined pattern, and any combination thereof.

According to another embodiment of the present invention, movement of air into the chamber during transformation of the device into said pre-activated state creates a vacuum in the region near or in the capsule.

Figure 7A:
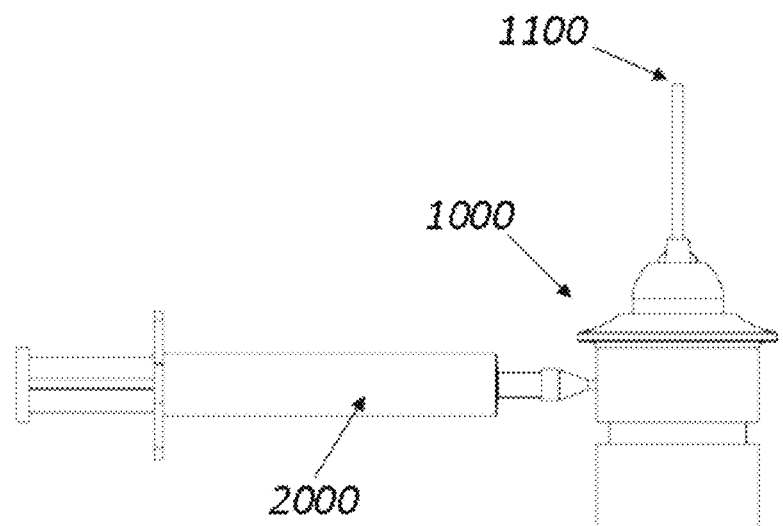
Figure 7B:
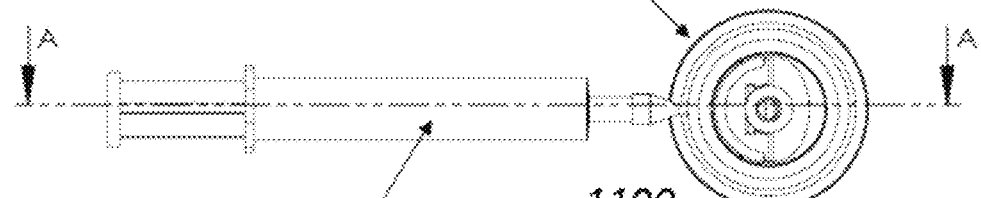
Figure 7C:
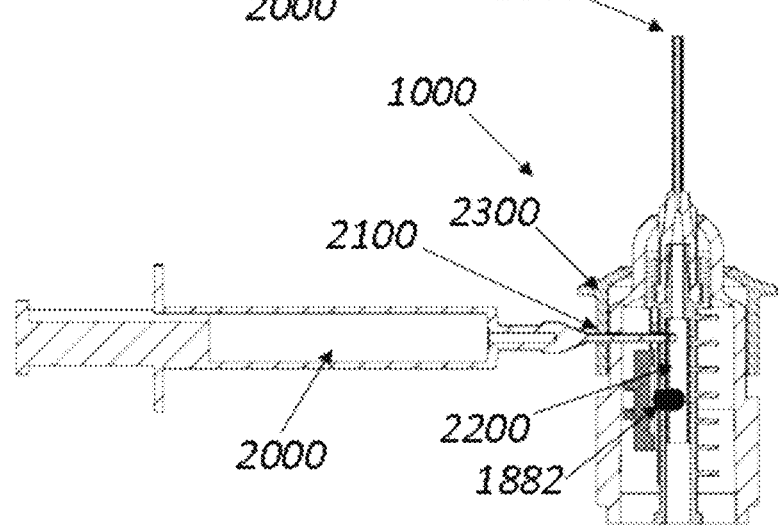

FIGS. 6-7 show exemplary embodiments of the loading and triggering region of embodiments of devices with mechanical triggering mechanisms, all of which are configured to open fully, quickly and reproducibly, with the time over which the valve opens being reproducible, independent of how the user may operate the device. For example, in the suction devices described herein, a weak suction will induce the same full opening over the same time period as a strong suction, and, in the mechanical devices disclosed herein a slow activation of the triggering mechanism will induce the same full opening over the same time period as a rapid activation of the triggering mechanism.

In some embodiments, the loading region of the device comprises at least one filter to remove from the air (or other gas) at least one selected from a group consisting of particles, particulates, bacteria, viruses, moisture, and undesired gases before the air contacts the user.

Preferably, the air or gas is filtered on entrance to the air chamber from the outer environment (the room, the surrounding area). Alternatively or additionally, air can be filtered on exit from the air chamber, while within the loading air chamber, and any combination thereof.

FIG. 6A-D shows a preferred embodiment of the loading portion of the device (1000) with a pinch triggering mechanism. FIG. 6A shows a side view of the device, FIG. 6B shows a cross-section, taken along the line AA in FIG. 6A, FIG. 6C shows an exploded view, and FIG. 6D shows a perspective view.

The device comprises a hollow upstream portion (1881) fluid-tightly connected to a hollow downstream portion (1889). In this embodiment, the activation mechanism (1880) comprises a cup-shaped insert (1884) fitting snugly and fluid-tightly within the hollow interior of the device. The outer rim of the insert (1884) is preferably fixed to the outer wall of the activation mechanism (1880), with its inner rim (1885) able to slide on an inner wall (1886), preferably tubular, of the activation mechanism (1880). In the activation mechanism's (1880) closed position, a stop (1882) is firmly held by the inner rim (1885) of the insert.

The inner wall of the activation mechanism (1880) comprises a throughgoing bore (1883). In some variants of this embodiment, a flexible tube (1888) is fluid-tightly fixed to the wall (1886) such that there is flexible tubing in at least the portion of the wall abutting the stop (1882). In other variants of this embodiment, the flexible tube (1888) passes through the bore (1883).

In preferred variants of this embodiment of an activation mechanism, in the closed position, the stop (1882) fits into and sits in a hole in the inner wall (1886). In other variants, the stop (1882) fits into and sits in a depression in the inner wall (1886).

When the activation mechanism (1880) is in the closed position, the flexible tube (1888) is pinched between the stop (1882) and the inner side of the throughgoing bore (1883).

When the activation mechanism (1880) is activated, the insert (1884) slides up along the wall, releasing the stop (1882) so that the pinched region in the flexible tube (1888) is released, thereby releasing the pressurized gas and dispensing the substance.

In the embodiment shown in FIG. 6, the activation mechanism can be activated either by sucking on the suction mechanism (1810), creating a partial vacuum above the cup-shaped insert (1884) and pulling it upward, thereby releasing the stop (1882), or by pressing the pressable lever (1870). Pressing the pressable lever (1870) forces it inward so that the ramp portion (1782) of the pressable lever pushes the cup-shaped insert (1884) upward, thereby releasing the stop (1882), releasing the pressurized gas and dispensing the substance.

In some embodiments, flexible filling material such as, but not limited to, flexible tubing, can be placed within the region of the device (not shown) containing the substance to be delivered in order to reduce dead space within the device. Reducing dead space will not affect the characteristics of the aerosol formed after release, but it will decrease pressure loss and increase air speed within the device, thereby substantially reducing residual substance remaining within the device after completion of activation, either within the capsule or adhering to the interior walls of the device, e.g., within the nozzle. It is well known in the art that residual material within a delivery device can be released on subsequent uses of the device and that the amount of such residual material released during a given use of a device is extremely variable. Therefore, minimizing residual substance within the device will increase the accuracy and reproducibility of delivery, thereby increasing its repeatability and reliability, both by maximizing the fraction of the substance actually delivered from the current capsule and by minimizing the amount of residual substance on the walls of the device.

It should be noted that the capsules (disclosed hereinbelow) are designed so as to avoid residual volume within the capsule itself, since, even in the case of a single dose or disposable capsule there are safety issues involved in disposing of capsules containing residual amounts of hazardous drugs or other hazardous component in the composition.

Other trigger mechanisms include, but are not limited to, a releasable catch, a pressable button a detectable predetermined sound pattern, a detectable predetermined light pattern, a moveable lever, a slider moveable from a first position to a second position, a rotatable knob is rotated, a releasable latch configured and any combination thereof.

The predetermined sound pattern can be: a constant-pitch sound, a varying-pitch sound, a constant volume sound, a varying volume sound and any combination thereof.

The predetermined light pattern can be: a constant-color light, a varying-color light, a constant brightness light, a varying brightness light and any combination thereof.

In some embodiments, the device comprises a unidirectional valve such that gas can flow from the charging mechanism to the delivery end, but is unable to flow in the reverse direction.

In some embodiments, a substance to be dispensed (which can comprise any number of materials) can be stored within a capsule, either as the substance to be dispensed or as a precursor or precursors, with the capsule placeable within the device, as described hereinbelow. In such embodiments, the capsule is ruptured during activation, either all at once or in stages, thereby dispensing the substance.

In other embodiments, a substance, prepared in a conventional matter, is introducible into a holding chamber within the device and, on activation of the device, the substance is dispensed. Embodiments of this kind can be used as emergency dispensing devices, since any flowable substance can be introduced into the holding chamber and since the holding chamber, which has no facilities for separating precursors or for providing an inert atmosphere in the chamber, is not intended for long-term storage of substances.

In some embodiments, the capsule chamber in which the capsule can be placed can also function as a holding chamber, so that the substance can be dispensed either from the capsule or directly from the holding chamber.

In other embodiments, an insert can be placed within the capsule chamber, with the interior of the insert being a holding chamber.

An embodiment of the activation mechanism a dispensing device (1000) into which any flowable substance is introducible is shown in FIG. 7A-C. The charging mechanism is not shown. FIG. 7A shows a side view of the embodiment, FIG. 7B shows a top view of the embodiment, and FIG. 7C shows a cross-section, taken along the line AA in FIG. 7B.

In this embodiment, the means of loading the substance into the device is a syringe (2000). The syringe (2000) can be placed in the injection port (2100, FIG. 7C) and the syringe plunger depressed so that the flowable substance enters a dispensing chamber (2200) within the device (1000). Before, during or after injection of the substance into the chamber, the device can be charged, in any manner described herein, using any activation mechanism described herein or known in the art.

In some embodiments, the syringe is left in the injection port. In other embodiments, a cover (2300) is provided for the injection port, so that, after loading the substance into the chamber, the injection port can be sealed by means of the cover. As shown in the embodiment of FIG. 7, the cover (2300) can slide longitudinally onto and off the injection port (2100), In other embodiments, it can rotate or spiral around the device to cover or uncover the injection port (2100), it can rotate around a hinge on the body of the device so that it flips onto and off the injection port (2100), or any other method of sealing the port can be used. In the embodiment as shown, in the open position, the syringe goes through a hole in the cover in order to reach the chamber. Any combination of the above embodiments can be used in a cover.

In some embodiments, the substance is stored in a capsule or in a sealed compartment in the device. Before or during activation, the capsule or sealed compartment is breached and pressure on the capsule (e.g., by pressing a button to move the piston of a built-in syringe) forces the contents into a dispensing chamber (2200). Dispensing gas passing through the dispensing chamber (2200) then entrains the substance and delivers it.

In some embodiments of a device with separate storage chamber and holding chamber, the capsule comprises a syringe or a syringe like compartment, a rubber piston and seals. The longitudinal axis of the syringe and piston are at right angles to the longitudinal axis of the device. Pressure on the piston moves the substance from the syringe into the holding chamber, in a manner similar to the syringe (2000) and holding chamber (2200) in FIG. 7.

In the embodiment shown, a pinch triggering mechanism is used, as shown hereinabove in FIG. 6, although any of the other activation mechanisms described herein or any conventional valve known in the art can be used.

In reference to FIGS. 7-9, three exemplary embodiments of nozzles (1100) are shown. In both FIG. 8 and FIG. 9, the nozzle (1100) has a tip extension (1110) with a larger diameter than the nozzle, the tip extension substantially surrounding the distal end of the nozzle (1100). In FIG. 7, the nozzle tip is substantially conical, lacking the optional tip extension (1110).

Figures 8A, 8B, 8C, 8D:
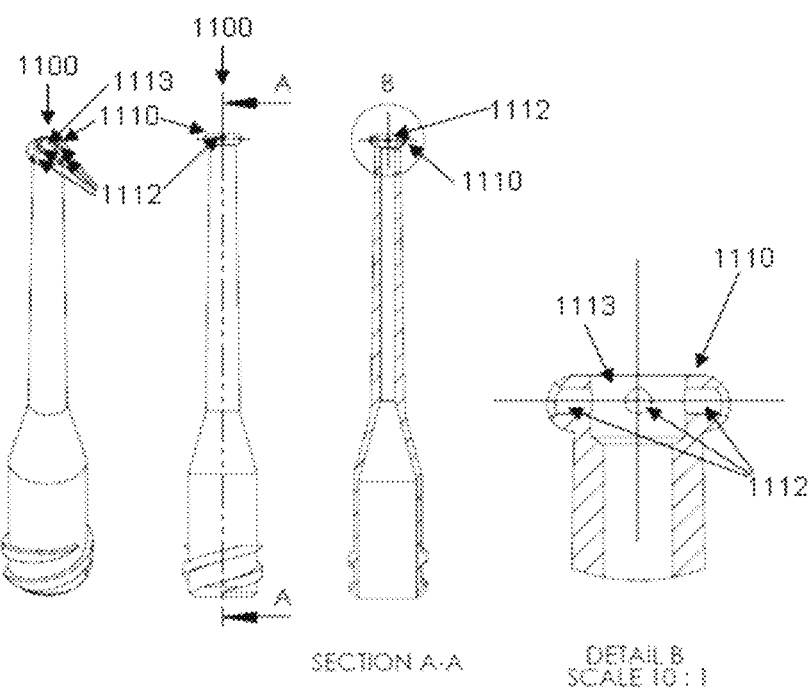

In the exemplary embodiment of both FIG. 8 and FIG. 9, the tip extension (1110) has holes (1112) in it to allow substance to exit laterally from the extension, and the tip (1110) has at least one hole (1113) in its distal end to allow substance to exit longitudinally from the nozzle (1100). FIG. 8A-D shows an embodiment of a nozzle (1100) with a tip extension (1110). FIG. 8A shows a perspective view of the nozzle (1100) from the distal end, while FIG. 8B shows a side view. FIG. 8C shows a cross-section of the nozzle along the line AA in FIG. 8A, while FIG. 8D shows an enlarged view of the circled region B at the tip of the nozzle in FIG. 8C, showing the tip of the nozzle and the tip extension in more detail. The holes (1112) in the tip extension (1110) and the hole (1113) in the tip can be clearly seen. In some embodiments, the nozzle (1110) has only lateral holes (1112), so that no substance escapes from the distal end of the nozzle (1110).

In preferred embodiments, the distal end of the tip extension does not comprise any longitudinal protruberances, being substantially flat in the area around the opening (1113) and, where non-planar, extending proximally from the plane of the opening.

Figures 9A, 9B, 9C, 9D:
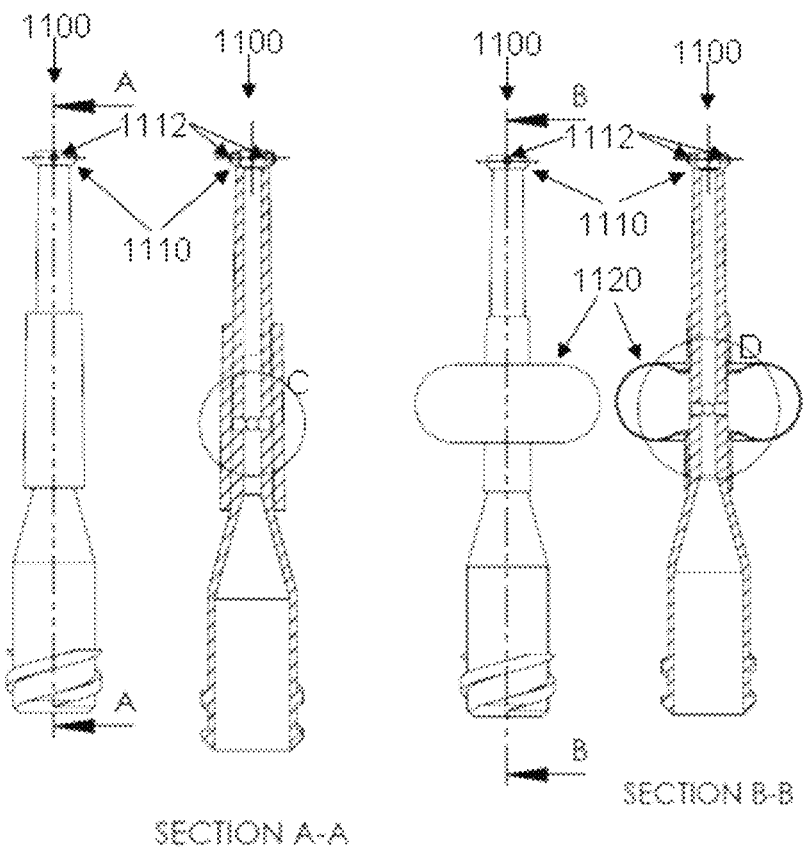
Figures 9E, 9F, 9G, 9H:
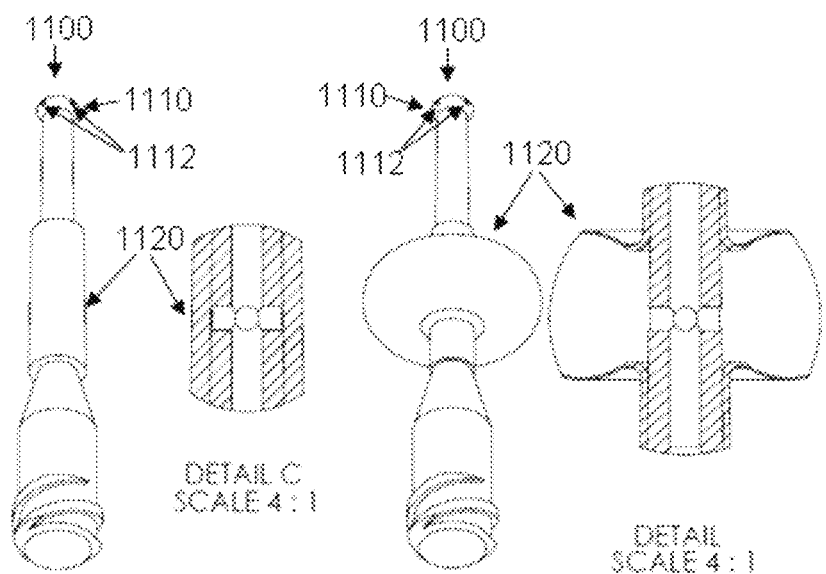

In order to prevent material from escaping from the nasal passages or entering undesired areas in the nasal cavity, in some embodiments, the nozzle comprises a medial extension, an expandable portion (1120). FIG. 9 shows an embodiment of a nozzle with a tip extension (1110) and an expandable portion (1120). FIGS. 9E and 9G show perspective views of the nozzle from the proximal end, while FIGS. 9A and 9C show side views of the nozzle (1100). FIGS. 9B and 9D show cross-sections of the nozzle (1100) along the lines AA in FIG. 9A and BB in FIG. 9C, respectively. FIG. 9F shows an enlarged view of the circled region C in the center of the nozzle in FIG. 9B, while FIG. 9H shows an enlarged view of the circled region D in the center of the nozzle in FIG. 9D.

FIGS. 9A, 9B, 9E and 9F show the nozzle with unexpanded expandable portion, while FIGS. 9C, 9D, 9G and 9H show the nozzle with expanded expandable portion.

In the exemplary embodiments of FIGS. 8-9, the tip extension and the expanded medial extension are substantially toroidal; in other embodiments, they can be substantially spherical, substantially ovoid, substantially ellipsoidal, substantially the frustum of a cone (preferably with a rounded distal edge), substantially conic (preferably with a rounded distal edge) and any combination thereof.

The nozzle tip and the tip extension (1110) have a number of holes (1112, 1113) which fluidly connect the bore of the nozzle (1100) to the exterior of the device, allowing material to exit from the interior of the device. In the exemplary embodiments shown, there is a hole (1113) (FIGS. 8A and C; not shown in FIG. 9) in the distal end of the nozzle and four holes (1112) in the tip extension (1100). Both the extension and the distal end of the nozzle can have more or fewer holes and, in some embodiments, one or the other can have no holes. The holes (1112) can be regularly spaced around the periphery of the extension, the holes (1112) can be irregularly spaced around the periphery, the holes (1112) can be concentrated in a predetermined part of the periphery, and any combination thereof. Similarly, the holes in the distal end of the tip can be regularly or irregularly spaced in the tip.

In some embodiments, the extension (1110) can be padded, can comprise soft material, can comprise flexible material and any combination thereof.

Extensions, both tip extensions and medial extensions, can have a number of functions. A non-limiting list of such functions is (1) ensuring proper positioning of the nozzle (1100) in the nasal passages, where the proper position can be the nozzle (1100) centralized in the nasal passages, the nozzle (1100) touching a predetermined portion of the nasal passages, or the nozzle (1100) closer to a predetermined portion of the nasal passages, (2) sealing the nasal passages so that material can not escape therefrom, (3) sealing the nasal passage so that substance does not contact undesired portions thereof, (4) sealing the nasal passage so that substance remains in a predetermined region of the nasal passage, (5) reducing the discomfort of contact between the nozzle and the nasal passages, especially in embodiments where the extension is intended to seal against the walls of the nasal passages, by providing a soft and/or flexible contact region and any combination thereof. Proper positioning can be for the purpose of improving delivery of a substance to a predetermined area, preventing clogging of the holes by nasal secretions, preventing clogging of the holes by contact with the nasal passages, mucosa and any combination thereof.

Nozzle extensions, both those that are expanded during the activation procedure and those that have a predetermined shape and do not expand, can either (1) be attached to the nozzle in a way that they are removed from the nasal cavity with the nozzle tip itself, or (2) have the option of being releasable from the nozzle tip so that they stay in the nasal cavity until they are pulled out by the user or by a caregiver, or any combination thereof. In embodiments where at least one nozzle extension remains in a nasal cavity, preferably, the nozzle extension or extensions are removed after a predetermined time, preferably a short time.

In some embodiments, the holes (1112) in the nozzle (1100) do not lie substantially in a plane perpendicular to the main longitudinal axis of the nozzle (1100). In such embodiments, the holes (1112) can lie along a line parallel to the main longitudinal axis of the nozzle (1100), along a line forming a spiral around the nozzle (1100), irregularly in the distal portion of the nozzle (1100), regularly spaced in the distal portion of the nozzle (1100), and any combination thereof.

Therefore, dispersion of the drug can be substantially from a ring perpendicular to the main longitudinal axis of the nozzle (1100) (holes (1112) around the edge of the extension (1110), from a circle perpendicular to the main longitudinal axis of the nozzle (1100) (holes (1113) in the distal tip of the nozzle (1100), from a line (holes (1112) parallel to the main longitudinal axis of the nozzle (1100) or in a spiral around the main longitudinal axis of the nozzle (1100), or from at least part of the surface of a volume extending along the side of the nozzle (1100).

In some embodiments, the size of the tip extension (1110) is selected so that the extension (1110) is in contact with the nasal passages substantially along its entire circumference. In such embodiments, material exiting holes (1113) in the distal tip of the nozzle (1100) or holes (1112) on the distal face of the extension (1110) can not reach regions proximal to the extension (1110) and will reach only regions deeper in the nasal passages than the extension (1110). In such embodiments, the substance will reach the upper parts of the nasal passages.

Material exiting from holes (1112) in locations where the extension (1110) is in contact with the nasal passages will deposit directly on the walls of the nasal passages. In such embodiments, deposition is in a very narrow band; the location of the band can be tailored for the material of interest.

Material exiting holes (1112) proximal to the region of the extension (1110) in contact with the walls of the nasal passages will be unable to reach locations distal to the region of the extension (1110) in contact with the walls of the nasal passages and will therefore deposit in the lower parts of the nasal passages.

Returning to FIG. 9, in this embodiment, the expandable portion (1120) surrounds the nozzle (1100). In other embodiments, the expandable portion (1120) can partially surround the nozzle (1100). A single expandable portion (1120) or a plurality of expandable portions (1120) can be used. An expandable portion can be on the surface of the nozzle or it can be stored within the nozzle, popping out when it expands. An expandable portion can have a predetermined shape when expanded. The shape of the outward-facing part of an expandable portion can be part of the surface of a spheroid, can be part of a cylinder, a part of a cone, or can conform to the shape of a predetermined portion of a nasal passage. Such shaping can help ensure that, on inflation, the expandable portion or portions gently guide the nozzle so that it rests in the position with respect to the nasal passages or in the correct portion of the nasal passages. It can also reduce the user's discomfort when the device is in place or, if detachable from the device, it can seal the nasal passage for a time, before being removed by the user or a caretaker.

The expandable portion (1120) is preferably inflated after insertion of the device into the nasal passage. Inflation can be before or at the time of activation of the device.

It should be noted that the embodiments of the device are not limited to the exemplary embodiments shown in FIGS. 4-9.

In embodiments where delivery is to a nostril, delivery of the substance can be improved by inducing sniffing in the user.

Sniffing (short, sharp breaths through the nose, for example, when smelling something) is highly correlated with soft palate (Velum) position. Sniffs are rapidly modulated in an odorant-dependent fashion by a dedicated olfactomotor system, and affect the position of the soft palate at the posterior end of the nasal cavity. When sniffing through the nose, the palate is in its upper position to cause separation between the nasal cavity and the oral cavity.

In addition to conscious control, sniffing may be reflexively elicited by chemicals, functioning as either irritants or odors in the nose. Overall sniff duration and pattern can be modulated in real time to optimize olfactory perception.

When the olfactory system encounters a concentrated odorant, sniff vigor is reduced and sniff time is reduced; when it encounters a diluted odorant, sniff vigor is increased and duration lengthened. Odorant pleasantness also affects sniffing; sniff vigor and duration increase when smelling a pleasant odor and decrease when smelling an unpleasant odor.

In preferred embodiments, the device disclosed herein can release odorant into the nasal cavity of the user in order to reflexively elicit sniffing. The odorant can be a single odorant or a mixture of odorants and can comprise compounds from different chemical families, for non-limiting example:

Esters: Geranyl Acetate, Ethyl Acetate, Benzyl Acetate, Octyl Acetate.
Linear Terpens: Geraniol, Citral, Citronella, Nerolidol.
Cyclic Terpens: Terpineol, Thujone.
Aromatic: Eugenol, Vanillin, Anisole, Thymol.
Amines: Indole.
Also aromatic compounds of alcohols, aldehydes, esters, ketones, lactones, and thiols.

In preferred embodiments, the substance is contained within a capsule. The capsule can have a single compartment or it can be multi-compartment. The capsule can contain a broad range of drugs and materials. The aromatic compound can be stored in the nozzle, or the nozzle or a portion thereof can be impregnated with aromatic compound, so as to trigger the closing of the velum when the nozzle tip is being placed in the nasal cavity. The delivery can be for local effect, to the systemic circulation, to the central nerve system (CNS), to the brain, preferably via the olfactory epithelium, to the spinal cord and associated nerves, and any combination thereof.

As described hereinabove, the drugs and materials to be delivered can be, but are not limited to, pharmaceuticals, natural compounds, biologics, hormones, peptides, proteins, viruses, cells, stem cells and any combination thereof.

The stored substance or substances can be stored as a liquid, an aerosol, a powder, a slurry, a suspension, or a gel, if thin enough. The substance or substances can be stored either with or without a carrier; the carrier can be a liquid, a gas or a powder.

The substance as delivered can comprise a powder, a mixture of liquid and powder, a mixture of gas and powder, a mixture of powders, a liquid, a mixture of liquid and gas, a mixture of liquids, a gas, or a mixture of gases.

The stored substance or substances can be packaged to minimize degradation, for example, by packaging it in vacuum or under an inert atmosphere. Preferably, capsules are single-use so that a single, controllable dose can be delivered with each use of the device. Capsules can be placed in the container of the device, or the container can comprise the capsule.

Use of an inert gas for the carrier for delivery of the medication obviates the possibility of interactions between the user and the delivery carrier; allergies to carriers, especially in medications used for chronic illnesses, are a growing problem. Furthermore, the delivery carrier is in contact with the medicament for no more than a few seconds and more commonly for no more than a few milliseconds, thereby minimizing degradation of the medicament due to interactions with the delivery carrier.

Examples of drugs and materials deliverable using the device are given hereinbelow. All examples listed below are exemplary and are not limiting.

Deliverable drugs and materials include: treatments for allergic rhinitis; treatments for osteoporosis; vaccinations and immunizations; sexual dysfunction drugs; treatments for B12 deficiency; smoking cessation; treatment of gynecological problems; treatment of other women's health issues; general anesthetics; local anesthetics; opioid analgesics; agonist-antagonists and antagonists; antitussives; drugs used in the treatment of motor disorders; antiepileptics; drugs used in affective disorders; antipsychotics (neuroleptics); sedative-hypnotics, anxiolytics, and centrally acting muscle relaxants; treatments for anxiety disorders; skeletal muscle relaxants; treatments for Parkinson's disease; treatments for Alzheimer's disease; treatment for pain and anti migraine treatment.

Medicaments for treatment of allergic rhinitis include: steroids, including corticosteroids, Flonase, Patanase, Beconase, Anihistamine, Astelin, Otrivin™, Livostin, Theramax, Avamys, Lufeel, Sinofresh, Nasonex, Nasocort and Veramyst.

Medicaments for treatment of osteoporosis include: Miacalcin, Fortical and Stadol.

Medicaments for vaccinations and immunizations include: LAVIN, and influenza vaccines including FluMist.

Medicaments for smoking cessation include: NasalFent.

Other medicaments which can be delivered include: calcitonin and parathyroid hormone.

Neurotransmitters and neuromodulators that can be delivered include: acetylcholine (ACH), Anticholinergic drugs, adenosine triphosphate (ATP), aspartate (Asp), beta-amyloid, beta-endorphin, bradykinin, dopamine (DA), L-DOPA, Carbio-Dopa, epinephrine, dynorphins, endomorphins, enkephalins, 5-hydroxytryptamine (5-HT), Sumatriptan, Imitrex, Migranal, Zolmitriptan, Zomig, Gamma-aminobutyric acid (GABA), glutamate (glu), glycine, histamine, leptin, nerve growth factor and other growth factors), norepinephrine, nitric oxide, and Substance P.

General anesthetics which can be delivered include: alfentanil, desflurane, enflurane, etomidate, fentanyl, halothane, isoflurane, ketamine, methohexital, methoxyflurane, midazolam, lorazepam, diazepam morphine, nitrous oxide ($N_2O$), propofol, sevoflurane, Sufentanil, Sublimase, and thiopental.

Local anesthetics which can be delivered include: benzocaine, bupivacaine, cocaine, lidocaine, prilocaine, procaine, ropivacaine, and tetracaine.

Opioid analgesics, agonist-antagonists, and antitussives which can be delivered include: agonists, codeine, diphenoxylate, fentanyl, heroin and other opiods, hydrocodone, 1-alpha-acetyl-methadol, levomethadyl acetate, loperamide, meperidine, methadone, morphine, oxycodone, d-propoxyphene, combinations of opioids plus acetaminophen and asa, and tramadol.

Agonist/antagonists and antagonists which can be delivered include: buprenorphine, butorphanol, nalbuphine, nalorphine, naloxone, naltrexone, nalmefene, pentazocine, codeine, dextromethorphan, and hydrocodone.

Drugs used in the treatment of Parkinson's disease and motor disorders which can be delivered include: amantadine, apomorphin, baclofen, benzodiazepines, benztropine, bromocriptine, carbidopa, cyclobenzaprine, dantrolene, dopamine, entacapone, haloperidol, L-DOPA, pergolide, pramiprexole, ropinerole, selegiline (deprenyl), trihexyphenidyl, rasagiline, azilect, selegiline, ladostigil, rotigotine, neupro, mono amine oxidase inhibitor, and COMT inhibitor.

Antiepileptics which can be delivered include: acetazolamide, carbamazepine, clonazepam, diazepam, ethosuximide, felbamate, gabapentin, Lamotrigine, lorazepam, phenobarbital, phenytoin, primidone, tiagabine, topiramate, valproic acid, Vigabatrin and Midazolam.

Drugs used in affective disorders which can be delivered include: antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate and valproic acid.

Antipsychotics (neuroleptics) which can be delivered include: chlorpromazine (CPZ), clozapine, fluphenazine, haloperidol, olanzapine, quetiapine, risperidone, sertindole, thioridazine, thiothixene and ziprasidone.

Sedative-hypnotics, anxiolytics, and centrally acting muscle relaxants which can be delivered include: alprazolam, chloral hydrate, diphenhydramine, flumazenil, flurazepam, hydroxyzine, lorazepam, oxazepam, phenobarbital, temazepam, triazolam, zaleplon and zolpidem.

Anxiety disorders and skeletal muscle relaxants which can be delivered include: alprazolam, chlorazepate, chlordiazepoxide, diazepam, flumazenil (antagonist), lorazepam, and oxazepam.

Treatments for Alzheimer's disease which can be delivered include: donepezil, galantamine, rivastigmine, Tacrine, Detemir, Novolin, Humulin, Insulin, insulin like hormone, an insulin analog such as NPH Insulin, Lispro, Aspart, Detemir Insulin, Glulisin, Glargin Insulin, Insulin degludec, BDNF, GDNF, MIBG, anti cancer agents, anti cancer drugs, dopamine agonist and dopamine antagonist.

Other drugs which can be delivered include: amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, Pentobarbital, neuroprotective compounds, neuroprotective peptides, neuroprotective factors, davunetide, anti schizophrenic drugs, anti depression drugs, comtan, Entacopone, anti ADHD agents, anti ADHD drugs such as Methylphenidate (ritalin), and anti-autism and anti-autism symptoms drugs.

Other materials that can be delivered include: both purified natural and synthetic biologics, peptides, proteins, antibodies, cells including stem-cells, parts of cells, nanoparticles and microparticles. The nanoparticles and microparticles can comprise drugs; they can be carriers for drugs, cells or parts of cells; and any combination thereof.

In preferred embodiments, the substance comprises permeation enhancers to improve penetration of the active components of the substance through the mucosal membranes.

In some formulations, the formulation can comprise polymeric microparticles comprising at least one active agent and a permeation enhancer, where the active agent is selected from a group consisting of a peptide, a protein, an antibody, nucleic acid, small molecules, cells and any combination thereof.

A great number of penetration enhancers are known in the literature.

One such penetration enhancer is Hyaluronic acid (also referred to as HA or hyaluronan), which is a polysaccharide that occurs naturally in the body. Due to its exceptional water-binding, visco-elastic and biological properties, HA can improve the attributes, such as, but not limited to, the absorption characteristics, of existing formulations and can also add new attributes to existing formulations. Inclusion of HA can be advantageous when developing new formulations.

When used for drug delivery and targeting, HA can provide clear advantages over traditional polymeric substances such as synthetic polymers such as, but not limited to, poly(ethylene glycol), poly(lactic acid), poly(glycolic acid), poly Acrylic Acid and Poly-(N-isopropylacrylamide), or other biopolymers such as chitosan and alginate.

HA's benefits in the drug delivery area include, but are not limited to:

Flexibility when designing controlled drug release profiles;

More stable drug formulations;

Effective drug targeting via accumulation at the targeted site and receptor-mediated uptake;

Enhancement of bioavailability and biocompatibility of drugs; and

Reduction of drug cytotoxicity in healthy tissues polymeric microspheres polymeric controlled release preparation a mucoadhesive agent.

Other penetration enhancers include, but are not limited to the following:

A group containing: a fatty acid, a medium chain glyceride, surfactant, steroidal detergent, an acyl carnitine, Lauroyl-DL-carnitine, an alkanoyl choline, an N-acetylated amino acid, esters, salts, bile salts, sodium salts, nitrogen-containing rings, and derivatives. The enhancer can be an anionic, cationic, zwitterionic, nonionic or combination of both. Anionic can be but not limit to: sodium lauryl sulfate, sodium decyl sulfate, sodium octyl sulfate, N-lauryl sarcosinate, sodium carparate. Cationic can be but not limit to: Cetyltrimethyl ammonium bromide, decyltrimethyl ammonium bromide, benzyldimethyl dodecyl ammonium chloride, myristyltimethyl ammonio chloride, deodecyl pridinium chloride. Zwitterionic can be but not limit to: decyldimethyl ammonio propane sulfonate, palmityldimethyl ammonio propane sulfonate. Fatty acid including but not limit to: butyric, caproic, caprylic, pelargonic, capric, lauric, myristic, palmitic, stearic, arachidic, oleic, linoleic, linolinic acid, their salts, derivatives and any combinations or glyceride, monoglyceride, a diglyceride, or triglyceride of those fatty acids. Bile acids or salts, including conjugated or un conjugated bile acids, such as but not limited to: cholate, deoxycholate, tauro-cholate, glycocholate, taurodexycholate, ursodeoxycholate, tauroursodeoxycholate, chenodeoxycholate and their derivatives and salts and combinations. Permeation enhancer as comprises a metal chelator, such as EDTA, EGTA, a surfactant, such as sodium dodecyl sulfate, polyethylene ethers or esters, polyethylene glycol-12 lauryl ether, salicylate polysorbate 80, nonylphenoxypolyoxyethylene, dioctyl sodium sulfosuccinate, saponin, palmitoyl carnitine, lauroyl-1-carnitine, dodecyl maltoside, acyl carnitines, alkanoyl cjolline and combinations. Other include but not limited, 3-nitrobenzoate, zoonula occulden toxin, fatty acid ester of lactic acid salts, glycyrrhizic acid salt, hydroxyl beta-cyclodextrin, N-acetylated amino acids such as sodium N-[8-(2-hydroxybenzoyl)amino]caprylate and chitosan, salts and derivatives and any combinations.

Other enhancers include: formulations of water in oil, formulations of oil in water; emulsions, double emulsions, micro-emulsions, nano-emulsions, water in oil emulsions, oil in water emulsions; steroidal detergent, and an acylse; to allow better absorption in the mucosal tissue, better permeation and absorption in the target cells, better stability of the encapsulated drug/active ingredient.

Some embodiments comprise, either alone or in combination with a penetration enhancer, a mucoadhesive agent such as, but not limited to, bioadhesive proteins, carbohydrates and mucoadhesive polymers In the capsule of the present invention, the device comprises at least one compartment, and preferably a plurality of compartments, each containing a flowable substance. The delivery device is designed to rupture the compartments such that the flowable substances are mixed with a carrier, preferably air, and delivered to a predetermined deposition site, typically, but not exclusively, in the nasal passages.

Medicaments may be supplied as liquids, as powders, or as aerosols. In the preferred embodiment, the medicament is supplied in a single-dose capsule. In other embodiments, the medicament is supplied in a multi-dose capsule means, the multi-dose capsule configured to provide a single dose per activation.

In preferred embodiments, the flowable-substance capsule has a plurality of compartments. A compartment can contain at least one medicament, at least one medicament precursor, carrier gas, compressed gas, and any combination thereof.

The different compartments can contain different medicaments, with the plurality of medicaments delivered to the nostril or other delivery site in a single dose. In this manner, a plurality of medicaments may be supplied to the nostril in a single injection, with interactions occurring between the medicaments at most during the short time between activation of the device and the delivery of the substances and their deposition at the target site.

In some embodiments, interactions between components are unwanted. In such embodiments, a sequential release will utilize the short time period between release of the components and their absorption in the body to prevent such unwanted interactions and/or reactions.

In other embodiments, mixing and/or reactions are desired. In such embodiments, the reactions can occur all at once, by rupturing all of the compartments at the same time and mixing/interacting the components, either in the aerosol or in at least one mixing chamber. In other embodiments, a component can be added by needle insertion at a desired time before use, either into an empty compartment or into an occupied compartment (so that a desired reaction can occur). In other embodiments, the compartment walls rupture in a predetermined order, so that mixing/interaction occurs in stages, in a predetermined order. Mixing/interaction can occur in a compartment or compartments, in a mixing chamber, in the air passages of the device, in the aerosol, in the nasal (or other) passages of the body, and any combination thereof.

As a non-limiting example, a medicament can comprise four components, stored in four compartments of a capsule. Prior to activation, a fifth component is injected into compartment 1. After a predetermined time, the device is activated and the walls between compartment 1 and compartment 2 are broken, allowing mixing of 5/1 and 2. This followed by rupture of the walls surrounding component 3, which then mixes with 5/1/2 and reacts with 2. The last walls to rupture are those surrounding compartment 4; material 4 remains in a separate part of the aerosol and deposits on the nasal passages after deposition of 5/1/2/3.

In another example, precursor A mixes with precursor B to form intermediate C, and, subsequently, intermediate C mixes with precursor D to form final product E.

Mixing or reactions or release of components from different compartments can occur simultaneously, in different linked compartments, or they can occur sequentially, as in the example above. Any combination of sequential and simultaneous reactions and/or mixing and/or release can be used. Components can arrive at the deposition site simultaneously, either mixed or unmixed, sequentially, and any combination thereof.

It should be noted that there can be a predetermined delay of some fractions of a second between rupturing of walls of different compartments, in order to, for non-limiting example, allow complete mixing of one set of components or allow a reaction between one set of components to go to completion before the next mixing/reaction starts or the delivery starts.

In some embodiments, the device or, preferably, the capsule, comprises a mixing mechanism or mixing chamber, so that, as described above, components of the composition can mix and/or react during the activation process, enabling components to be stored separately and/or to be stored as stable precursors, but to deliver a predetermined treatment comprising at least one medicament to a predetermined delivery site.

In preferred embodiments of the device, the mixture of aerosol and pre-aerosolized mist is formed within the nozzle, with the hole at the lateral end of the nozzle having little effect on either the shape of the dispersion plume or the velocity of the aerosol.

Figures 10, 11:
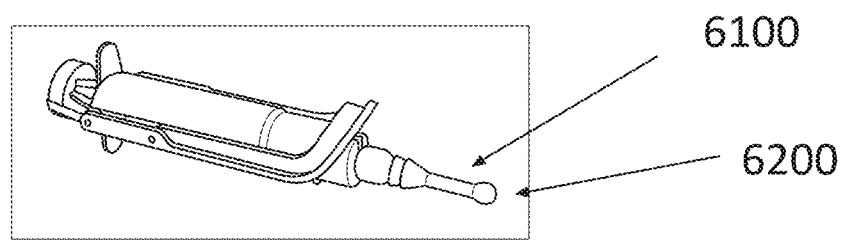

An experimental setup to demonstrate the location of formation of the mist is shown in FIG. 10, and the results of tests for three different operating conditions (1, 2 and 3) are shown in Table 1 and FIG. 11.

TABLE 1

Location of Aerosol Formation

| Test | Air Volume (ml) | Pressure (bar) | Orifice Diameter (mm) | Aerosol produced Before Exit from Device? |
|---|---|---|---|---|
| 1 | 19 | 6 | 0.8 | Yes |
| 2 | 8 | 4 | 0.8 | Yes |
| 3 | 8 | 6 | 0.8 | Yes |

FIG. 10 shows an embodiment of the device, with the nozzle (6100) and the nozzle tip (6200) on the right, with the mist-flowing region shown enlarged in FIG. 11.

Representation before activation is shown in the center of FIG. 11, and representation during activation is shown on the right. Before activation, the nozzle is clear; there is no aerosol therein. After activation, the nozzle appears opaque due to the aerosol and/or pre-aerosolized mist therein. If no aerosol or pre-aerosolized mist had been formed, the liquid would exit as a thin stream, which would appear in the image as a streak down the center of the nozzle.

EXAMPLE 1

An embodiment of a pressurized air carrier for providing controlled drug delivery to the nasal cavity.

Other embodiments can be used for delivery to the ear, mouth, throat and rectum.

In this embodiment of the device, the following parameters were variable, over the ranges given:

Pressure, between about 1 barg and about 20 barg
Air volume, between about 1 cc and about 50 cc
Time of activation, less than 0.5 sec Another important consideration, not investigated in this example, is the location of the nozzle in the body orifice, for non-limiting example, the depth of insertion of the nozzle in the nasal cavity.

In practice, at least one of: the pressure, air volume and time between charging and activation can be optimized based on the characteristics of the compound, drug or medicament such as, but not limited to, the volume, density, viscosity, state of matter, drug formulation, and any combination thereof. The compound can be a liquid, a powder or any combination thereof.

Pressure, air volume, time between charging and activation, and location of the orifice together with the characteristics of the delivered substance; all of the above contribute to the final distribution of aerosolized matter in the nasal cavity, or, in other words, the pattern of deposition of the aerosolized matter in the nasal cavity following discharge of the matter from a device with given predetermined parameters.

Other criteria which can be optimized include, but are not limited to, droplet size, droplet size distribution, droplet size as a function of time, and droplet size distribution as a function of time, plume geometry, pattern characteristics and particles' velocities.

The material as delivered is then a predetermined volume of the selected medicament in a predetermined form within a carrier comprising a predetermined volume of air/gas, with the volume of air/gas condensed at a predetermined pressure.

Tests showing the effect of changing pressure, air volume and time between charging and activation are given below. Deposition was measured in models that mimicked at least one aspect of the human nasal cavity (structure, friction, air flow, surface area or surface mucosa).

Model 1

A 36 cm long plastic tube with an inner diameter of 0.6 cm was used as a model for nasal friction and air resistance in the nasal cavity. The length of the aerosol distribution was measured, as well as the characteristics of the aerosol distribution.

2 mg/ml Methylene Blue in saline was used. The dye distribution pattern in the tube and the amount of dye that reached the end of the tube were observed.

Figure 12:
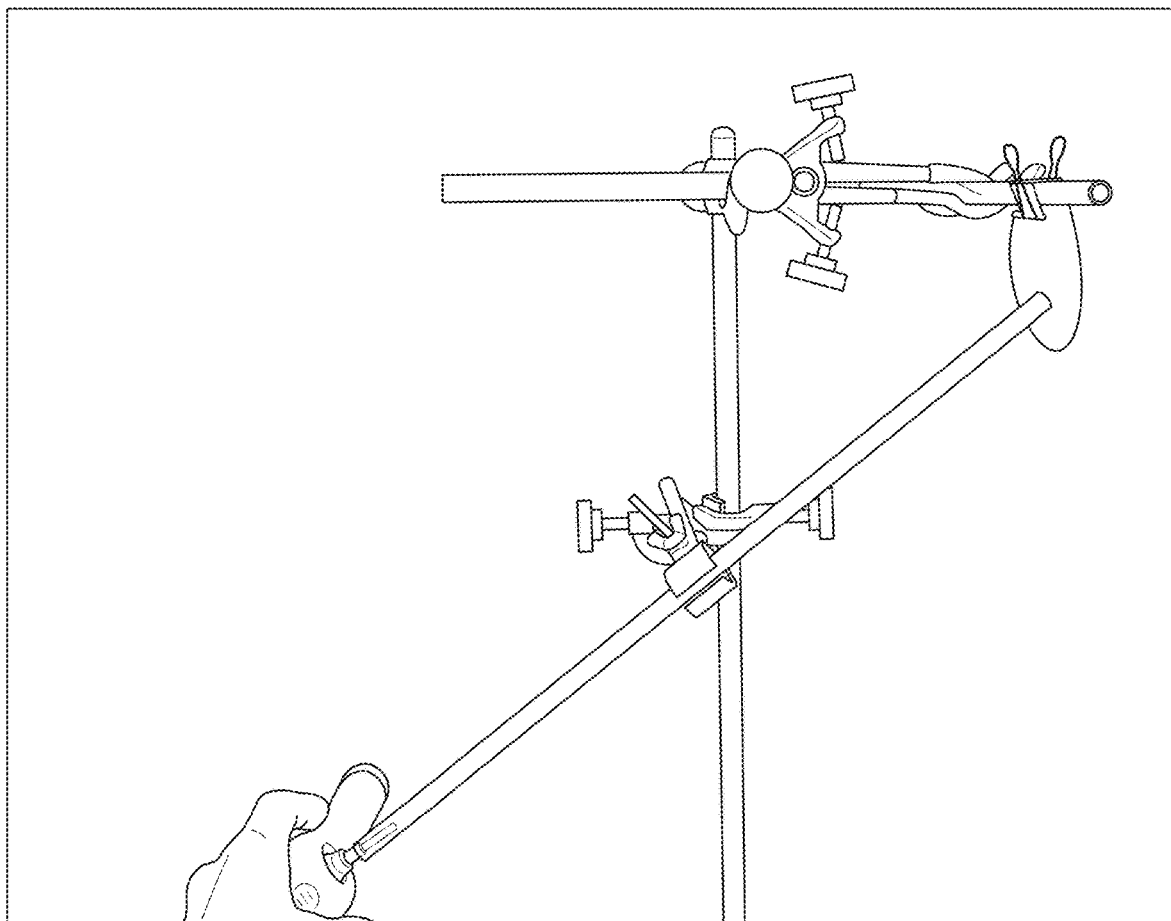

In reference to FIG. 12, a test setup is shown, showing a delivery device (2610), the plastic tube (2620), and an absorbent pad (2630) to capture material that has passed entirely through the tube.

In reference to FIG. 13A-B, a pressure of 4 barg and a liquid volume of 100 microliters were used for the tests. An air volume of 18 cc was used for the two results shown in FIG. 13A, while an air volume of 10 cc was used for the two results shown in FIG. 13B.

Delivery of the liquid dye through the end of the tube (2620), as determined by its deposition on the absorbent (2630), was more efficient for the air volume of 18 cc, as shown by the stronger color (showing more deposited material) and more-even distribution in FIG. 13A as compared to FIG. 13B.

In reference to FIG. 14A-B, the deposition characteristics on the inner tube surface were much better for the 18 cc air volume (FIG. 14A) than for the 10 cc volume (FIG. 14B), with deposition of aerosol on the inner tube surface being much more homogeneous, being delivered over a longer distance and having much smaller droplets with the 18 cc air volume (FIG. 14A) than with the 10 cc air volume (FIG. 14B).

In reference to FIG. 15A-B, a pressure of 2 barg and a liquid volume of 100 microliters were used for the tests. An air volume of 14 cc was used for the two results shown in FIG. 15A, while an air volume of 5 cc was used for the two results shown in FIG. 15B. Similarly to the results for FIG.

13, delivery of the liquid dye through the tube to the end of the tube (2620), as determined by its deposition on the absorbent (2630), was more efficient for the air volume of 14 cc, as shown by the stronger color (showing more deposited material) and more-even distribution in FIG. 15A as compared to FIG. 15B.

In reference to FIG. 16A-D, an air volume of 20 cc, a pressure of 7 barg and a liquid dye volume of 100 µl was used for the tests. In these tests, the device was charged; a time of 0.5 min (FIG. 16A), 5 min (FIG. 16B), 50 min (FIG. 16C), and 150 min (FIG. 16D) was allowed to elapse; and the device was activated. As can be seen from FIG. 16A-D, the elapsed time between charging the device and its activation has virtually no influence on the results, indicating that the device can remain in the charged state for a prolonged period prior to activation and drug release.

Model 2

A nasal cast model was used to provide a more realistic comparison to the average human nasal cavity. Material dispersion and penetration into the nasal cavity layers was found to be dependent on the pressure and air volume and the form and characteristics of the material deposited.

Figure 17:
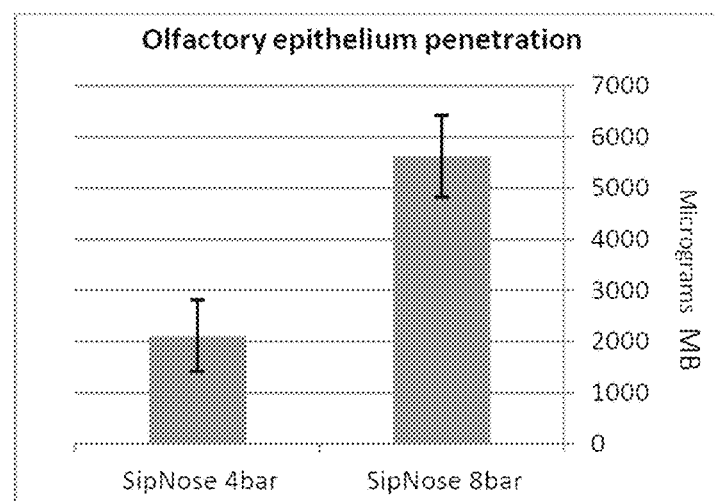

FIG. 17 shows the effect of pressure (with other parameters held constant) on deposition of a powder. More than 2½ times as much powder reached the olfactory epithelium with the 8 barg pressure, compared to the 4 barg pressure.

Model 3

The effects of air volume and air pressure on the distribution of 99mTC-DTPA aerosol in the nasal cavity and nasopharynx were examined using SPECT-CT for two human volunteers.

In both cases, the deposited material comprised 300 microliters of DTPA; 1.75 mc (milli Ciri) and the air volume was 20 ml. A pressure of 6 barg was used for the results shown in FIG. 18A, while a pressure of 4 barg was used for the results shown in FIG. 18B.

Figure 18A:
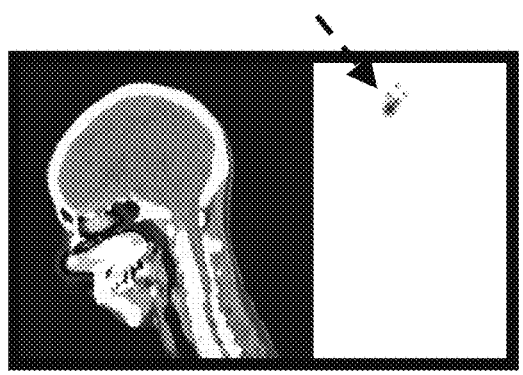
Figure 18B:
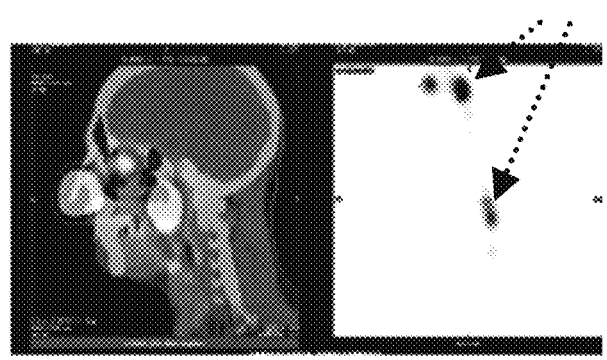

In FIG. 18A, the aerosol is localized in the nasal cavity at the respiratory and olfactory epitheliums (dashed arrow) and did not reach the Nasopharynx and did not enter the GI tract. In FIG. 18B, with a lower pressure, the aerosol is localized in the nasal cavity at the respiratory and olfactory epitheliums and also moved down into the Nasopharynx (upper dotted arrow) and into the GI tract (lower dotted arrow).

The pressure affected the distribution and thus the absorption of the aerosolized drug in the human body.

As shown hereinabove, the location and distribution of deposition of a desired substance and the characteristics of the substance on deposition are controllable by controlling parameters such as pressure, air volume, substance volume and nozzle shape.

EXAMPLE 2

In all known other mechanisms of creating aerosols, an orifice is placed at the end of a nozzle and the inner diameter of the device's nozzle and, especially, its orifice, is the main parameter that influences aerosol formation and the aerosol's characteristics. In contrast, in the present invention, no orifice is needed. More than that, putting a conventional orifice at the end of the nozzle will actually limit the forces reaching the liquid or powder being dispensed, and thus will reduce the ability to create the desired fine aerosol at the target site. Thus, the large diameter tubing that can be used in the present invention, about an order of magnitude larger than the diameter of commonly-used tubes and orifices, results in the desired fine aerosol, carried efficiently into the nasal cavity with droplet median diameters (DV50) on the order of 1-100 micrometer.

In the present invention, the aerosol is created as a result of the air volume-pressure parameters of the device and is influenced by the nasal cavity resistance rather than primarily by the orifice diameter.

In order to model nasal friction and air resistance and as a model for aerosol formation in the nasal cavity, a 36 cm long glass tube with an inner diameter of 2 cm, filled with oil up to 22 cm of its length, was used.

Theoretical analysis has indicated that 5 cm of tube is equivalent to about 0.1-0.5 cm of the nasal passages; therefore the 22 cm. tube would approximately simulate the full depth of a nasal passage.

The test material was 200 microliter of Methylene Blue liquid solution.

The liquid solution was discharged from a device into the base of the tube and pictures and videos were taken in order to be able to follow the process of aerosol formation. The length of the deposition region, the aerosol distribution and the diameter of the aerosol droplets were determined as a function of time.

FIGS. 19A-D show the effect of orifice size on droplet size (FIGS. 19B, D) and droplet distribution (FIGS. 19A, C) in a conventional device.

Figure 19A:
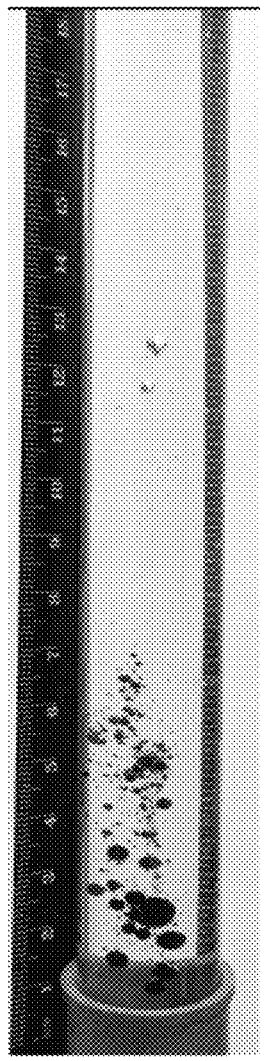
Figure 19B:
Figure 19C:
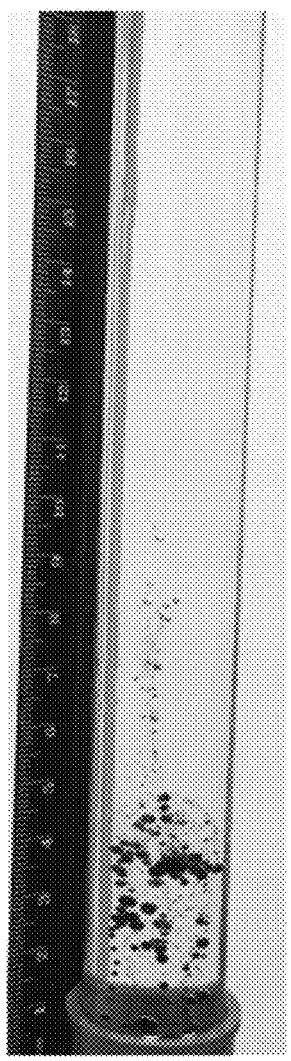
Figure 19D:

The Methylene blue solution was injected into the tube using a syringe. FIGS. 19A-B show droplet distribution and size for a larger needle (21G; approx. 0.5 mm) and FIGS. 19C-D show droplet distribution and size for a smaller needle (25G; approx. 0.2 mm). The larger diameter needle (FIGS. 19A-B) creates larger droplets than the smaller diameter needle (FIGS. 19C-D).

In contrast, FIGS. 20A-D and 21A-D show that the opposite is true if the technique of the present invention is used, where the aerosol is created by means of a pressurized gas.

In reference to FIG. 20, FIGS. 20A-D show the effect of orifice size on droplet size (FIGS. 20B, D) and droplet distribution (FIGS. 20A1, A2, C) in a device of the present invention. FIG. 20A1 shows the distribution in the lower part of the tube, while FIG. 20A2 shows the distribution in the upper part of the tube.

In FIGS. 20A-D, the device of the present invention is charged to 7 barg pressure and 20 ml of Methylene Blue solution is discharged through an orifice into the base of the tube. FIGS. 20A-B show droplet distribution and size for a larger needle (21G; approx. 0.5 mm) and FIGS. 20C-D show droplet distribution and size for a smaller needle (25G; approx. 0.2 mm). In this case, the larger nozzle (FIGS. 20A, B) has smaller diameter droplets, a more homogeneous aerosol and a distribution that extends much further up the tube than the smaller diameter nozzle (FIGS. 20C, D).

In reference to FIG. 21, FIGS. 21A-D show the effect of orifice size on droplet size (FIGS. 21B, D) and droplet distribution (FIGS. 21A, C) in a device of the present invention.

Figure 21A:
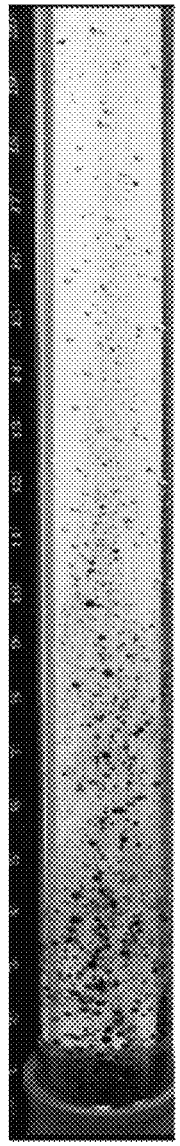
Figure 21B:
Figure 21C:
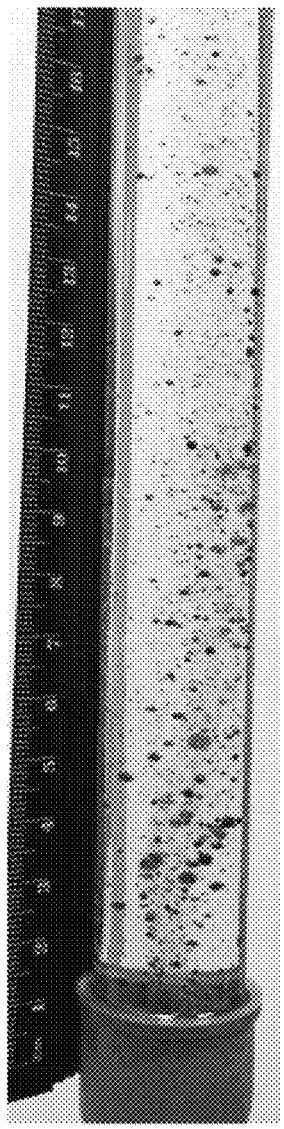
Figure 21D:
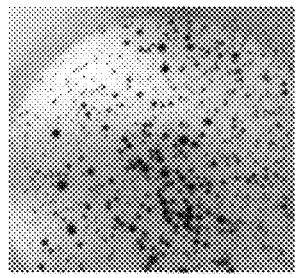

In FIGS. 21A-D, the device of the present invention is charged to 4 barg pressure and 18 ml of Methylene Blue solution is discharged through an orifice into the base of the tube. FIGS. 21A-B show droplet distribution and size for a larger needle (21G; approx. 0.5 mm) and FIGS. 21C-D show droplet distribution and size for a smaller needle (25G; approx. 0.2 mm). In this case, the larger nozzle (FIGS. 21A, B) has smaller diameter droplets and a more homogeneous aerosol than the smaller diameter nozzle (FIGS. 21C, D).

A comparison of FIGS. 20 and 21 shows that the higher volume-higher pressure combination (20 ml, 7 barg) has smaller diameter droplets with a greater homogeneity and a distribution that extends much further up the tube than the lower volume-lower pressure combination (18 cc, 4 barg).

Figure 22A:
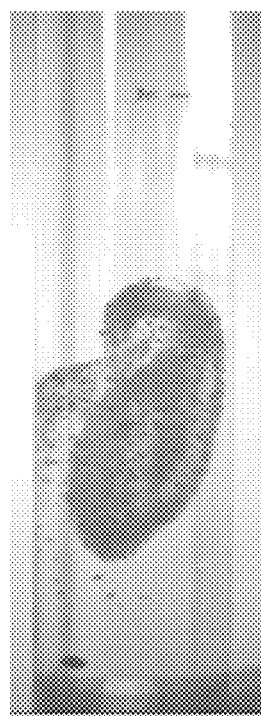
Figure 22B:
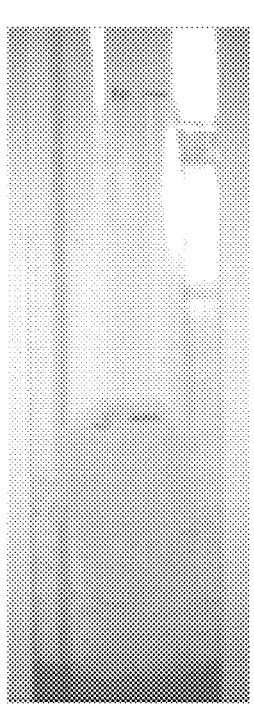
Figure 22C:
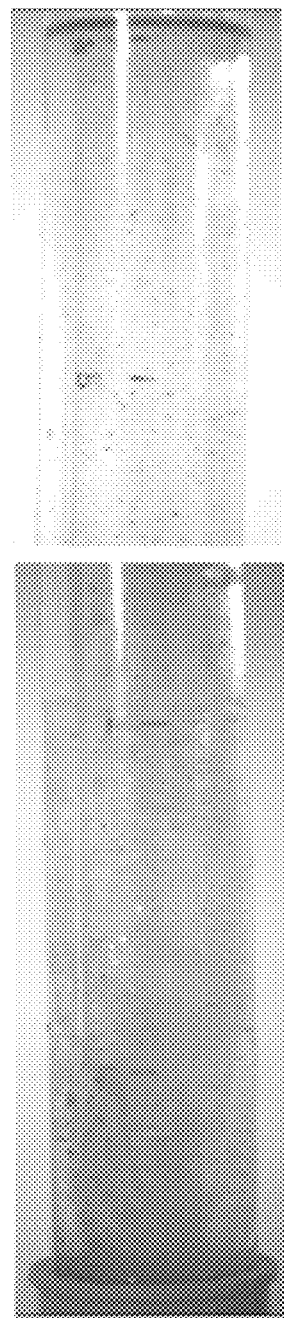
Figure 23A:
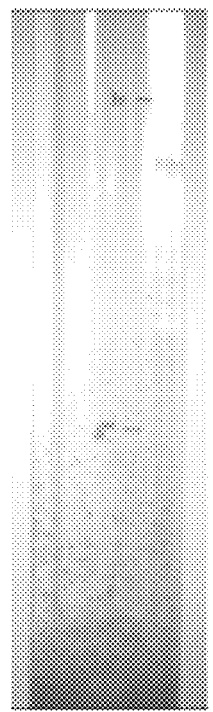
Figure 23B:
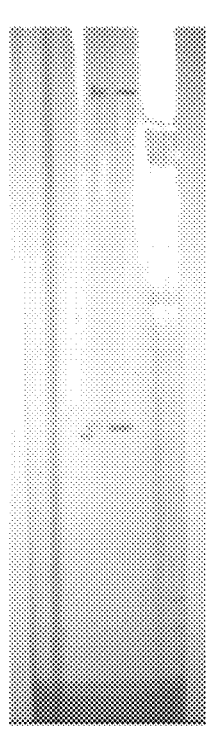
Figure 23C:
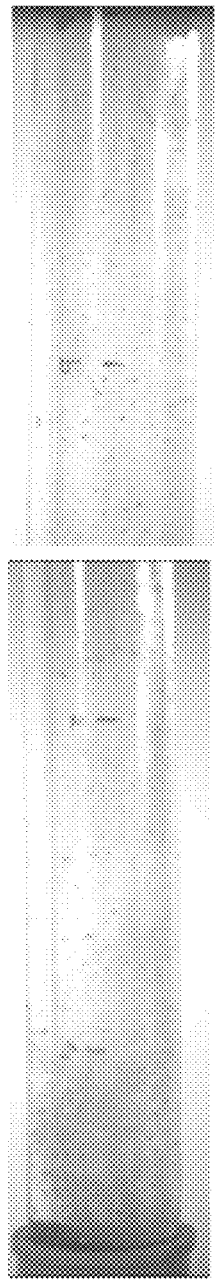
Figure 24:
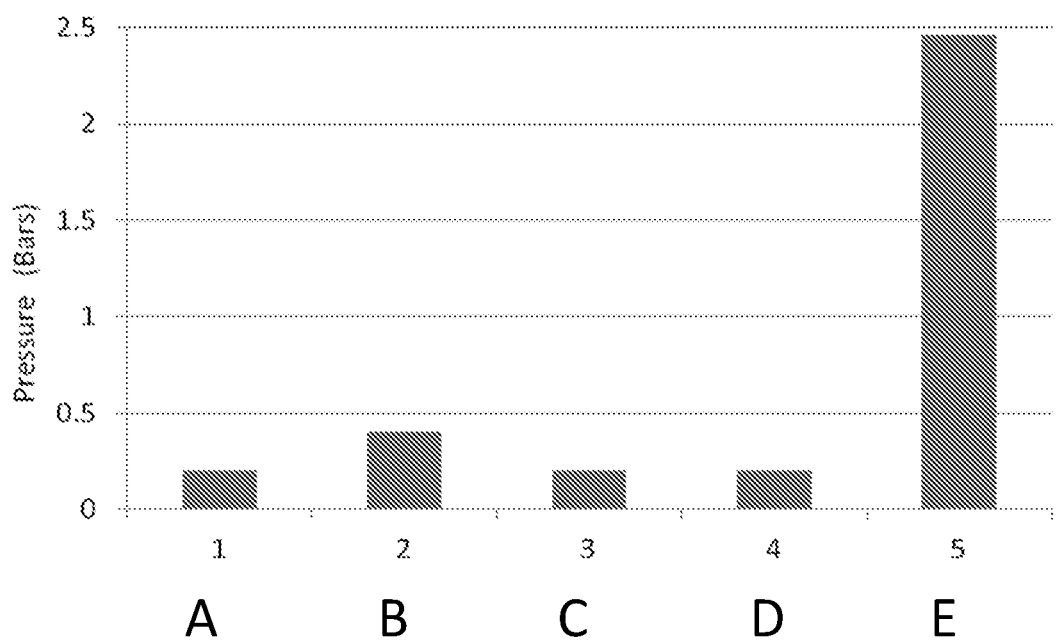
Figure 25A:
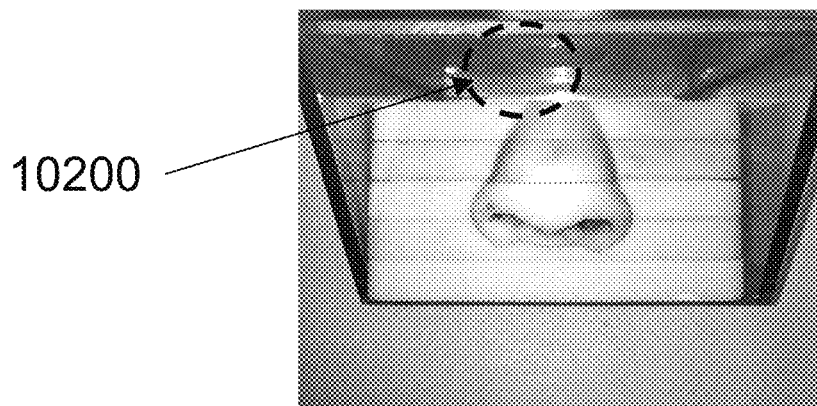
Figure 25B:
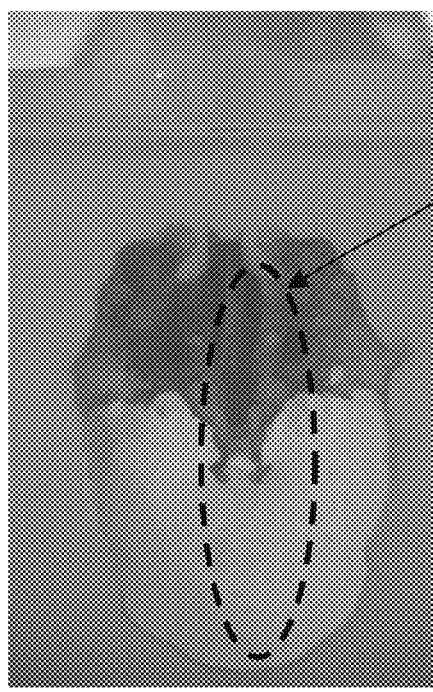
Figure 25C:
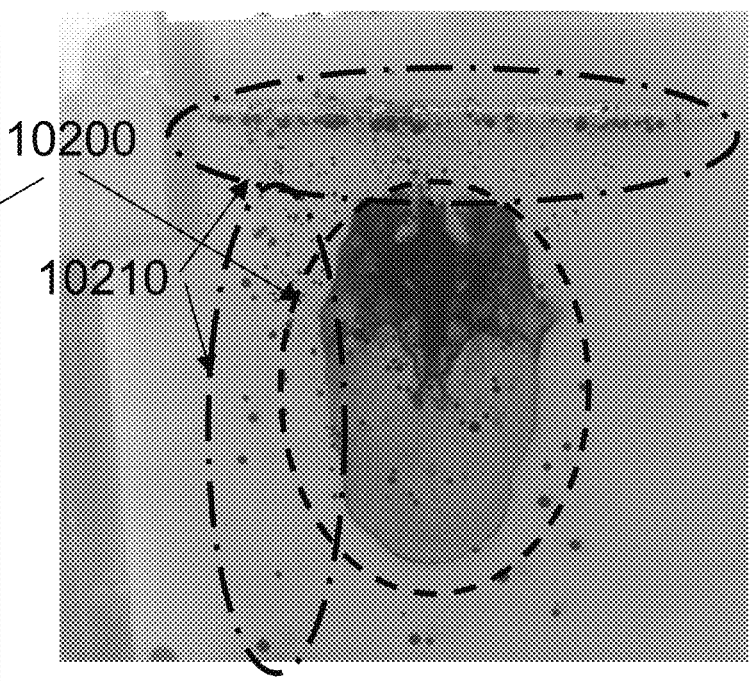

In FIGS. 22 and 23, a comparison is made between 2 commercial, prior art devices and the present invention device. In all cases, 0.1 ml of aqueous solution was tested. In FIGS. 22A and C and 23A and C, the liquid was Methylene Blue in aqueous solution; in FIGS. 22B and 23B, saline solution alone was used. The liquid was discharged from the device into the base of a tube filled with oil. In FIGS. 22A and 23A, the Otrivin™ device was use, in FIGS. 22B and 23B, the Otrimer™ device was used, and in FIGS. 22C and 23C, the present invention technology was used. For both the Otrivin™ (FIG. 22A) and the Otrimer™ (FIG. 22B) devices, the height reached by the solution at the time of application is less than 10 cm and the liquid forms a distinct bolus near the bottom of the tube. In contrast, with the device demonstrates the present invention (FIG. 22C), the liquid appears in the tube as small droplets, with some of the droplets reaching a height in the tube of 20 cm.

Two minutes later, (FIGS. 23A-C), the liquid from the Otrivin™ device has reached a height of about 5 cm (FIG. 23A), while the liquid in from the Otrimer™ device has fallen to the base of the tube; it is barely visible at the bottom of the tube in FIG. 23B. In contrast, the droplets are fairly stable in the tube in the present invention technique (FIG. 23C); there is a fairly even distribution of droplets until a height of about 12 cm is reached, and some of the droplets have reached a height of nearly 20 cm.

In reference to FIG. 24, nasal applicators were connected to a ~7 ml volume closed tubing, with a connection to a pressure sensor. The ~7 ml volume represents the approximate volume of the nasal cavity. The devices were discharged into the closed tubing and the maximum pressure developed in the tubing was measures. The pressure in the tubing for the four commercial devices, the Otrivin™ device (FIG. 24A), the Marimer device (FIG. 24B), the Rhinox device (FIG. 24C), and the Alrin™ device (FIG. 24D) were less than 1 barg. In contrast, the pressure in the tubing from the present investion technology (FIG. 24E), was almost 2.5 barg, more than 2½ times as much as the closest commercial device, the Marimer device (FIG. 24B).

In reference to FIG. 25, Methylene Blue in aqueous solution was delivered through a nostril of a human nasal cast model (FIG. 25A) filled with oil to mimic the nasal cavity's inner pressure and conditions. The dashed circles (10200) show the exit from the top of the nasal cast; material that reaches the exit would reach the olfactory epithelium in the nose. FIGS. 25B and C show nasal cast models after application of the Otrivin™ device (FIG. 25B) and the present invention technology based device (FIG. 25C) to a nostril of the nasal cast. As can be seen from FIG. 25B, no material would reach the olfactory epithelium with the Otrivin™ device—no material has reached the exit from the nasal cast. In contrast, droplets of material (dotted circle, 10210) have exited the nasal cast, showing that, unlike the commercial devices, the material discharged from the present invention technology based device is capable of reaching the olfactory epithelium.

In the following examples, results were obtained in a set of experiments made using the device, where, in each example, one parameter is changed and all others are fixed.

In Examples 4-11, the distance the aerosol migrated was measured in a plastic tube with an inner diameter of 0.5 cm and 345 cm long. Measurements were done at room temperature.

For Examples below, in Examples 4-9, the substance was a liquid and 100 microliters of saline were used for each activation of the device unless otherwise stated, and in Examples 10-11, the substance was a powder.

A. Liquid Aerosol Experiments

EXAMPLE 3

Effect of Pressure

For a SipNose device, for an orifice diameter of 0.8 mm and an air volume of 3 ml, the effect of pressure on the distance the aerosol migrates is shown in Table 2 and FIG. 26A-C.

TABLE 2

Effect of pressure on distance aerosol migrates

| Pressure (Barg) | Distance Aerosol Migrates (cm) |
|---|---|
| 1.2 | 120 |
| 4.0 | 165 |
| 6.0 | 230 |

The point at (0,0) (3330) was not a measured point, but could be included to improve the quality of the fits. The dotted line (3310) connects the data points, including the additional point at (0,0). The solid line (3320) shows fits to the data.

FIG. 26A shows a best-fit straight-line to the data, excluding the point at zero, where the distance L is $L=a_{1a}P+b_{1a}$ for distance L is in cm and pressure P is in barg. The parameter $a_{1a}$ is in a range of about 0 to about 70 and $b_{1a}$ is in a range of about 0 to about 130 for distance L is in cm and pressure P is in barg. The data fit well to the straight line, although the line does not pass near the point at (0,0).

FIG. 26B shows a best-fit cubic to the data, including the point at zero, where the distance L is $L=a_{1b}P^3-b_{1b}P^2+c_{1b}P$ for distance L is in cm and pressure P is in barg. The parameter $a_{1b}$ is in a range of about 2 to about 6, and $b_{1b}$ is in a range of about −20 to about −60 and $c_{1b}$ is in a range of about 70 to about 230 for distance L is in cm and pressure P is in barg. The data fit well to the cubic line.

FIG. 26C shows a best-fit power fit to the data including the point at zero, where the distance L is $L=a_{1c}P^{b1c}$. The parameter $a_{1c}$ is in a range of about 71 to about 120 and $b_{1c}$ is in a range of about 0.30 to 0.63 for distance L is in cm and pressure P is in barg. The data fit well to the power-law curve.

EXAMPLE 4

Effect of Orifice Diameter

For a SipNose device, the effect of orifice diameter on the distance the aerosol migrates is shown in Table 3 and FIG. 27A-B.

TABLE 3

Effect of orifice diameter on distance aerosol migrates

| Pressure (barg) | Air Volume (ml) | Orifice Diameter (mm) | Distance Aerosol Migrates (cm) |
|---|---|---|---|
| 6 | 19 | 0.26 | 20 |
| 6 | 19 | 0.49 | 280 |
| 6 | 19 | 0.8 | ≥345 |
| 6 | 19 | 1 | 340 |

For constant pressure and air volume, the larger the orifice diameter, up to about 0.8 mm, the further the aerosol migrates. Fits were made to these data.

The point at (0,0) (3330) was not a measured point, but could be included to improve the quality of the fits. The dotted line (3310) connects the data points, including the additional point at (0,0). The solid line (3320) shows fits to the data.

Figure 27A:
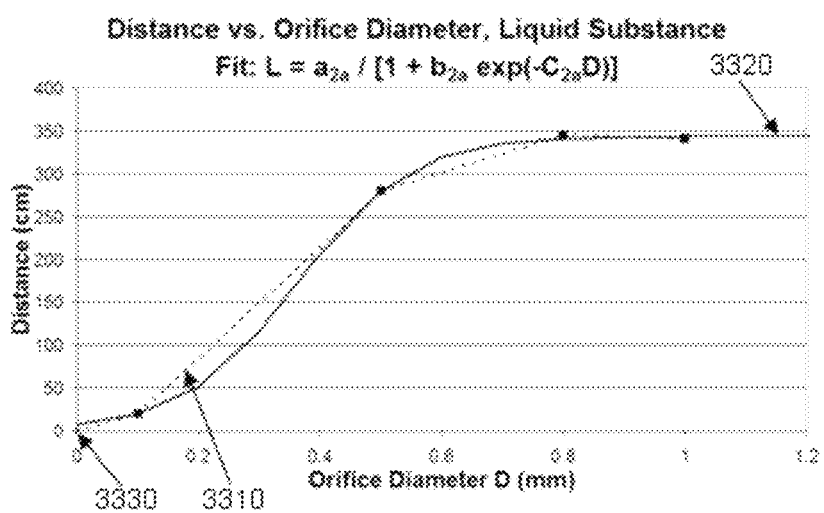

FIG. 27A shows a best-fit line, including the point at zero, to the equation $L=a_{2a}/(1+b_{2a}\exp(-c_{2a}D))$ where the distance L in cm and pressure P is in barg. The parameter $a_{2a}$ is in a range of about 325 to about 363, $b_{2a}$ is in a range of about −47 to about 163 and $c_{2a}$ is in a range of about 7 to about 15. The data fit well to the equation.

Figure 27B:
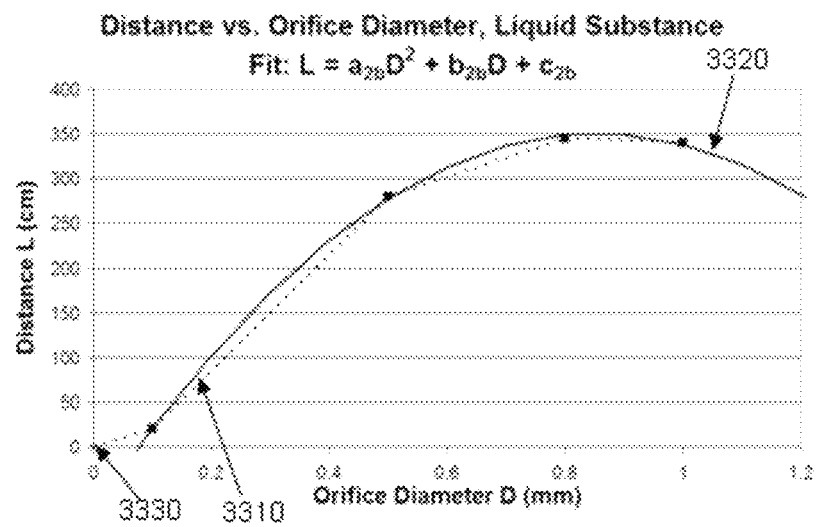

FIG. 27B shows a best-fit line, including the point at zero, to the equation $L=a_{2d}/(1+b_{2a}\exp(-c_{2a}D))$ where the distance L in cm and pressure P is in barg. The parameter $a_{2b}$ is in a range of about −928 to about −229, $b_{2b}$ is in a range of about 600 to about 1378 and $c_{2b}$ is in a range of about −160 to about 15. The data fit well to the equation.

EXAMPLE 5

Effect of Drug Volume

Figure 28A:
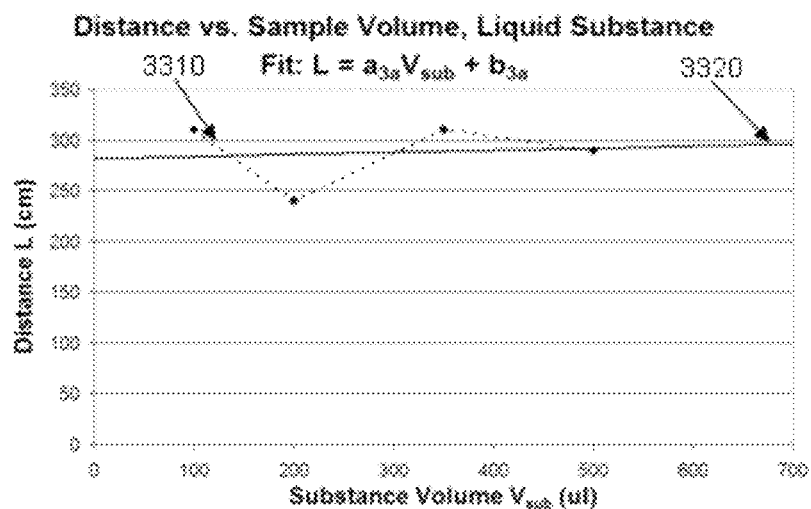
Figure 28B:
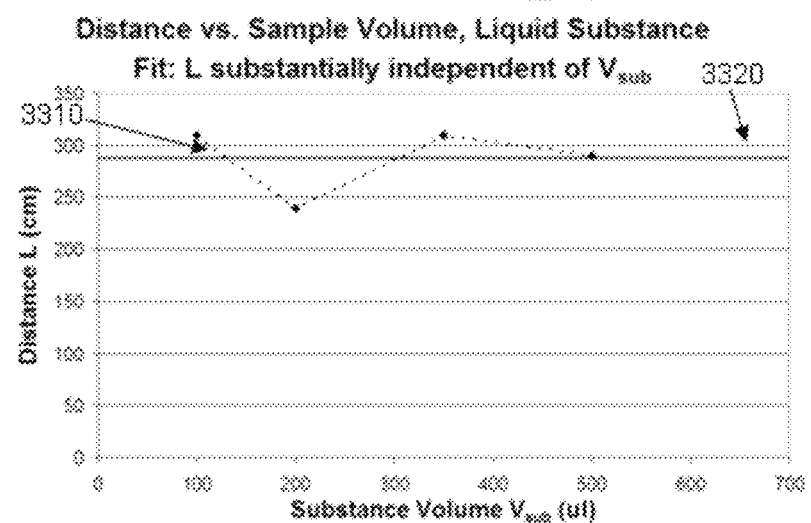

The effect of the amount of drug on the distance the aerosol migrates is shown in Table 4 and fits to the SipNose data are shown FIG. 28A-B.

TABLE 4

Effect of drug volume on distance aerosol migrates

| Device Type | Substance Type | Pressure (barg) | Air Volume (ml) | Orifice Diameter (mm) | Amount of Drug | Distance Aerosol Migrates (cm) |
|---|---|---|---|---|---|---|
| SipNose | Liquid | 6 | 19 | 1 | 100 μl | 310 |
| SipNose | Liquid | 6 | 19 | 1 | 200 μl | 240 |
| SipNose | Liquid | 6 | 19 | 1 | 350 μl | 310 |
| SipNose | Liquid | 6 | 19 | 1 | 500 μl | 290 |
| Nasal Pump from Alrin | Liquid | — | — | — | 100 μl | 45 |
| MAD, Wolfe Tory | Liquid | — | — | — | 100 μl | 30 |
| MAD, Wolfe Tory | Liquid | — | — | — | 200 μl | 40 |
| MAD, Wolfe Tory | Liquid | — | — | — | 600 μl | 45 |
| Simply Saline Nasal Mist | Liquid | — | — | — | ~200 μl | 40 |
| Optinose/Direct Haler technology, release time >1 sec) | Straw with dry powder | — | — | — | ~100 mg | 180 |

In all cases, the aerosol migrates significantly further down the tube for the SipNose device than for the commercial devices.

For the SipNose device, the point at (0,0) (3330) was not a measured point, but could be included to improve the quality of the fits. The dotted line (3310) connects the data points, including the additional point at (0,0). The solid line (3320) shows fits to the data.

FIG. 28A shows a best-fit line for the SipNose data, including the point at zero, to the equation $L=a_{3a}V_{sub}+b_{3a}$ where the distance L in cm and pressure P is in barg. The parameter $a_{3a}$ is in a range of about −0.55 to about 0.59 and $b_{3a}$ is in a range of about 96 to about 467. The data fit well to the equation although it is clear that the primary effect on the migration distance L is the carrier gas volume rather than the drug volume, since the line clearly does not pass through zero.

FIG. 28B shows that, for the SipNose data, for drug volumes in the range of interest, a good fit can be had by assuming that the drug volume has no effect on the migration distance.

EXAMPLE 6

Effect of Sample Viscosity

Figure 29:
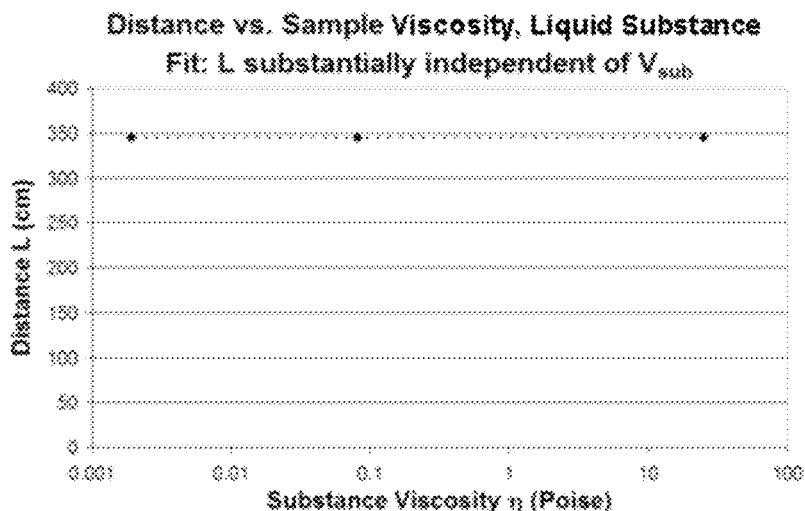

The effect of the viscosity of the sample on the distance the aerosol migrates is shown in Table 5 and FIG. 29.

It is clear that, over the range of viscosities investigated, the viscosity has no more than a negligible effect on the migration distance.

TABLE 5

Effect of sample viscosity on distance aerosol migrates

| Sample | Sample Viscosity (cP) | Orifice Diameter (mm) | Air Volume (ml) | Pressure (barg) | Distance Aerosol Migrates (cm) |
|---|---|---|---|---|---|
| Saline | 0.94 | 0.8 | 19 | 6 | ≥345 |
| Oil | 10 | 0.8 | 19 | 6 | ≥345 |
| Otrivin ™ | 23 | 0.8 | 19 | 6 | ≥345 |

For viscosity in the range tested, from about 0.9 to about 23 cP, viscosity had no effect on the distance the aerosol migrates.

EXAMPLE 7

Effect of Gas Volume

Figure 30A:
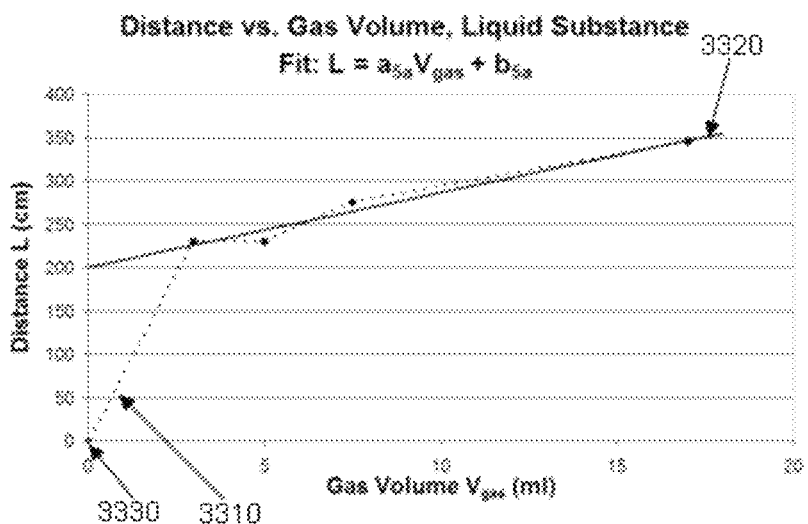
Figure 30B:
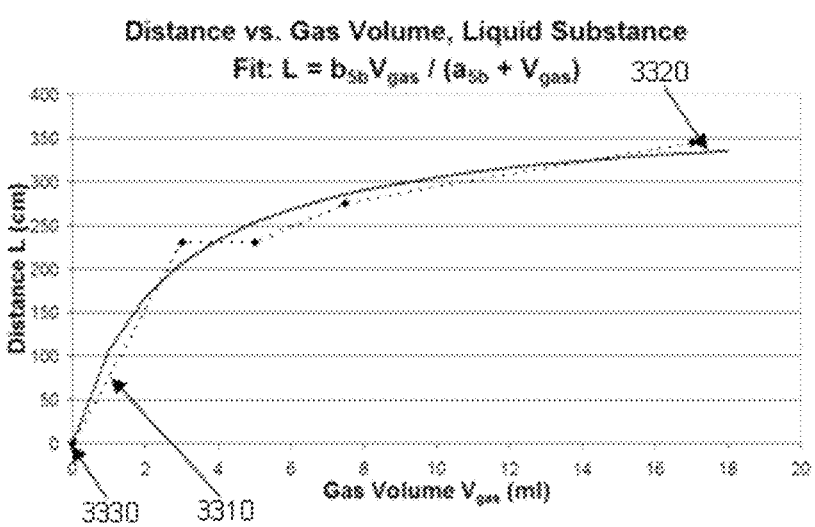
Figure 30C:
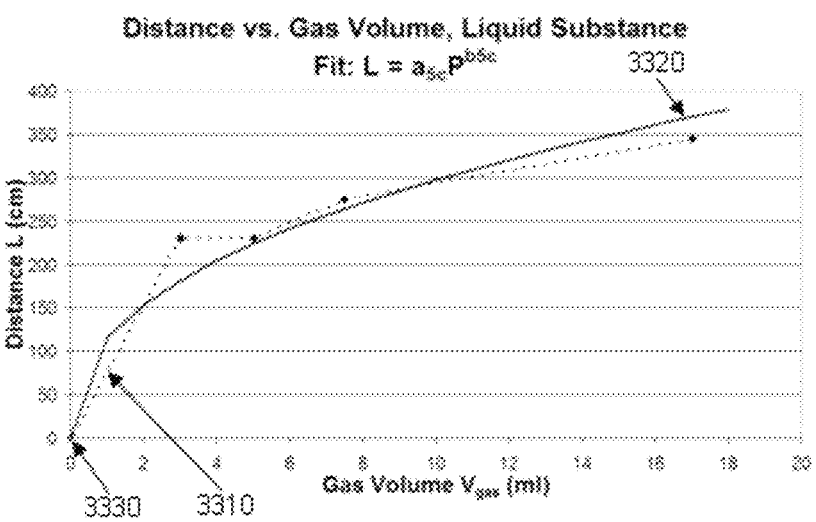

The effect of the volume of air in the sample on the distance the aerosol migrates is shown in Table 6 and FIG. 30A-C.

TABLE 6

Effect of gas volume on distance aerosol migrates

| Orifice Diameter (mm) | Gas Volume (ml) | Pressure (barg) | Distance Aerosol Migrates (cm) |
|---|---|---|---|
| 0.8 | 5 | 6 | 230 |
| 0.8 | 7.5 | 6 | 275 |
| 0.8 | 17 | 6 | ≥345 |

For constant orifice diameter and pressure, the larger the gas volume, the further the aerosol migrates. Fits were made to these data.

The point at (0,0) (3330) was not a measured point, but could be included to improve the quality of the fits. The dotted line (3310) connects the data points, including the additional point at (0,0). The solid line (3320) shows fits to the data.

FIG. 30A shows a best-fit line, excluding the point at zero, to the equation $L=a_{5a}V_{gas}+b_{5a}$ where the distance L in cm and pressure P is in barg. The parameter $a_{5a}$ is in a range of about 3.7 to about 13.5 and $b_{5a}$ is in a range of about 152 to about 248. The data fit well to the straight line, although the line does not pass near the point at (0,0).

FIG. 30B shows a best-fit line, including the point at zero, to the equation $L=b_{5b}V_{gas}/(a_{5b}+V_{gas})$ where the distance L is in cm and pressure P is in barg. The parameter $a_{5b}$ is in a range of about −0.18 to about 5.3 and $b_{5b}$ is in a range of about 268 to about 498. The data fit well to the cubic line.

FIG. 30C shows a best-fit power fit to the data including the point at zero, where the distance L is $L=a_{5c}V_{gas}^{b5c}$. The parameter $a_{5c}$ is in a range of about −19 to about 250 and $b_5$, is in a range of about −0.09 to about 0.9 for distance L is in cm and pressure P is in barg. The data fit well to the power-law curve.

EXAMPLE 8

Effect of Activation Duration

Figure 31:
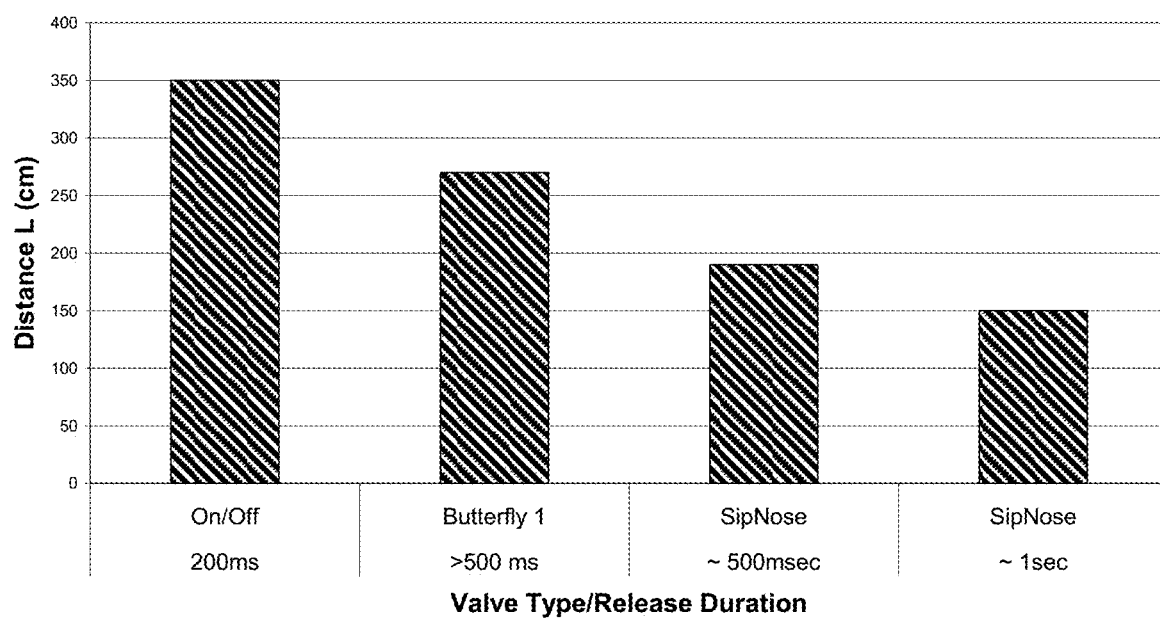

The effect of the duration of activation on the distance the aerosol migrates is shown in Table 7 and FIG. 31.

TABLE 7

Effect of release duration on distance aerosol migrates. Release duration reflects release time of the device

| Pressure (Barg) | Air Volume (ml) | Substance Volume (μl) | Tap Type | Release Duration (sec) | Orifice Diameter (mm) | Distance Aerosol Migrates (cm) |
|---|---|---|---|---|---|---|
| 6 | 19 | — | SipNose On/Off | 0.2 | 0.8 | 350 |
| 6 | 19 | — | SipNose Butterfly 1 | ~500 ms | 0.8 | 270 |
| 6 | 19 | 100 | SipNose | >500 msec | | 190 |
| 6 | 19 | 100 | SipNose | ~ 1 sec | | 150 |

Table 7 and FIG. 31 illustrates the effect of the valve type (used in the SipNose device) on the distance, Table 7 and FIG. 31 show that, typically, the shorter the time over which the gas is released, the further the aerosol migrates down the tube. Although not shown in Table 2, the on/off valve also had the largest diameter valve opening.

B. Powder Release Experiments

EXAMPLE 9

The Effect of Pressure

Figure 32:
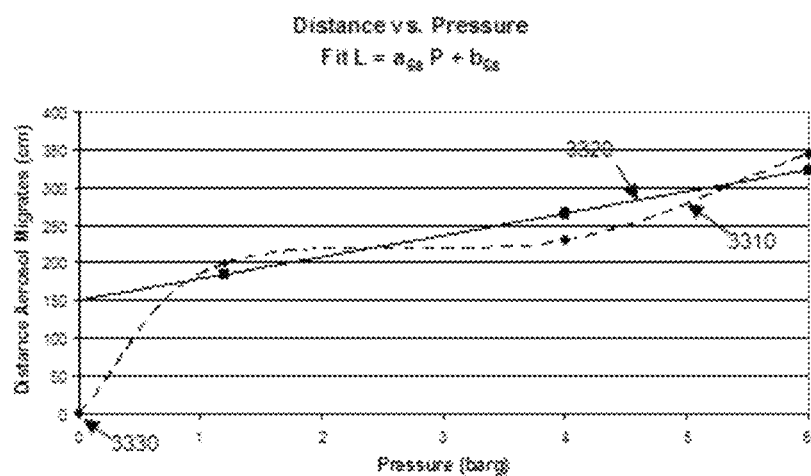

The effect of pressure on the distance the powder migrates is shown in Table 8 and FIG. 32.

TABLE 8

Effect of pressure on distance powder migrates

| Air Volume (ml) | Pressure (barg) | Orifice Diameter (mm) | Distance Aerosol Migrates (cm) |
|---|---|---|---|
| 5 | 1.2 | 2 | 200 |
| 5 | 4 | 2 | 230 |
| 5 | 6 | 2 | ≥345 |

The point at (0,0) (3330) was not a measured point, but could be included to improve the quality of the fits. The dotted line (3310) connects the data points, including the additional point at (0,0). The solid line (3320) shows fits to the data.

Figure 26A:
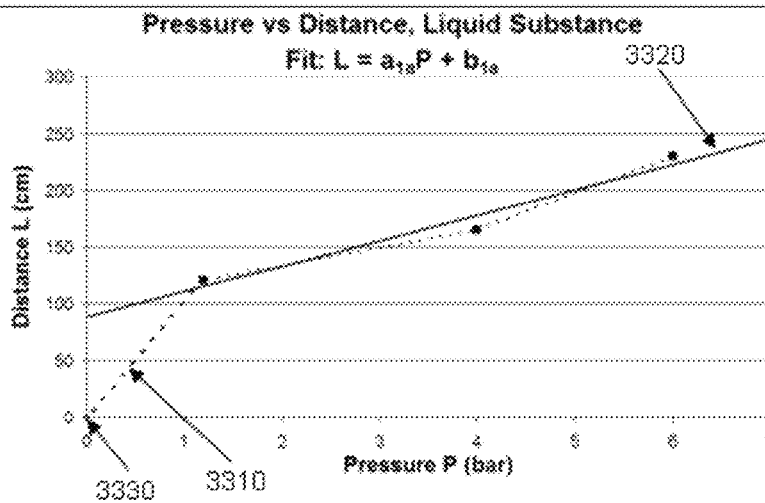

FIG. 26A shows a best-fit straight-line to the data, excluding the point at zero, where the distance L is $L=a_{6a}P+b_{6a}$, for distance L in cm and pressure P in barg. The parameter $a_{6a}$ is in a range of about 0 to about 116 and $b_{6a}$ is in a range of about 0 to about 306 for distance L is in cm and pressure P is in barg. The data fit well to the straight line, although the line does not pass near the point at (0,0).

Figure 26B:
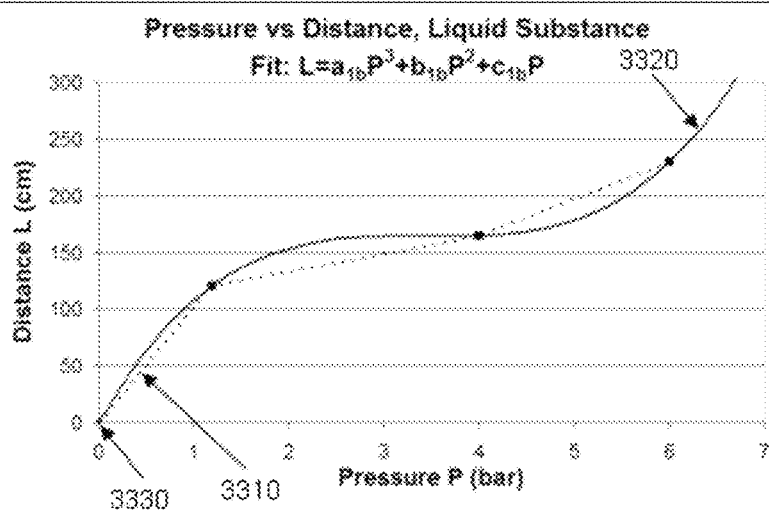
Figure 26C:
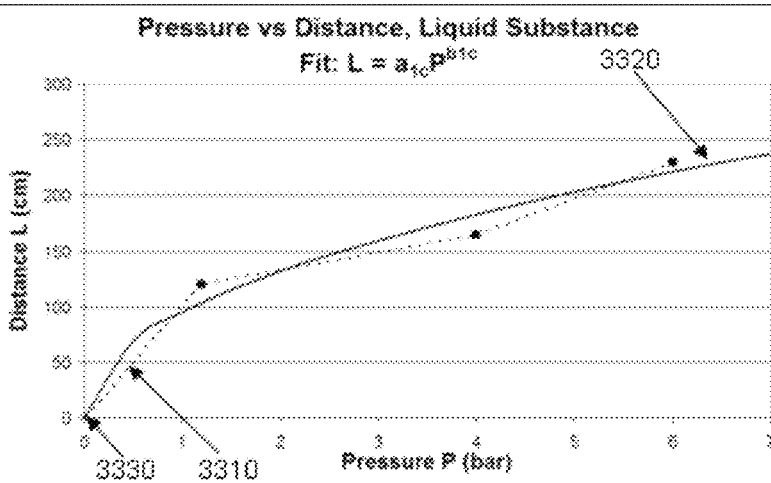

Similarly to the liquid substance example (Example 3, FIG. 26), a good fit is found (not shown) to the cubic $L=a_{6b}P^3-b_{6b}P^2+c_{6b}P$, for distance L in cm and pressure P in barg, where the parameters are: $a_{6b}$ is in a range of about 6.5 to about 9.75, $b_{6b}$ is in a range of about −65 to about −97.5 and $c_{6b}$ is in a range of about 202 to about 303.

Similarly to the liquid substance example (Example 3, FIG. 26), a good fit is found (not shown) to the power-law equation $L=a_{6c}P^{b6c}$, for distance L in cm and pressure P in barg, where the parameters are: $a_{6c}$ is in a range of about 0 to about 902 and $b_{6c}$ is in a range of about 0 to about 3.72.

EXAMPLE 10

Effect of Air Volume

Figure 33:
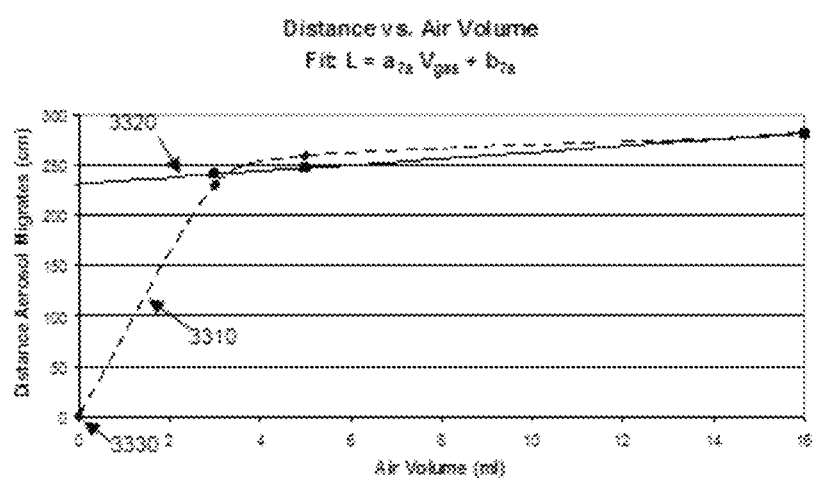

The effect of air volume on the distance the powder migrates is shown in Table 9 and FIG. 33.

TABLE 9

Effect of air volume on distance powder migrates

| Pressure (barg) | Air Volume (ml) | Orifice Diameter (mm) | Distance Aerosol Migrates (cm) |
|---|---|---|---|
| 4 | 3 | 2 | 230 |
| 4 | 5 | 2 | 260 |
| 4 | 16 | 2 | 280 |

For constant pressure and orifice diameter, the larger the air volume, the further the aerosol migrates. Fits were made to these data.

The point at (0,0) (3330) was not a measured point, but could be included to improve the quality of the fits. The dotted line (3310) connects the data points, including the additional point at (0,0). The solid line (3320) shows fits to the data.

FIG. 26A shows a best-fit straight-line to the data, excluding the point at zero, where the distance L is $L=a_{6a}P+b_{6a}$, for distance L in cm and pressure P in barg. The parameter $a_{6a}$ is in a range of about 0 to about 116 and $b_{6a}$ is in a range of about 0 to about 306 for distance L is in cm and pressure P is in barg. The data fit well to the straight line, although the line does not pass near the point at (0,0).

Similarly to the liquid substance example (Example 3, FIG. 26), a good fit is found (not shown) to the cubic $L=a_{6b}P^3-b_{6b}P^2+c_{6b}P$, for distance L in cm and pressure P in barg, where the parameters are: $a_{6b}$ is in a range of about 6.5 to about 9.75, $b_{6b}$ is in a range of about −65 to about −97.5 and $c_{6b}$ is in a range of about 202 to about 303.

Similarly to the liquid substance example (Example 3, FIG. 26), a good fit is found (not shown) to the power-law equation $L=a_{6c}P^{b6c}$, for distance L in cm and pressure P in barg, where the parameters are: $a_{6c}$ is in a range of about 0 to about 902 and $b_{6c}$ is in a range of about 0 to about 3.72.

EXAMPLE 11

Effect of Air Volume on Depth of Penetration into a Nasal Cast

In the nasal cast experiments, a model of the human nose was used, with slices of 1 cm each. In the following experiments, the distribution of the material (liquid aerosol or powder) was measured for a nasal cast model.

Figure 34:
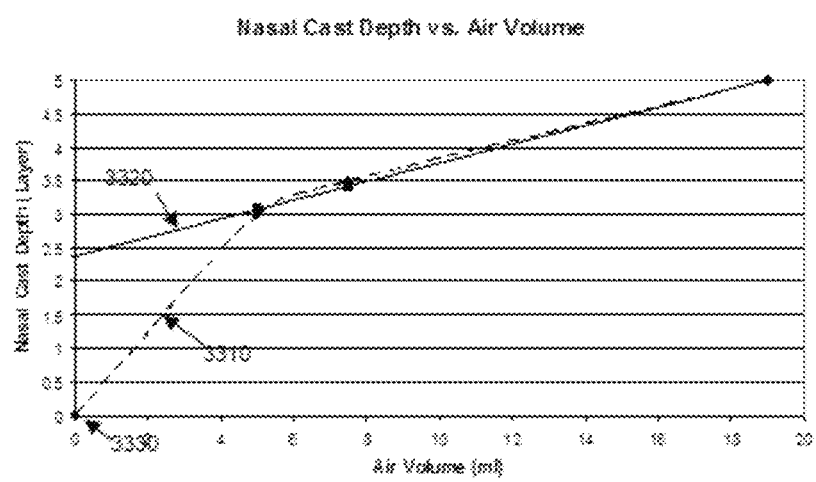

The effect of air volume on the depth the sample reaches in the nasal cast model is shown in Table 10 and FIG. 34.

TABLE 10

Effect of air volume on depth in nasal cast

| Pressure (barg) | Air Volume (ml) | Orifice Diameter (mm) | Deposition Layer (cm) |
|---|---|---|---|
| 6 | 5 | 2 | 3 |
| 6 | 7.5 | 2 | 3.5 |
| 6 | 19 | 2 | 5 |

The point at (0,0) (3330) was not a measured point, but is shown for reference, as a penetration of 0 layers would be expected for an air volume of zero (no delivery gas). The dotted line (3310) connects the data points, including the additional point at (0,0). The solid line (3320) shows a linear fit to the measured data. Over the range of air volumes of interest, between about 5 ml and about 19 ml, the depth of penetration into the nasal cast increases substantially linearly with air volume, although the irregularities of the nasal passages, as reflected in the nasal cast, might have suggested a sublinear relationship.

According to another embodiment, the fit can be selected from a group consisting of logarithmic, parabolic, exponential, sigmoid, power-low, and any combination thereof.

EXAMPLE 12

Plume Angle

In contrast to prior-art nasal delivery devices and technologies, the devices of the present invention can produce a fine aerosol in the nasal cavity or other desired body orifice at the target area and at the location of the target tissue instead of immediately after exit from the device. Utilizing the pressure as a driving force and the air as a carrier allows the material to be released from the nozzle as a combination of material in a pre-aerosolized state and an aerosol. The properties of the resultant aerosol are typically dependent on the properties of the device and of the medium into which the aerosol is discharged. The properties of the device which affect the aerosol characteristics are the delivery speed, the volume of the delivery gas, and the characteristics of the delivery orifice.

In some embodiments, the aerosol properties are fairly independent of the delivered substance, in other embodiments, the pressure, volume, orifice characteristics and delivered substance properties can be co-optimized.

In prior-art devices the aerosol is produced at the exit to the device. Typically, the aerosol comprises a wide dispersion of particle sizes, a wide "fan" of aerosol and a low driving force. Therefore, the large droplets typically deposit very close to the exit from the device; smaller droplets tend to quickly contact the walls of the passage, so that deposition is typically predominantly close to the exit from the device, with little of the substance reaching desired sites deeper in the orifice, such as the turbinates of the nose, In contrast, in the present device, the aerosol and pre-aerosolized mixture of gas and substance exits the device with a significant driving force, when the preaerosolized fluid hits the walls of the nasal passages, it "explodes" into a fine aerosol that is capable of being driven by the pressure deep into the nasal passages to deposit in the desired region.

In reference to FIG. 35, a schematic is shown of a nozzle and the aerosol it releases. The orifice emits an aerosol which forms a conical plume (1) with a distribution of particles (2) in it.

Figure 36A:
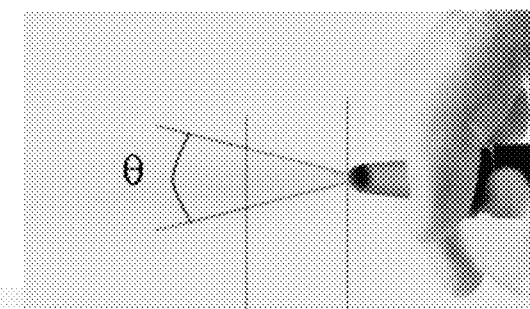

The plume angle is the total angle subtended by the plume, as shown by the angle α in FIG. 35 and by the angle θ subtended between the lines, as shown in FIG. 36A.

In FIG. 36, the plume angle θ is compared for 2 commercial nasal delivery devices (FIG. 36A-B) and the Sip-Nose device (FIG. 36C). Aerosol was measured at room temperature. The widths of the plumes were measured at the same distance (3 cm) from the discharge site in each device.

The SipNose device has a much narrower plume than the two commercial devices. The plume angles for the commercial devices, the Alrin™ from Teva (FIG. 36A) had a plume angle of 35°, the LMA MAD Nasal™ (FIG. 36B) had a plume angle of 27°, while the plume angle for the SipNose device (FIG. 36C) had a plume angle of only 8.7°.

All the above parameters allow the aerosol to better deposit in the area of interest—such as the area of the olfactory epithelium in the nasal cavity; and to be better absorbed by the target tissue such as the brain.

EXAMPLE 13

Plume Intensity

Figure 37A:
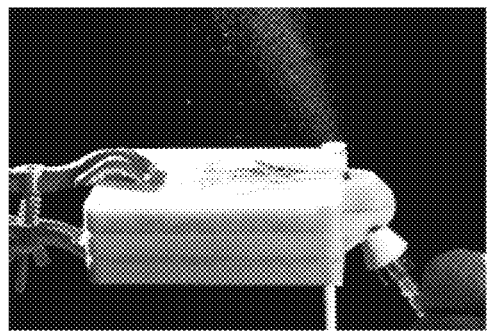
Figure 37B:
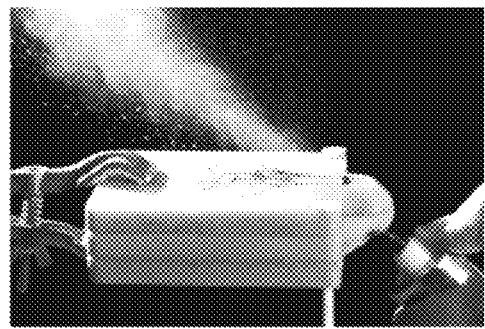

FIG. 37 compares the amount of material reaching the upper layers of the nasal model for one of the prior-art devices (commercial 2—LMA MAD Nasal™) and the device of the present invention (SipNose). In each case, 100 µl of liquid aerosol was discharged into a human nasal model (a nasal cast). The upper layer of the nasal cast was removed in order to observe the amount and characteristics of the aerosol that reaches the area of the upper portion of the nasal cavity. It is clear that there is a better distribution of the substance in the area of interest, the uppermost portions of the nasal cavities when the present invention technology is in use (FIG. 37B).

Figure 38:
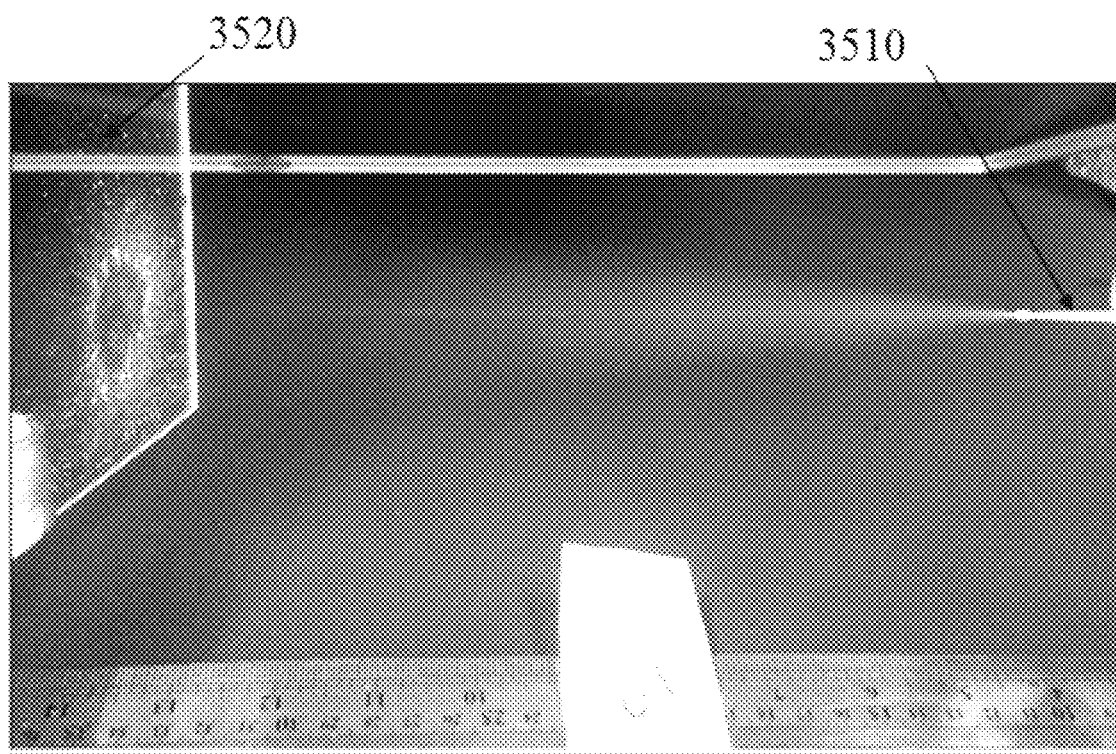

FIG. 38 shows an experimental setup for determining coverage of a spray plume. A device (3510) is at the left, and a screen for measuring coverage is at the right (3520). The distance between device and screen is about 25 cm.

FIGS. 39A-J show examples of spray coverage for different devices. FIGS. 39A-D show coverage and droplet distribution for the SipNose device for different device parameters, while FIGS. 39E-J show coverage and droplet distribution for a number of different commercial devices.

In all cases, the SipNose device produces a spray pattern covering a well-defined area of the screen. A large number of particles reach the screen and, in the coverage area, this is significantly more than for any of the commercial devices.

Commercial devices F and J are the best of the prior-art devices, with a reasonable amount of the aerosol reaching the screen, but the distribution is very much wider than for the SipNose device, covering virtually the entire screen. Commercial devices H and I are the worst of the prior-art devices, with very little of the aerosol even reaching as far as the screen.

Tables 11 and 12 show plume characteristics for the SipNose device for different operating parameters and an orifice size of 0.8 mm (Table 11) and for four commercial devices (Table 12).

TABLE 11

Plume Characteristics for the SipNose device

| Pressure (Bar) | Gas Volume $V_{gas}$ (ml) | Substance Volume $V_{sub}$ (ul) | Angle (°) | Height at 3 cm (mm) | Height at 6 cm (mm) | Velocity (m/s) |
|---|---|---|---|---|---|---|
| 2 | 8 | 500 | 15 | 10 | 16 | 23 |
| 6 | 8 | 500 | 20 | 12 | 18 | 15.8 |
| 6 | 19 | 100 | 15 | 10 | 21 | |
| 6 | 19 | 500 | 20 | 11 | 18 | |
| 2 | 5 | 100 | 9 | 10 | 12 | |
| 2 | 10 | 100 | 15 | 8 | 15 | |
| 2 | 5 | 500 | 17 | 18 | 20 | |
| 2 | 10 | 500 | 16 | 11 | 17 | 11.9 |
| 6 | 12 | 100 | 12 | 9 | 18 | |
| 6 | 6 | 500 | 12 | 5 | 6 | |
| 6 | 12 | 500 | 16 | 8 | 13 | |

TABLE 12

Plume Characteristics for the commercial devices

| Device | Pressure (Bar) | Gas Volume $V_{gas}$ (ml) | Substance Volume $V_{sub}$ (ul) | Angle (°) | Height at 3 cm (mm) | Height at 6 cm (mm) | Velocity (m/s) |
|---|---|---|---|---|---|---|---|
| MAD Nasal ™; | — | 6 | 100 | 35 | 18 | 30 | 2.3 |
| Wolfe Tory | — | 18 | 100 | 55 | 30 | 40 | |
| | — | 0 | 500 | 55 | 38 | 55 | |
| | — | 3 | 500 | 35 | 25 | 30 | |
| | — | 6 | 500 | 35 | 21 | 35 | 2.3 |
| | — | 18 | 500 | 33 | 20 | 29 | |
| Simply Saline Nasal Mist; Church & Dwight Co., Inc. | 7 | — | 500 | 45 | 37 | 53 | |
| Otrimer; Novartis | 7 | — | 500 | 35 | 20 | 33 | |
| Alrin, Teva | — | 0 | 100 | 35 | 26 | 33 | 3.3 |

Significant differences were seen between the properties of the plumes between the SipNose device and the commercial devices; small, if any, overlap was seen between the plume angles, the plume heights or the plume velocities. For the SipNose devices, the range of plume angles was 5° to 25°, the range of plume heights 3 cm from the device was 1 to 20 mm, the range of plume heights 6 cm from the device was 5 mm to 25 mm and the range of plume velocities was 5 m/s to 50 m/s. For the commercial devices, the plume angles were over 33°, the plume heights 3 cm from the device were over 18 mm, the plume heights 6 cm from the device were over 29 mm and the plume velocities were less than 5 m/s.

EXAMPLE 14

Brain Absorption

Figure 40:
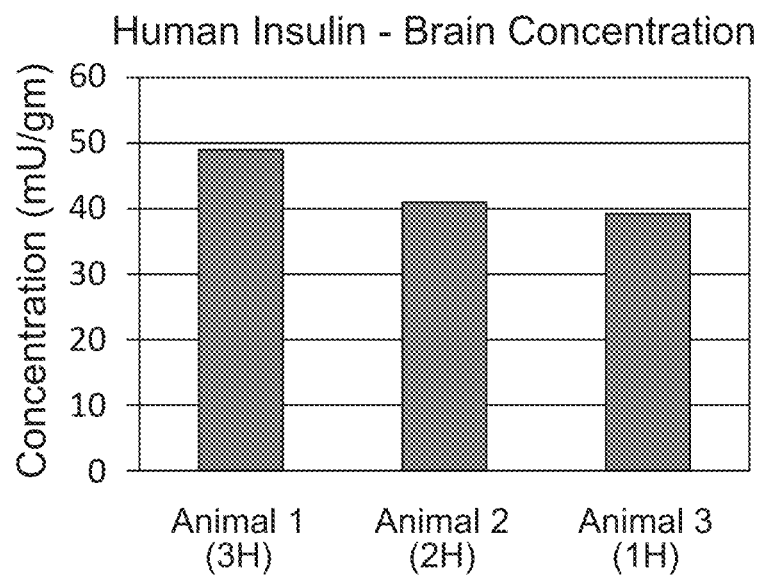

FIG. 40 demonstrates absorption of the desired substance into the brain as a function of time after administration. The substance in this experiment is Human Insulin (Lispro insulin, 5807 Da); the animal model is a rabbit. Administration was 10 U/Kg of Human Insulin via SipNose nasal administration. Brain concentrations were measured using insulin quantitative ELISA at 1 h, 2 h, and 3 h post administration.

Lispro Insulin is delivered to the brain with the SipNose device and can be specifically detected.

EXAMPLE 15

Blood and Brain Absorption

In FIG. 41, the efficacy of delivery of insulin to the brain is compared for the SipNose device vs. IV administration. The substance was Lispro insulin (5,807 Da) administered to rabbits. Four rabbits were used; all animals were given 0.5 U/kg of Human Insulin. Administration was via IV for rabbits 1 and 3 and via SipNose nasal administration for rabbits 2 and 4. Brain concentrations were measured using insulin quantitative ELISA.

Figure 41A:
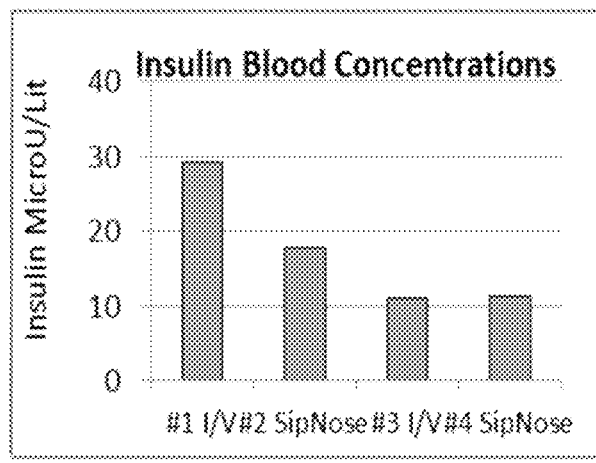
Figure 41B:
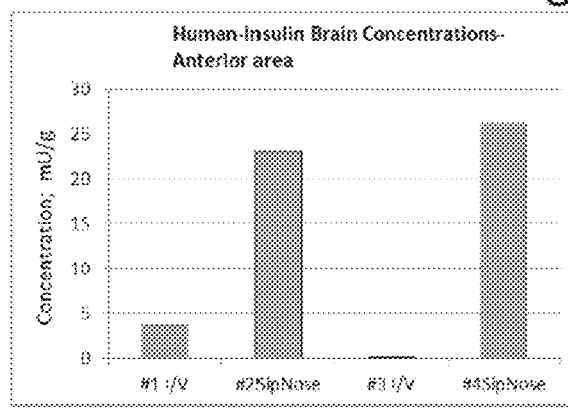
Figure 41C:
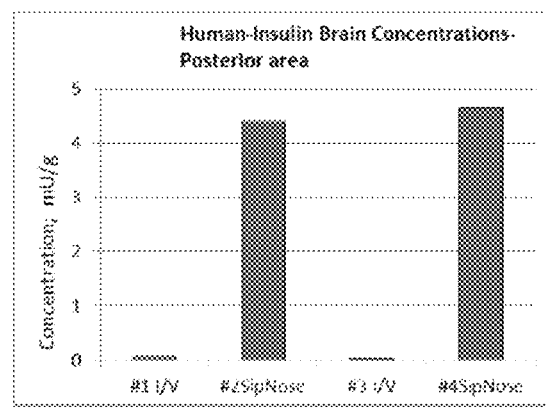

The results of the experiment are shown in FIGS. 41A-C. FIG. 41A shows the concentration of insulin in the blood for two animals that were given an IV administration (1 and 3) and two animals that were given nasal administration with the SipNose device (2 and 4). FIG. 41B shows the amount of insulin in the anterior part of the brain for the four animals and FIG. 41C shows the amount of insulin in the posterior part of the brain for the same four animals.

From FIG. 41A-C, the following conclusions can be drawn:
1. Lispro Insulin delivery to the brain with the SipNose device is highly efficient when compared to IN administration
2. Insulin delivery to the brain with the SipNose direct-nose-to-brain approach results in Insulin in both anterior and posterior parts of the brain.

EXAMPLE 16

Particle Size

Figure 42A:
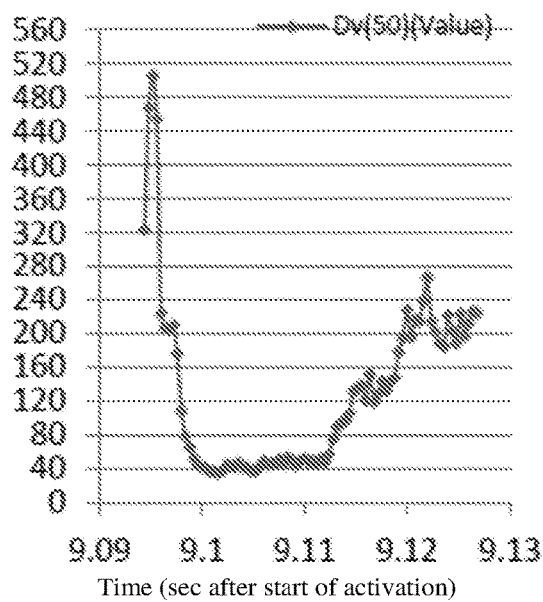
Figure 42B:
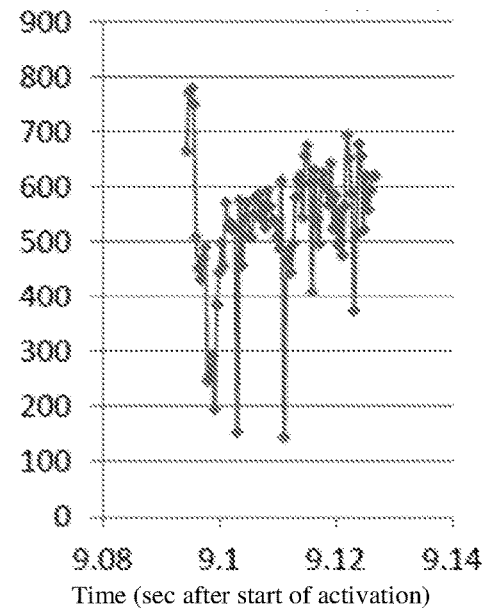
Figure 42C:
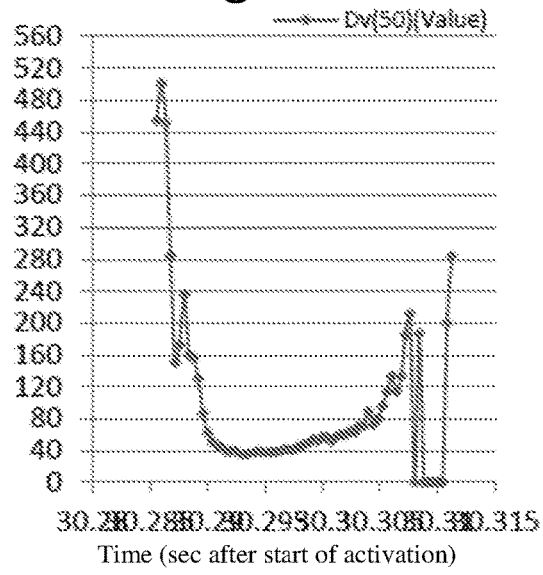
Figure 42D:
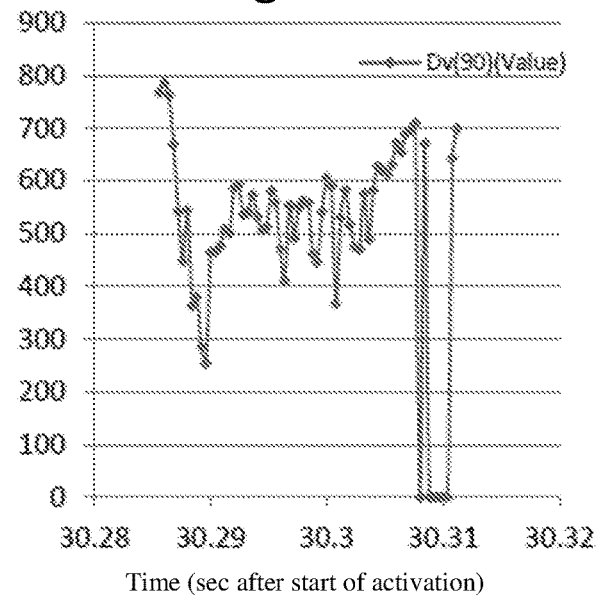

FIG. 42A-D shows the particle size as a function of time for an orifice diameter of 1.5 mm and a Saline volume of 100 ul. Two runs were made, the first shown in FIG. 42A-B, the second in FIG. 42C-D. The median particle size by volume (DV50 value) is shown in FIG. 42A and FIG. 42C, while the DV90 value, the particle volume larger than 90% of the particles, is shown in FIG. 42B and FIG. 42D. After a burst of large particles (LD 50 about 480-550 µm), the median particle size is 40-45 µm. The LD90 value is less consistent, but is in the range of about 500-600 µm.

Figure 43A:
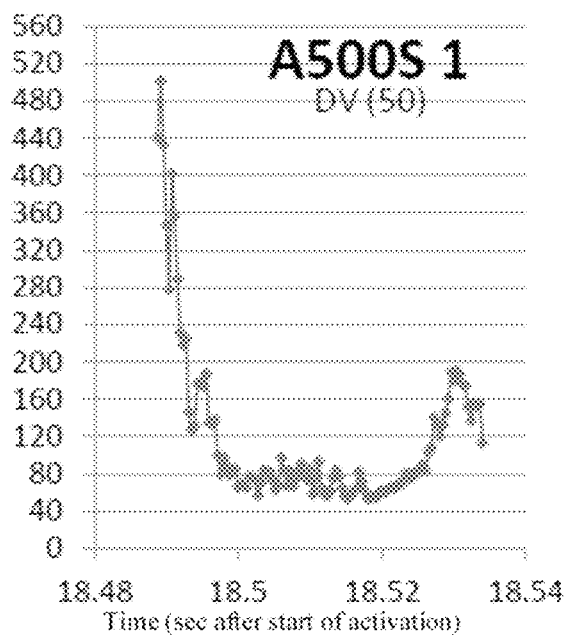
Figure 43B:
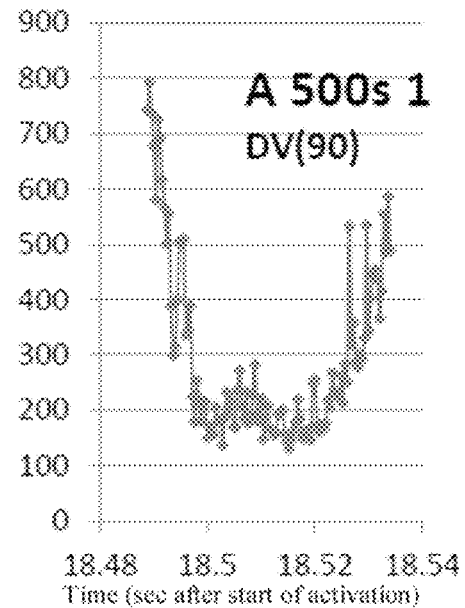
Figure 43C:
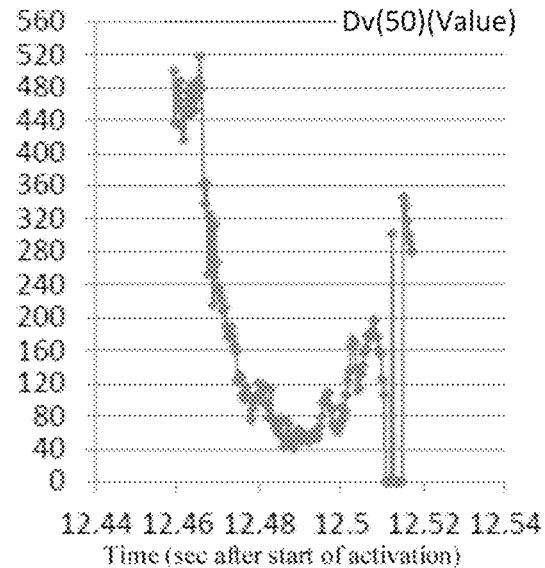
Figure 43D:
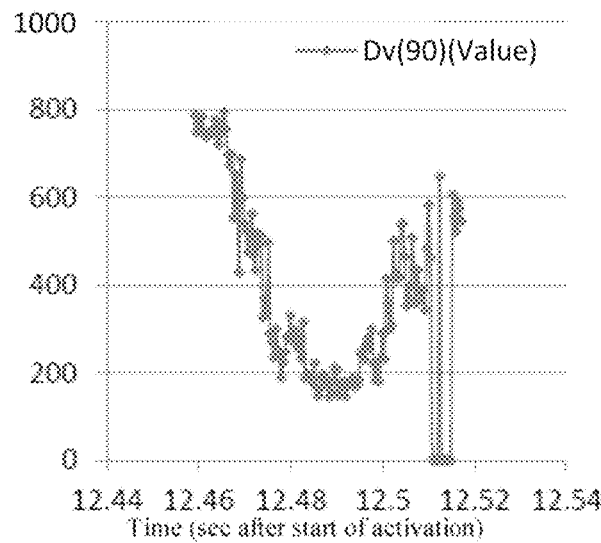

FIG. 43A-D shows the effect of time after activation on the particle size for an orifice diameter of 1.5 mm and a saline volume of 500 ul. Two runs were made, the first shown in FIG. 43A-B, the second in FIG. 43C-D. The median particle size by volume (DV50 value) is shown in FIG. 43A and FIG. 43C, while the DV90 value, the particle volume larger than 90% of the particles, is shown in FIG. 43B and FIG. 43D. After a burst of large particles (LD50 about 480-550 µm), the median particle size is about 50-65 µm. The LD90 value is less consistent, but is on the order of about 170 µm.

Figure 44A:
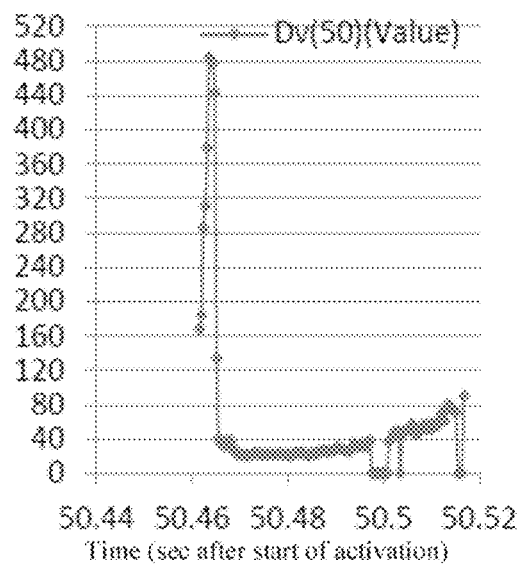
Figure 44B:
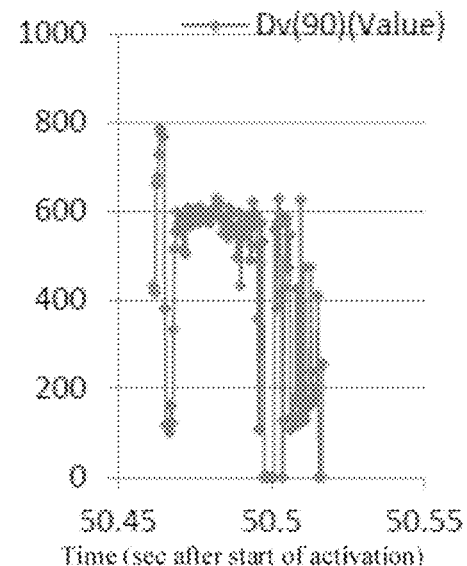
Figure 44C:
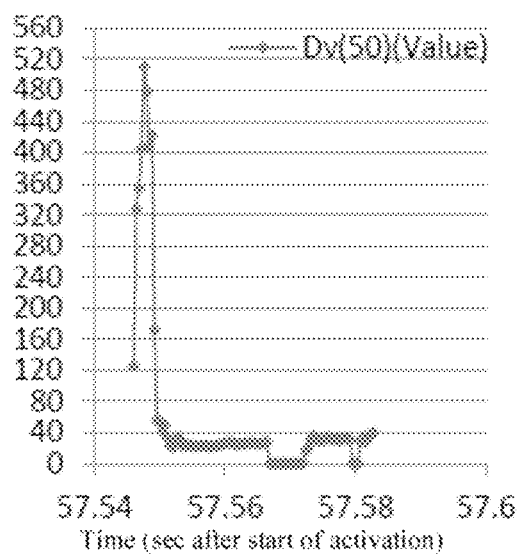
Figure 44D:
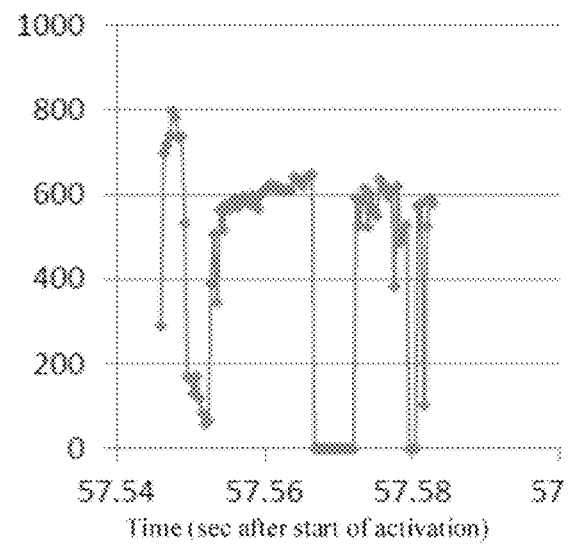

FIG. 44A-D shows the effect of time after activation on the particle size for an orifice diameter of 1.0 mm and a saline volume of 100 ul. Two runs were made, the first shown in FIG. 44A-B, the second in FIG. 44C-D. The median particle size by volume (DV50 value) is shown in FIG. 44A and FIG. 44C, while the DV90 value, the particle volume larger than 90% of the particles, is shown in FIG. 44B and FIG. 44D. After a burst of large particles (LD50 about 480-520 µm), the median particle size is about 25 µm. The LD90 value is less consistent, but is on the order of about 600 µm.

Figure 45A:
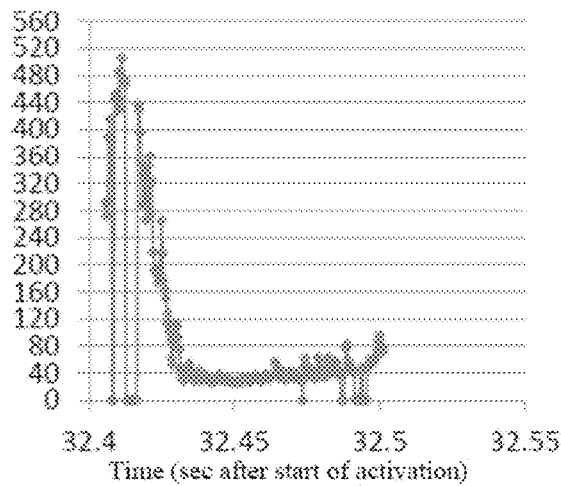
Figure 45B:
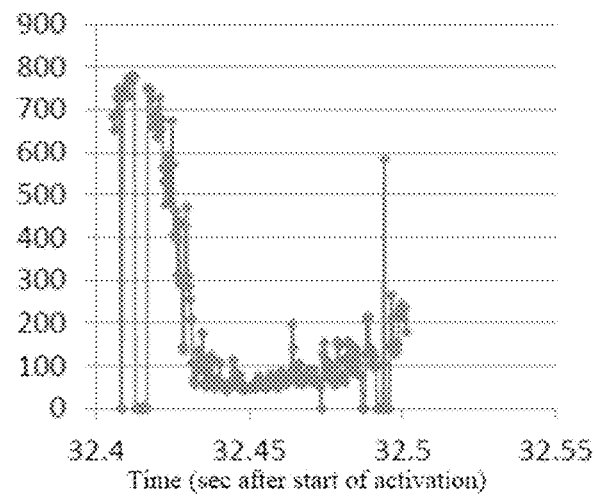
Figure 45C:
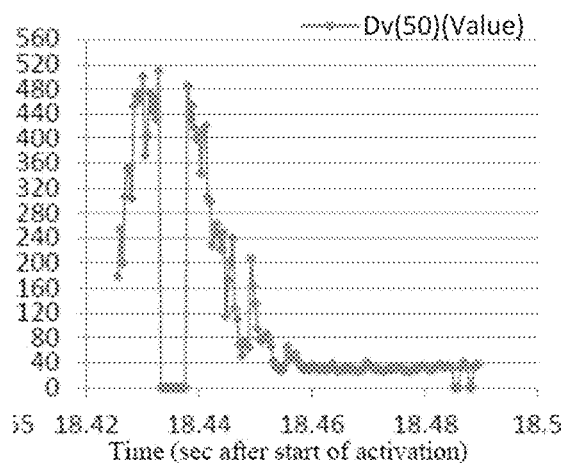
Figure 45D:
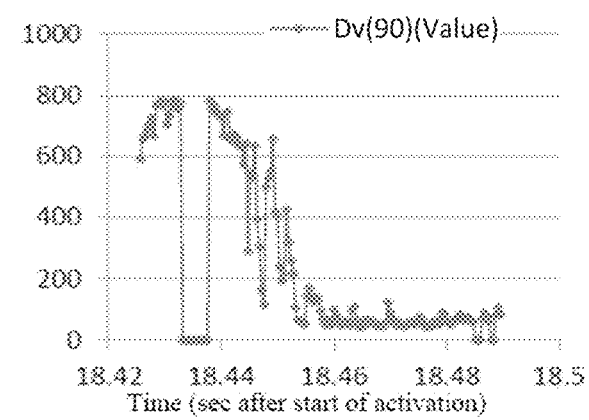

FIG. 45A-D shows the effect of time after activation on the particle size for an orifice diameter of 1.0 mm and a saline volume of 500 ul. Two runs were made, the first shown in FIG. 45A-B, the second in FIG. 45C-D. The median particle size by volume (DV50 value) is shown in FIG. 45A and FIG. 45C, while the DV90 value, the particle volume larger than 90% of the particles, is shown in FIG. 45B and FIG. 45D. After a burst of large particles (LD50 about 480-550 µm), the median particle size is about 28-30 µm. The LD90 value is less consistent, but, after a burst of large particle of volumes of 700-800 µm, is on the order of about 50 µm.

Figure 46A:
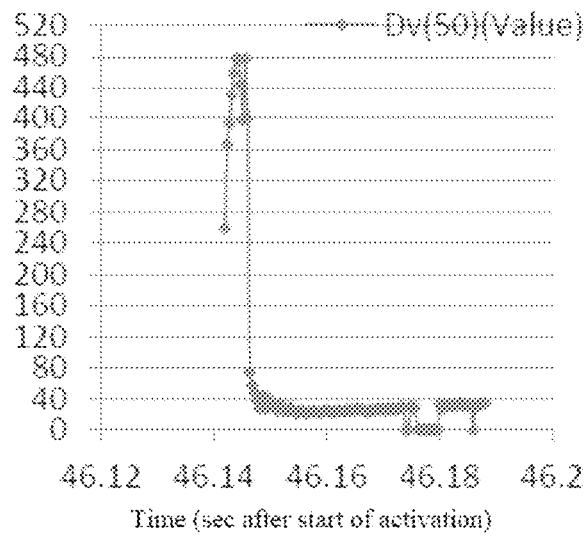
Figure 46B:
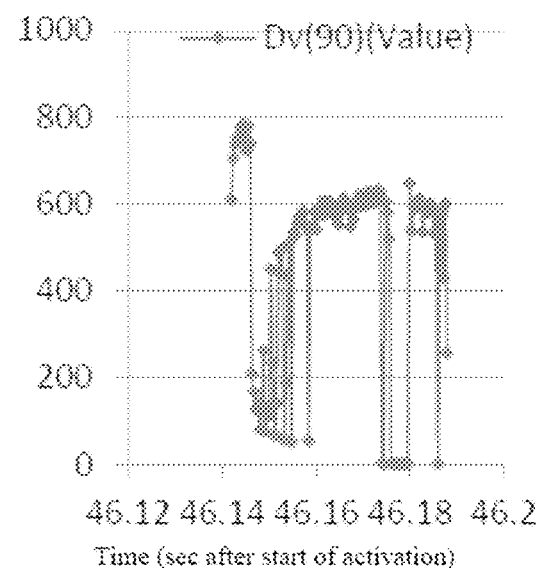
Figure 46C:
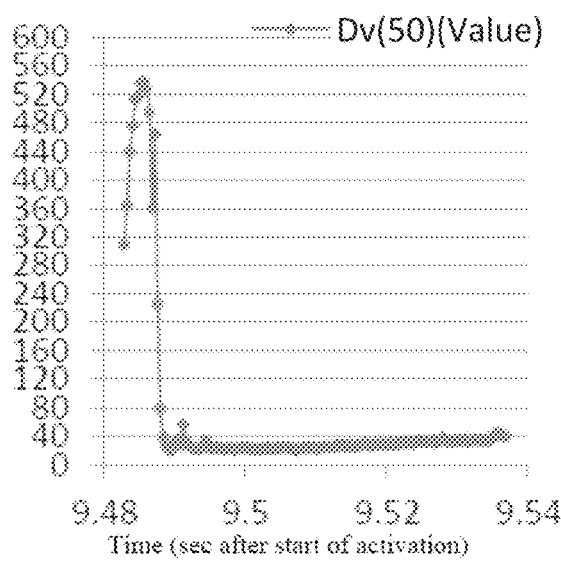
Figure 46D:
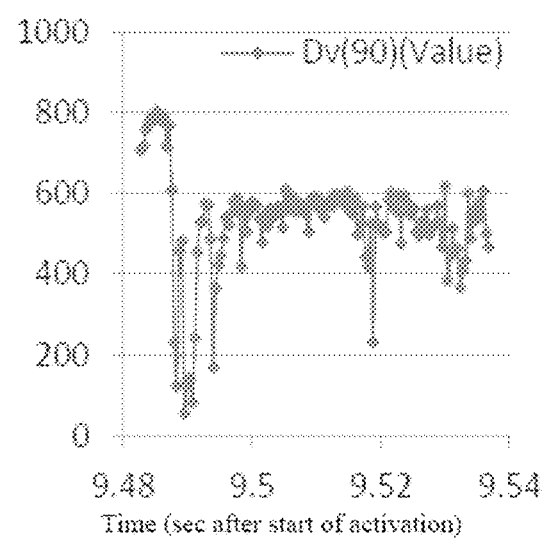

FIG. 46A-D shows the effect of time after activation on the particle size for an orifice diameter of 0.8 mm and a saline volume of 100 ul. Two runs were made, the first shown in FIG. 46A-B, the second in FIG. 46C-D. The median particle size by volume (DV50 value) is shown in FIG. 46A and FIG. 46C, while the DV90 value, the particle volume larger than 90% of the particles, is shown in FIG. 46B and FIG. 46D. After a burst of large particles (LD50 about 480-520 µm), the median particle size is about 23-24 µm. The LD90 value is less consistent, but is on the order of about 600 µm.

Figure 47A:
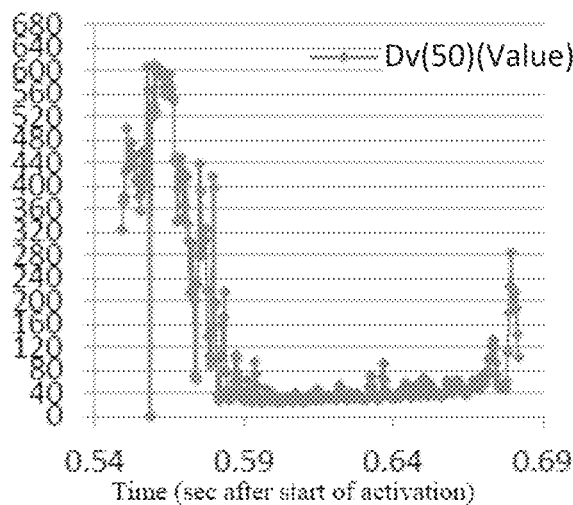
Figure 47B:
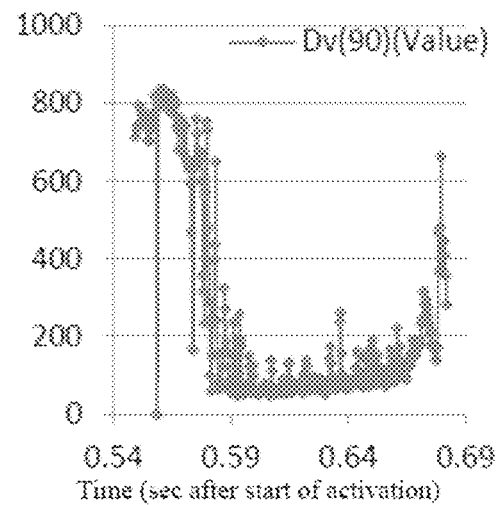
Figure 47C:
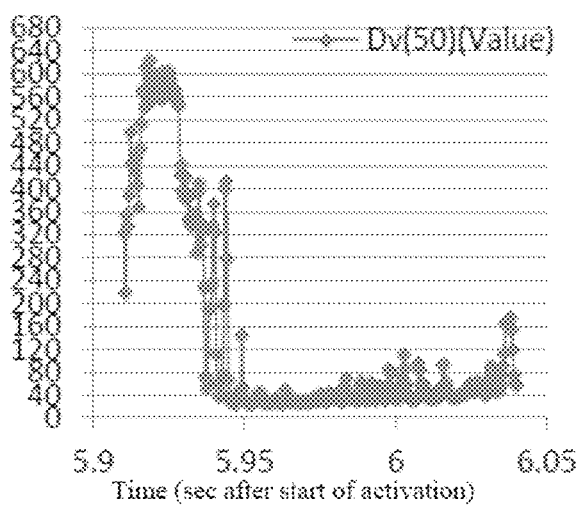
Figure 47D:
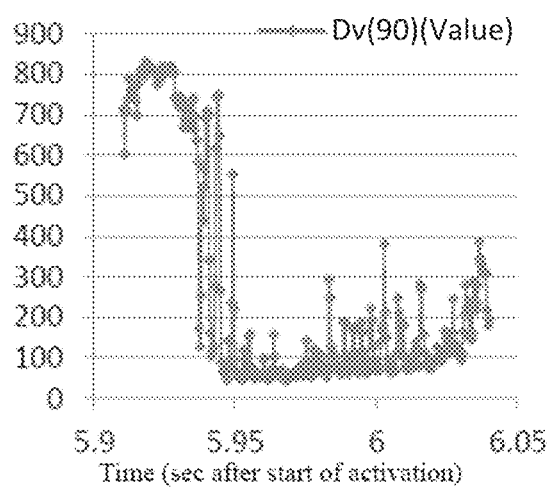

FIG. 47A-D shows the effect of time after activation on the particle size for an orifice diameter of 0.8 mm and a saline volume of 500 ul. Two runs were made, the first shown in FIG. 47A-B, the second in FIG. 47C-D. The median particle size by volume (DV50 value) is shown in FIG. 47A and FIG. 47C, while the DV90 value, the particle volume larger than 90% of the particles, is shown in FIG. 47B and FIG. 47D. After a burst of large particles (LD50 about 550-650 µm), the median particle size is about 32-35 µm. The LD90 value is less consistent, but, after a burst of large particle of volumes of 700-800 µm, is on the order of about 60-65 µm.

Figure 48A:
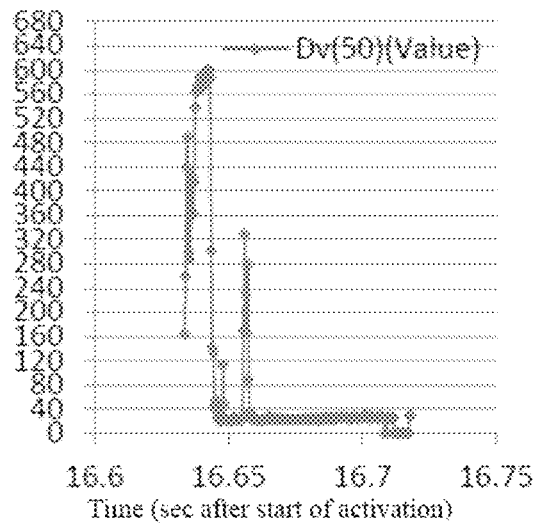
Figure 48B:
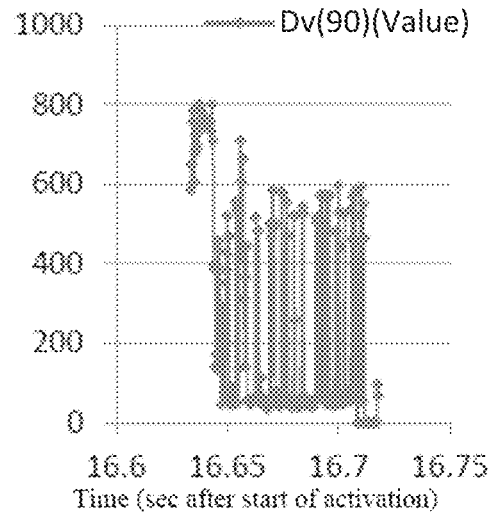
Figure 48C:
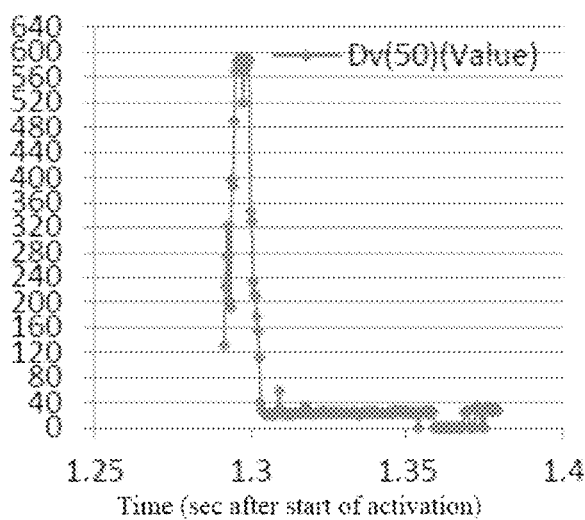
Figure 48D:
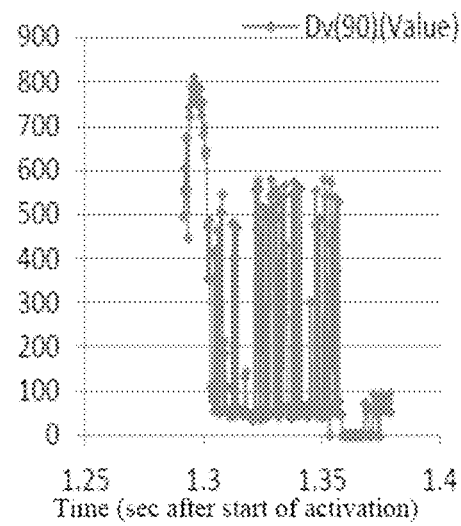

FIG. 48A-D shows the effect of time after activation on the particle size for an orifice diameter of 0.5 mm and a saline volume of 100 ul. Two runs were made, the first shown in FIG. 48A-B, the second in FIG. 48C-D. The median particle size by volume (DV50 value) is shown in FIG. 48A and FIG. 48C, while the DV90 value, the particle volume larger than 90% of the particles, is shown in FIG. 48B and FIG. 48D. After a burst of large particles (LD50 about 550-600 µm), the median particle size is about 23 µm. The LD90 value is less consistent, but, after a burst of large particle of volumes of 700-800 µm, is on the order of about 55 µm.

Figure 49A:
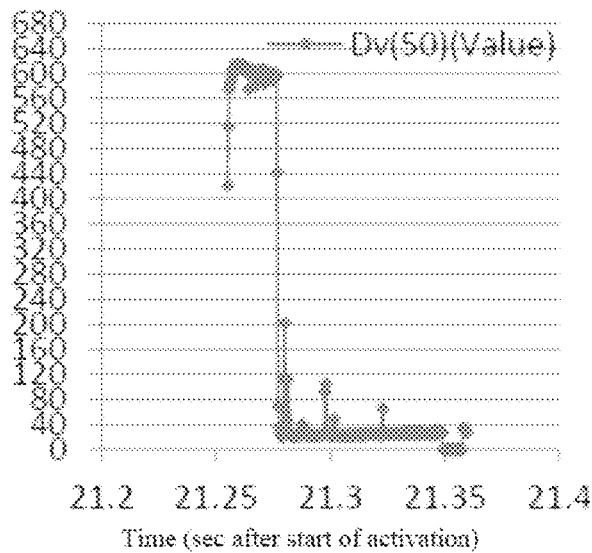
Figure 49B:
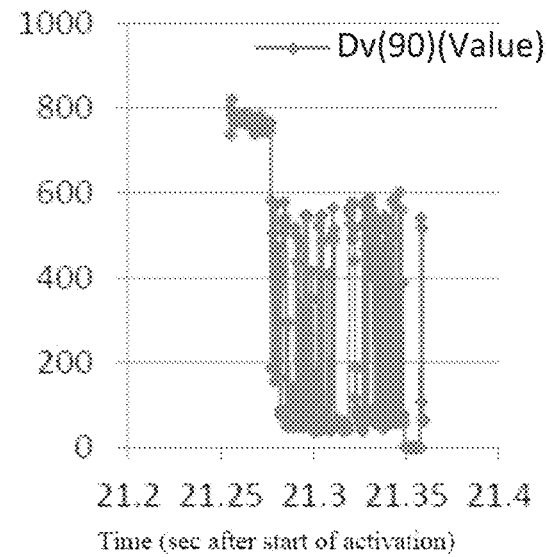
Figure 49C:
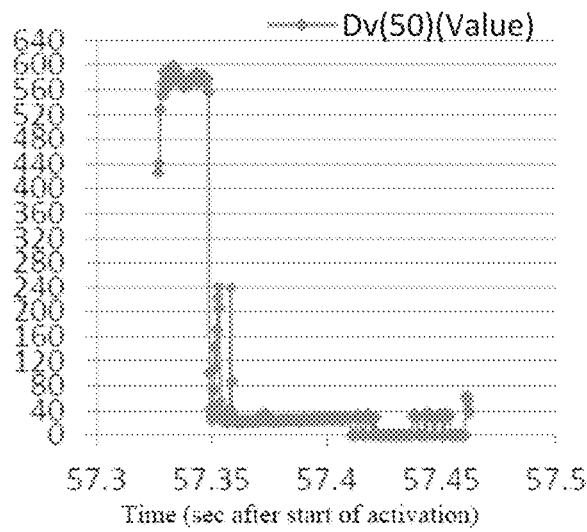
Figure 49D:
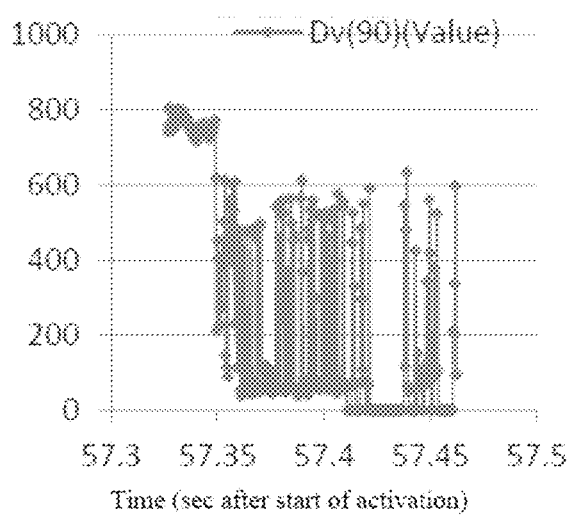

FIG. 49A-D shows the effect of time after activation on the particle size for an orifice diameter of 0.5 mm and a saline volume of 200 ul. Two runs were made, the first shown in FIG. 49A-B, the second in FIG. 49C-D. The median particle size by volume (DV50 value) is shown in FIG. 49A and FIG. 49C, while the DV90 value, the particle volume larger than 90% of the particles, is shown in FIG. 49B and FIG. 49D. After a burst of large particles (LD50 about 550-650 µm), the median particle size is about 25 µm. The LD90 value is less consistent, but, after a burst of large particles of volumes of 700-800 µm, is on the order of about 55-60 µm.

Figure 50A:
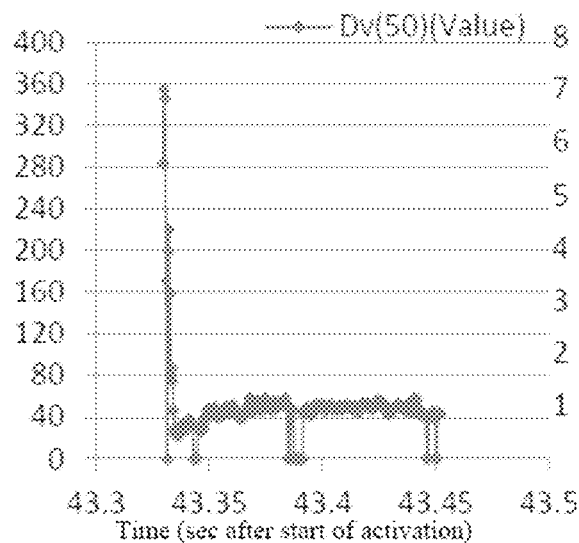
Figure 50B:
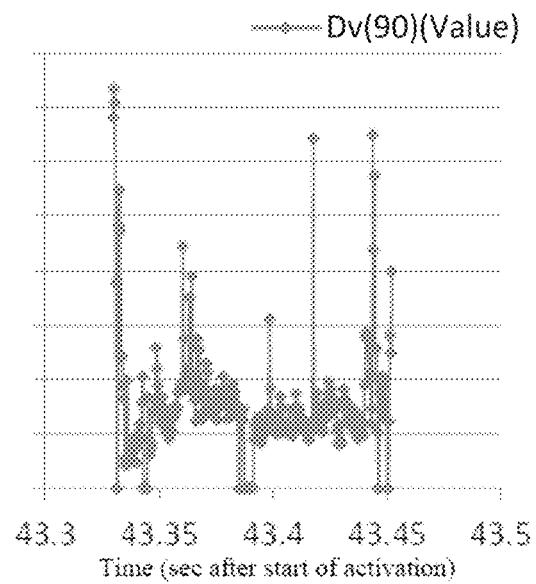
Figure 50C:
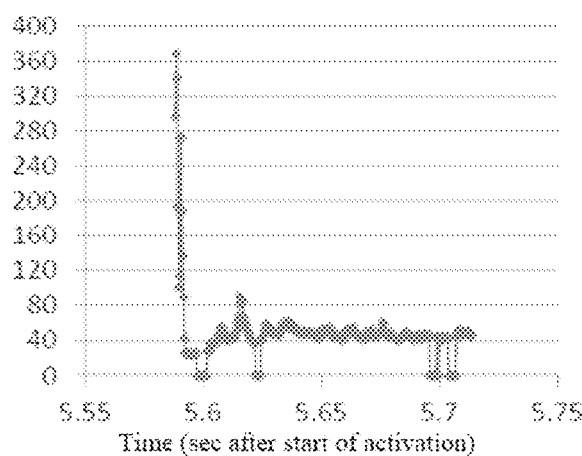
Figure 50D:
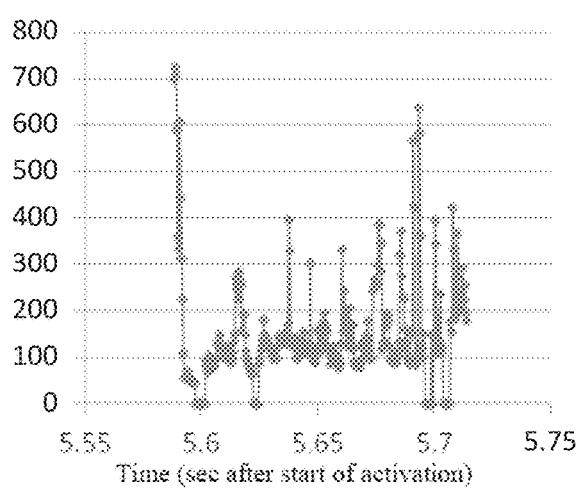

FIG. 50A-D shows the effect of time after activation on the particle size for a SipNose device with no orifice and a saline volume of 300 ul. Two runs were made, the first shown in FIG. 50A-B, the second in FIG. 50C-D. The median particle size by volume (DV50 value) is shown in FIG. 50A and FIG. 50C, while the DV90 value, the particle volume larger than 90% of the particles, is shown in FIG. 50B and FIG. 50D. After a small burst of large particles (LD 50 about 360-400 µm), the median particle size is about 45-48 μm. The LD90 value is less consistent, but, after a burst of large particle of volumes of 700-800 μm, is on the order of about 100-140 μm.

Figure 51A:
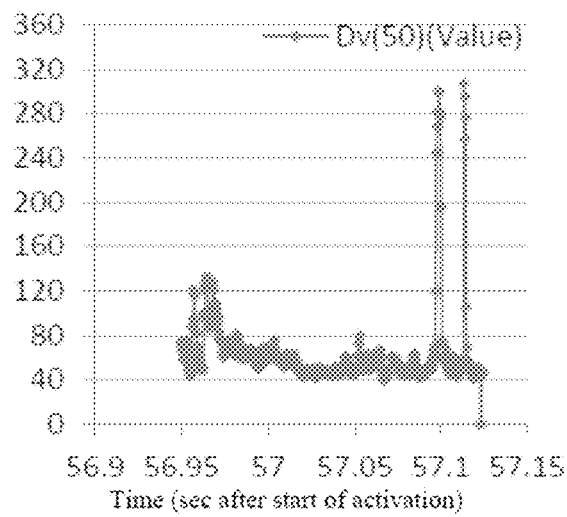
Figure 51B:
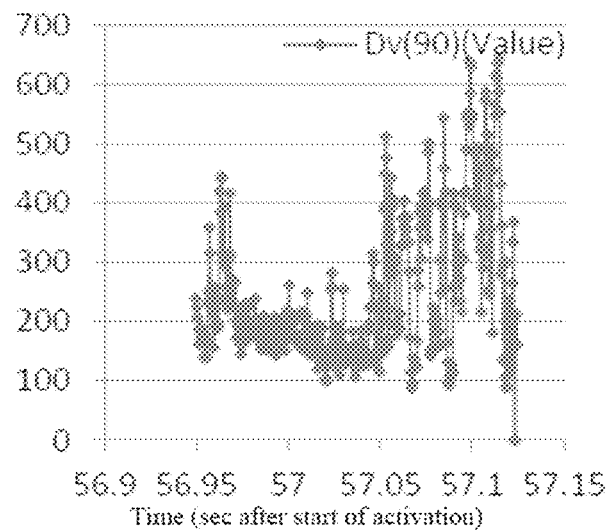
Figure 51C:
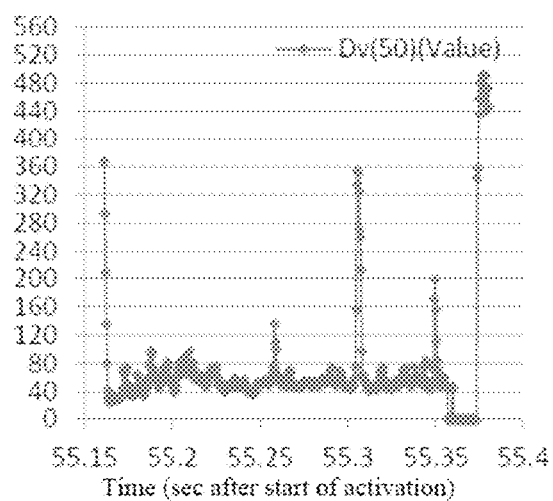
Figure 51D:
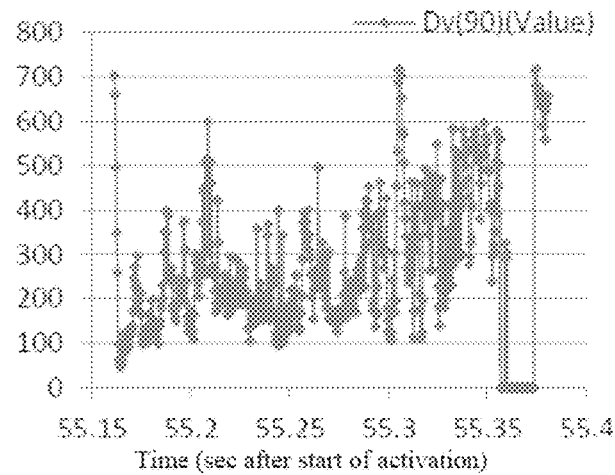

FIG. 51A-D shows the effect of time after activation on the particle size for a SipNose device with no orifice and a saline volume of 1000 ul. Two runs were made, the first shown in FIG. 51A-B, the second in FIG. 51C-D. The median particle size by volume (DV52 value) is shown in FIG. 51A and FIG. 51C, while the DV90 value, the particle volume larger than 90% of the particles, is shown in FIG. 51B and FIG. 51D. The median particle size is about 45-50 μm. The LD90 value is very inconsistent but is on the order of about 180 μm.

Figure 52A:
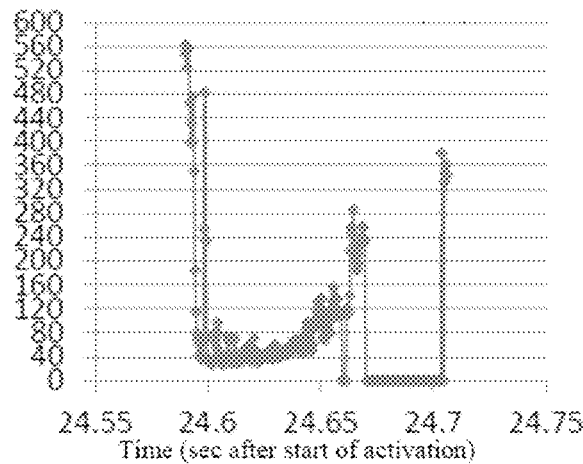
Figure 52B:
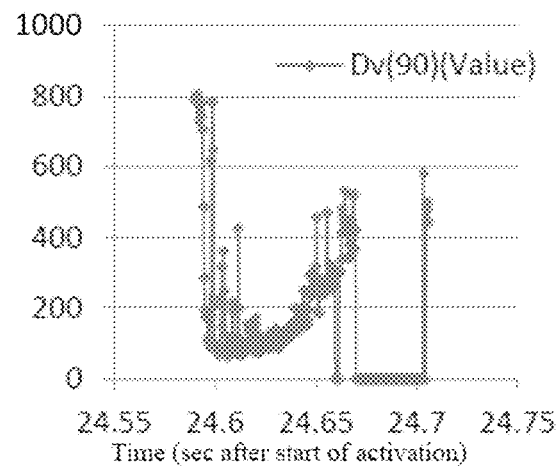
Figure 52C:
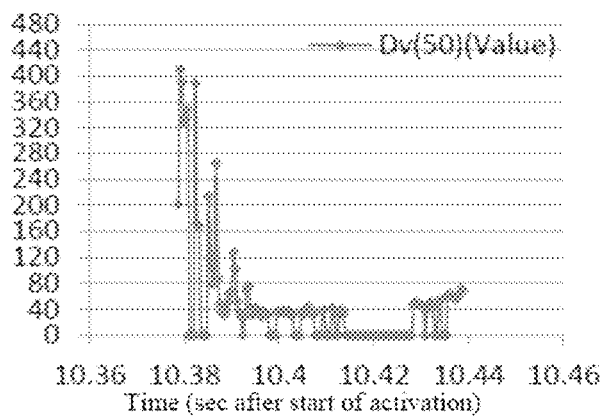
Figure 52D:
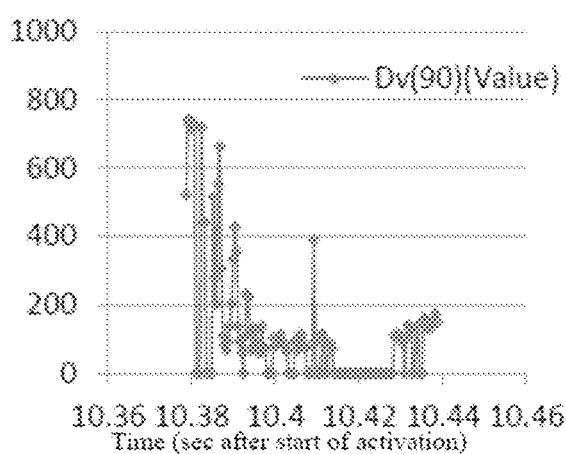

FIG. 52A-D shows the effect of time after activation on the particle size at a gas pressure of 3 barg, for an orifice diameter of 0.8 mm and a saline volume of 100 ul. Two runs were made, the first shown in FIG. 52A-B, the second in FIG. 52C-D. The median particle size by volume (DV50 value) is shown in FIG. 52A and FIG. 52C, while the DV90 value, the particle volume larger than 90% of the particles, is shown in FIG. 52B and FIG. 52D. After a small number of large particles (LD 50 about 400-560 μm), the median particle size is about 35-40 μm. The LD90 value is less consistent, but is on the order of about 90-100 μm.

Figure 53A:
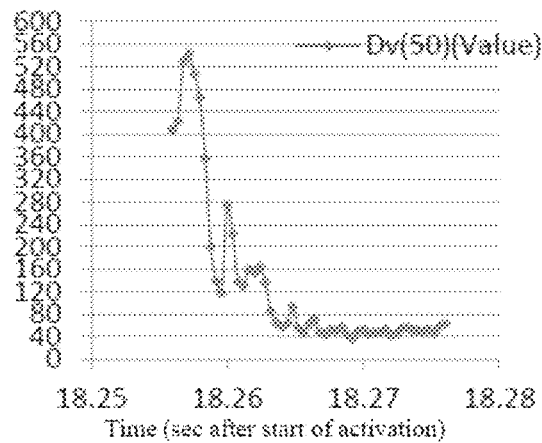
Figure 53B:
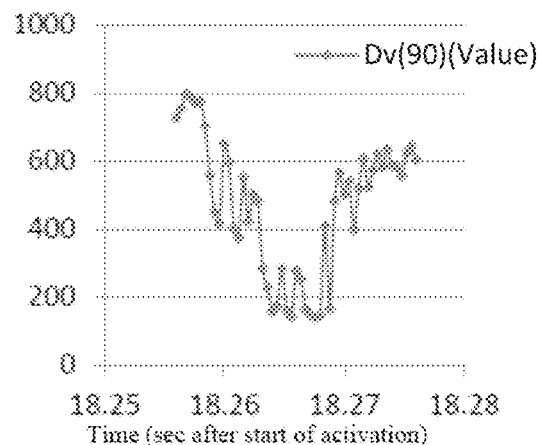
Figure 53C:
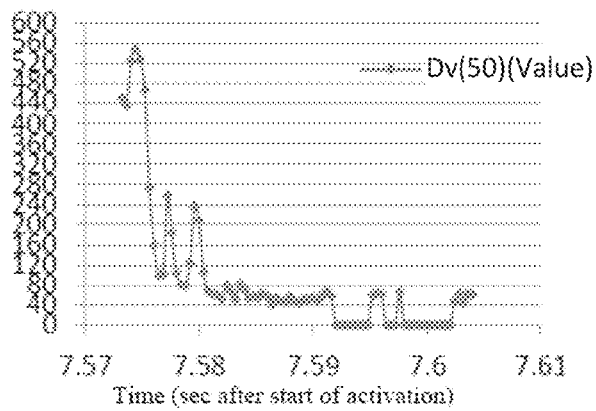
Figure 53D:
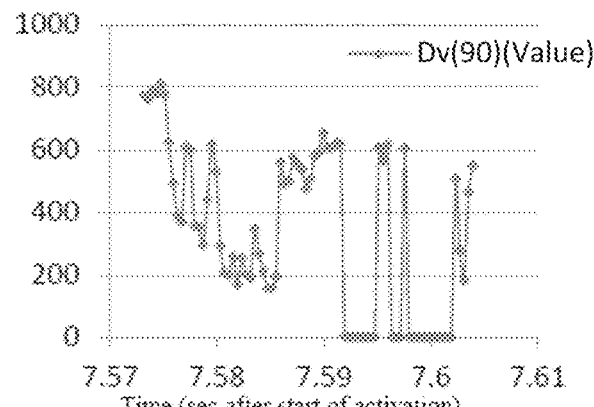

FIG. 53A-D shows the effect of time after activation on the particle size for a high viscosity substance, Otrivine™ with a viscosity of 23 cP, using the SipNose device with an orifice of 1 mm. Two runs were made, the first shown in FIG. 53A-B, the second in FIG. 53C-D. The median particle size by volume (DV50 value) is shown in FIG. 53A and FIG. 53C, while the DV90 value, the particle volume larger than 90% of the particles, is shown in FIG. 53B and FIG. 53D. After a small burst of large particles (LD 50 about 520-560 μm), the median particle size is about 45-48 μm. The LD90 value is very inconsistent, but is on the order of about 300 μm.

Figure 54A:
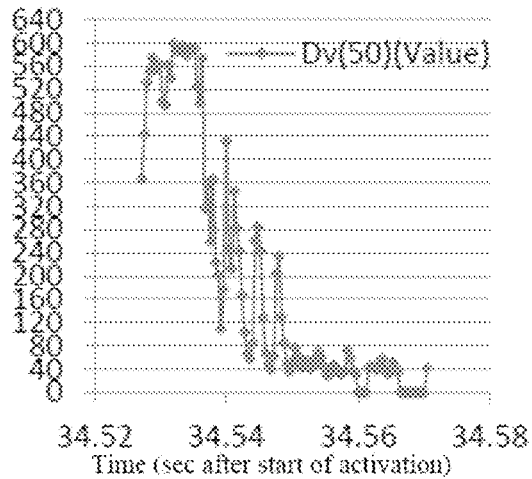
Figure 54B:
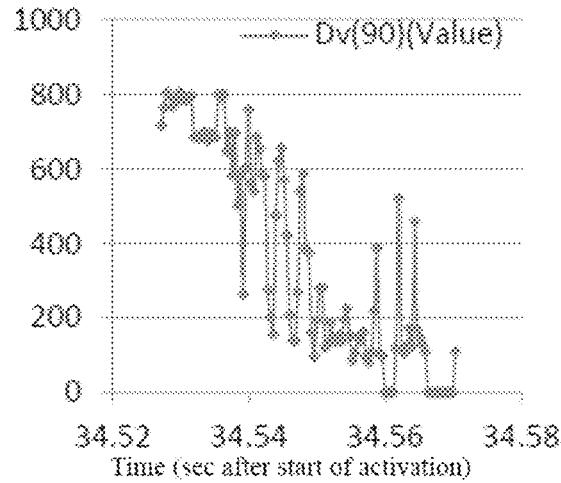
Figure 54C:
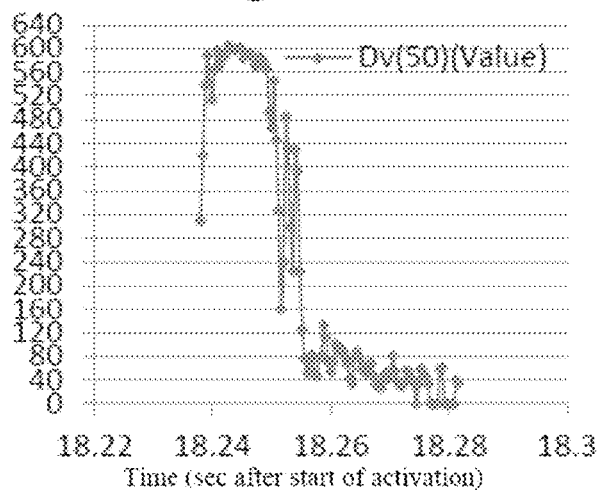
Figure 54D:
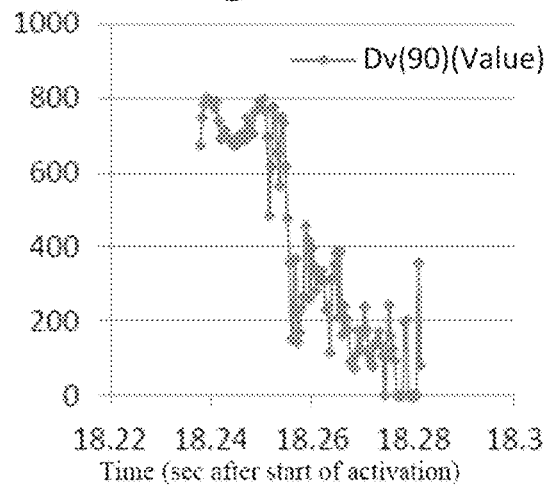
Figure 55A:
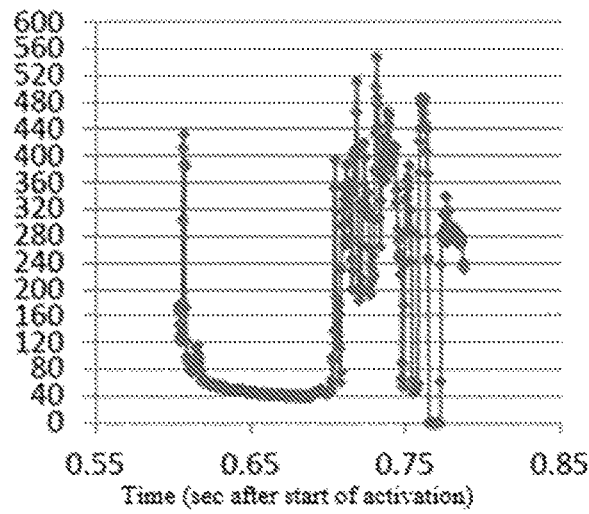
Figure 55B:
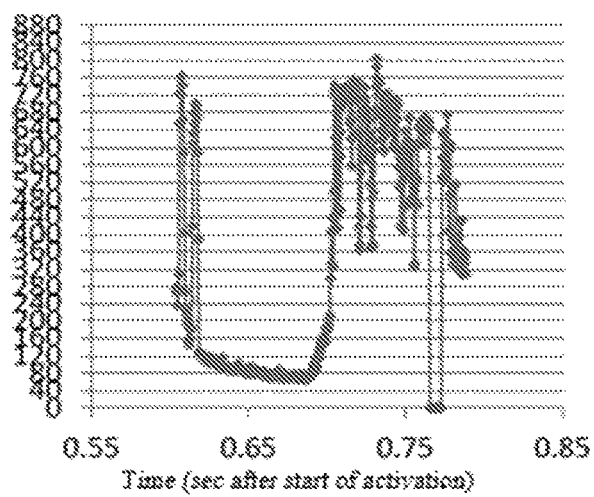
Figure 55C:
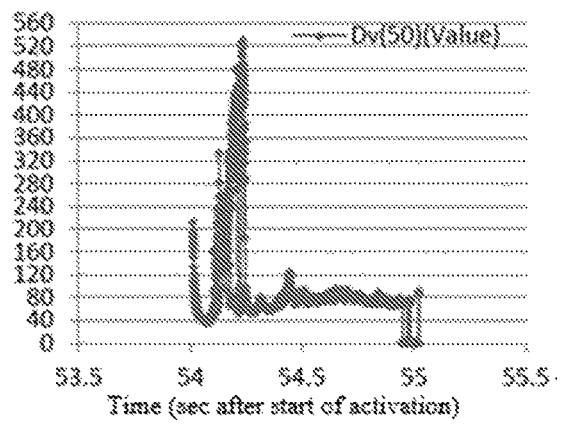
Figure 55D:
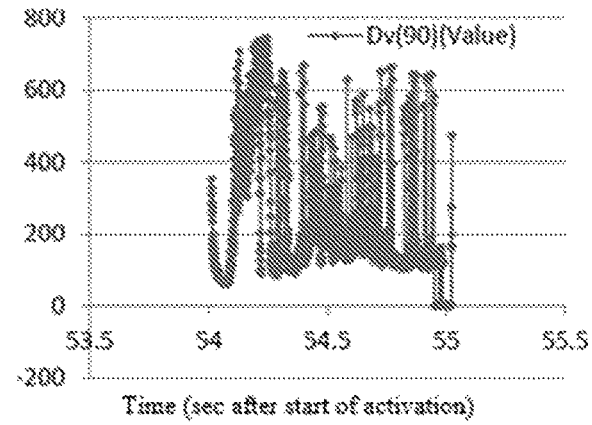
Figure 56:
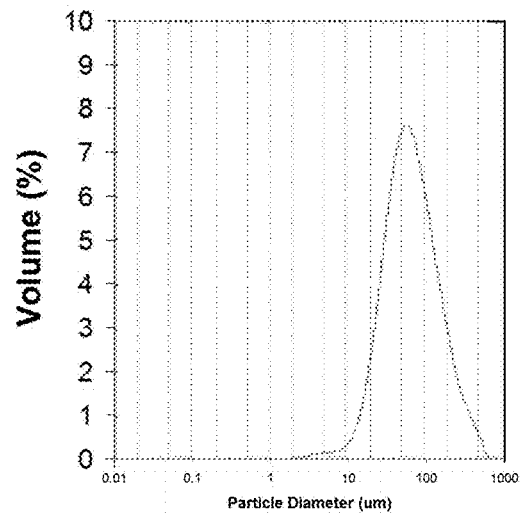
FIG. 56 shows a typical particle size distribution.
Figure 57:
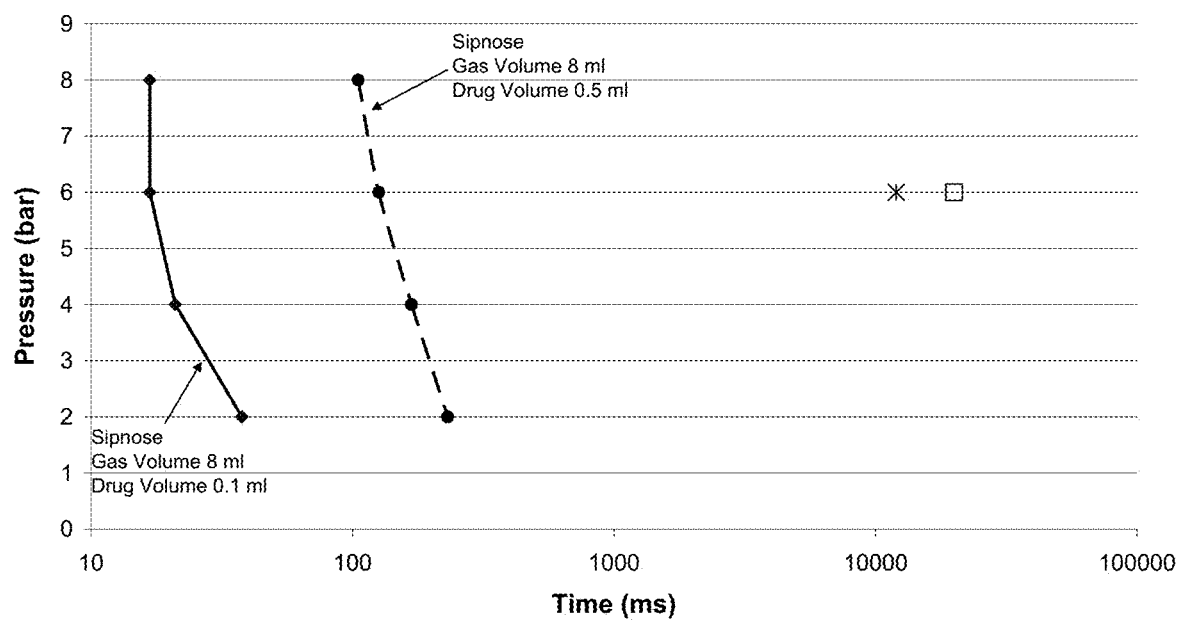
FIGS. 57-59 show the effect of various parameters on emptying time
Figure 58:
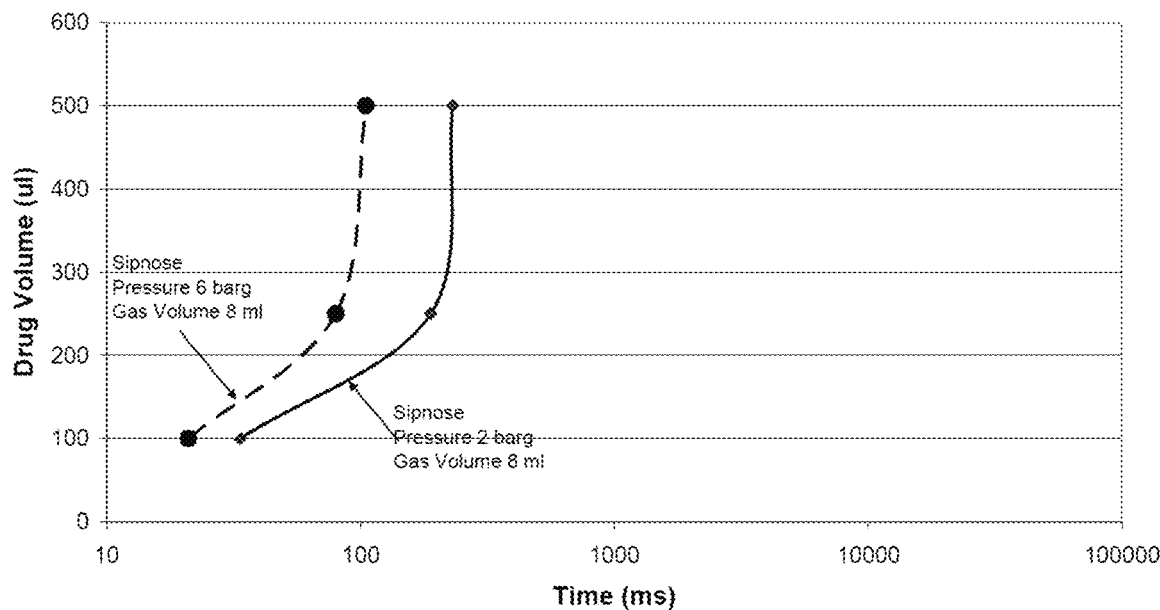
Figure 59:
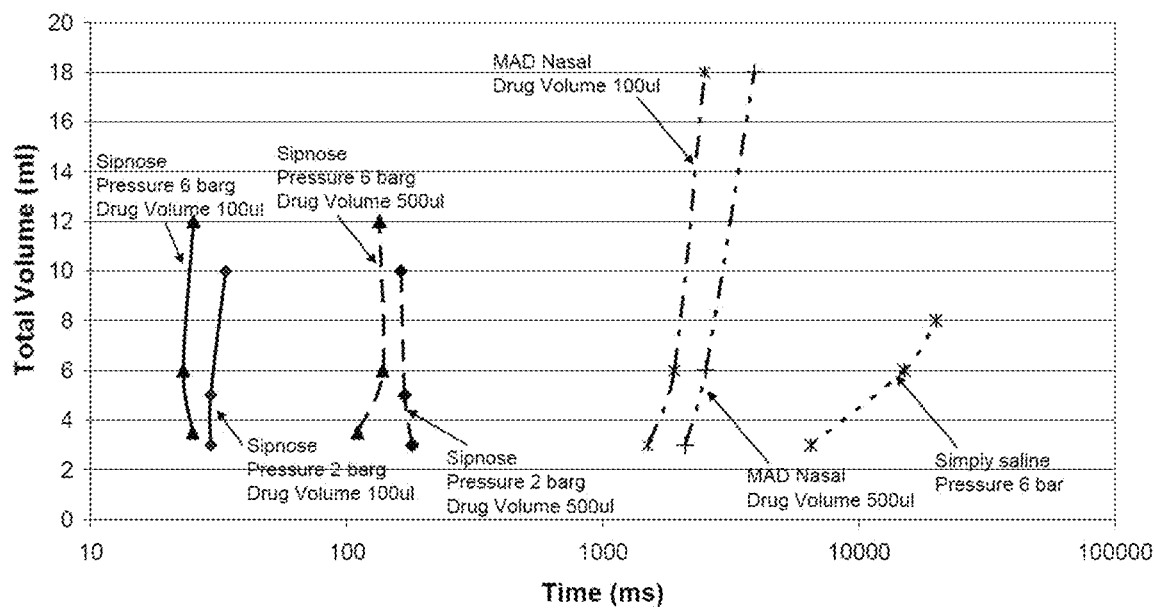

FIG. 54A-D shows the effect of time after activation on the particle size for a high viscosity substance, Otrivine™ with a viscosity of 23 cP, using the SipNose device with an orifice of 0.5 mm. Two runs were made, the first shown in FIG. 54A-B, the second in FIG. 54C-D. The median particle size by volume (DV50 value) is shown in FIG. 54A and FIG. 54C, while the DV90 value, the particle volume larger than 90% of the particles, is shown in FIG. 54B and FIG. 54D. The particle sizes are less consistent than they were with the 1 mm diameter orifice. After a small burst of large particles (LD 50 about 560-600 μm), the median particle size is about 40-55 μm. The LD90 value is very inconsistent.

FIG. 55A-D shows the effect of time after activation on the particle size for the Alrin™ prior-art device. The Alrin™ device, like the SipNose device, was hand activated. The particle sizes for the Alrin™ device have less run-to-run consistency than was seen for the SipNose device. The median particle size for the Alrin™ device is about 40-70 μm, while the DV90 particle size is about 65-120 μm.

These results are summarized in Table 13.

TABLE 13

Effect of various Parameters on Particle Size

| Device | Pressure (barg) | Orifice Size (mm) | Medicament | Medicament Volume (μl) | DV50 (μm) | DV90 (μm) |
|---|---|---|---|---|---|---|
| SipNose | 6 | 1.5 | Saline | 100 | 40-45 | — |
| SipNose | 6 | 1.5 | Saline | 500 | 50-65 | — |
| SipNose | 6 | 1.0 | Saline | 100 | 25 | — |
| SipNose | 6 | 1.0 | Saline | 500 | 28-30 | 50 |
| SipNose | 6 | 0.8 | Saline | 100 | 23-24 | — |
| SipNose | 6 | 0.8 | Saline | 500 | 32-35 | 60-65 |
| SipNose | 6 | 0.5 | Saline | 100 | 23 | 55 |
| SipNose | 6 | 0.5 | Saline | 200 | 25 | 55-60 |
| SipNose | 6 | 0.5 | Saline | 500 | 27, 30, 35 | 55, 55, 65 |
| SipNose | 6 | No orifice | Saline | 300 | 45-48 | 100-140 |
| SipNose | 6 | No orifice | Saline | 1000 | 50 | 180 |
| SipNose | 3 | 0.8 | Saline | 100 | 35-40 | 90-100 |
| SipNose | 6 | 1 | Otrivine™ (23 cP viscosity) | 100 | 45-48 | — |
| SipNose | 6 | 0.5 | Otrivine™ (23 cP viscosity) | 100 | 40-55 | — |
| Alrin™ | — | — | Saline | 100 | 45, 40, 70 | 70, 65, 120 |

SipNose aerosol droplets have a mean diameter in the typical range of other nasal delivery devices, and even smaller. Replacement of the saline with a high viscosity solution of 23 cP appears to have made little difference to the particle size distribution.

For the range of parameters used, the delivery parameters appear to have little effect on the particle size.

An example of the droplet size distribution is given in FIG. 56, which shows a plot of the number of particles vs. particle size, with the X axis (particle size) being logarithmic. The distribution is asymmetrical, having a long "tail" on the large-diameter side. The largest droplets are on the order of 900 μm, with the smallest particles being on the order of a 2-5 μm. The DV50 diameter is about 75 μm.

Tables 14 and 15 show droplet size distributions averaged over 10 repeats for 100 ul and 400 ul saline in two SipNose devices (23-11 for 100 ul and 23-12 for 400 ul) for parameters 6 barg pressure, 19 ml of gas, and 0.8 mm orifice diameter. In all cases shown, low variability was seen for the 10 repeats of the measurements.

TABLE 14

Device 23-11

| Device Version | D v (0, 0.5) (μm) | Obscuration (%) |
|---|---|---|
| 23-11 | 73.0 | 1.3 |
| 23-11 | 70.6 | 1.5 |
| 23-11 | 78.8 | 0.9 |
| 23-11 | 86.6 | 1.2 |
| 23-11 | 74.2 | 1.3 |
| 23-11 | 88.7 | 1.0 |
| 23-11 | 64.9 | 1.2 |
| 23-11 | 86.7 | 1.3 |
| 23-11 | 55.3 | 1.2 |
| 23-11 | 58.3 | 1.1 |
| Mean | 73.7 ± 11.8 | |

TABLE 15

Device 23-12

| Device Version | D v (0, 0.5) (μm) | Obscuration (%) |
|---|---|---|
| 23-12 | 68.7 | 3.8 |
| 23-12 | 83.5 | 2.4 |
| 23-12 | 81.7 | 4.8 |
| 23-12 | 71.4 | 22.9* |
| 23-12 | 92.1 | 3.3 |
| 23-12 | 83.8 | 4.3 |
| 23-12 | 83.3 | 5.3 |
| 23-12 | 100.6 | 3.4 |
| 23-12 | 100.8 | 2.8 |
| 23-12 | 92.3 | 6.4 |
| 23-12 | 108.6 | 3.4 |
| Mean | 88.3 ± 12.9 | |

*anomalous value

Table 16 shows an example of the reproducibility for the SipNose device. The measurements were done by weighing, and part of the variability shown probably depends on the measurement technique.

TABLE 16

Reproducibility for a SipNose device

| | Amount loaded (gm) | Residual amount (gm) | Released (%) | Residual volume (%) |
|---|---|---|---|---|
| 1 | 0.3996 | 0.0584 | 85.4 | 14.6 |
| 2 | 0.4058 | 0.0414 | 89.8 | 10.2 |
| 3 | 0.3915 | 0.0054 | 98.6 | 1.4 |
| 4 | 0.4143 | 0.0063 | 98.5 | 1.5 |
| 5 | 0.3772 | 0.0069 | 98.2 | 1.8 |
| 6 | 0.3902 | 0.0509 | 87.0 | 13.0 |
| 7 | 0.4010 | 0.0626 | 84.4 | 15.6 |
| 8 | 0.3853 | 0.0490 | 87.3 | 12.7 |
| 9 | 0.4302 | 0.0511 | 88.1 | 11.9 |
| 10 | 0.4052 | 0.0482 | 88.1 | 11.9 |
| Average | 0.4000 | 0.0380 | 90.5 | 9.5 |
| Std. Dev. | 0.0152 | 0.0227 | 5.6 | 5.6 |

SipNose aerosol droplets have a mean diameter in the typical range of other nasal delivery devices, and even smaller.

Although the droplets have a small diameter, the width of the aerosol plume is very narrow, and this allows the aerosol to be better distributed in the inner part of the nasal cavity, without depositing at the front of a cavity such as the nasal cavity.

The SipNose device shows high consistency

EXAMPLE 17

Effect of Pressure on Release Time

In reference to FIG. 57, the effect of gas pressure on emptying/release time for 8.1 ml or 8.5 ml (of gas+substance) was tested. in SipNose device (solid line and dashed line) and two commercial devices (star and open square) were examined. For the first SipNose experiment (solid line), the drug volume was 100 μl (total volume of 8.1 ml) and for the second SipNose experiment, (dashed line), the drug volume was 500 μl (total volume of 8.5). The first commercial device (star) was the Otrimer™ from Novartis; the second was the Simply Saline Nasal Mist from Church & Dwight Co., Inc. (http://www.armandhammer.com/SimplySaline.aspx). It can be seen that the time needed for the release of 8.1 and 8.5 ml of gas+substance was less than 300 ms even for the larger volume, and that the time was very much less than the 12 s (Otrimer™, star) and 20 s (Simply saline, square) needed for the commercial devices to release the volume of 8 ml.

In reference to FIG. 58, the effect of drug volume on the release time, the time for the drug and carrier gas to substantially completely exit the device is shown for the SipNose device (solid line and dashed line). Typically, the release time is affected by the activation time and reflects the time for the device to reconfigure from the ACTIVE configuration to the INACTIVE configuration or vice versa For the SipNose device, 8 ml of gas was used. For the first SipNose experiment (solid line), the pressure was 2 barg and for the second SipNose experiment, (dashed line), the pressure was 6 barg. It can be seen that the release time was less than 300 ms even for the larger volumes.

In reference to FIG. 59, the effect of gas volume on the release time is shown for the SipNose device (solid line and dashed line) and for two commercial device, the MAD Nasal from LMA (dot-dash line and dash-double dot line) and the Simply Saline Nasal Mist from Church & Dwight Co., Inc. (http://www.armandhammer.com/SimplySaline.aspx) (dotted line). For the SipNose device, pressures of 2 barg (diamonds) and 5 barg (triangles) were used, and drug volumes of 100 μl (solid line) and 500 μl (dashed line) were used. For the MAD Nasal device, drug volumes of 100 μl (dot-dash line) and 500 μl (dash-double dot line) were used and pressure was generated by manually compressing the devices. For the Simply Saline device, a pressure of 6 barg was used.

The release times were less than 300 ms for the SipNose device, even for the lower pressure and higher volume, significantly less than the 1.5 s to 20 s needed with the commercial devices.

In all of the SipNose experiments, over a range of pressures from 2 barg to 10 barg, a range of gas volumes from 2 ml to 12 ml and a range of drug volumes from 100 μl to 500 μl, significantly less than 0.5 s was needed to empty the SipNose device of drug plus gas. This is significantly less than the more than 1.5 s needed by even the fastest of the commercial devices.

In some embodiments, the release time is less than 1 s.

In some embodiments, it is less than 0.5 s.

In preferred embodiments, the release time is between 100 ms and 500 ms.

It should be emphasized that any embodiment of the present invention and any variant thereof can be used for both for humans (medical use) and animals. Thus, any of the devices as disclosed above and any variant thereof can be used for veterinary applications as well as (human) medical applications.

The pressure rate $\Delta P/\Delta t$ for a SipNose device with 0.8 mm orifice and a gas volume of 8 ml and for saline delivered by the Alrin™ nasal pump and the Simply Saline™ nasal pump is shown in Table 17. For the simply Saline™ nasal pump, there is no pre-defined release time. Release begins when an activation button is pressed and continues as long as the button remains depressed.

TABLE 17

Pressure Rate $\Delta P/\Delta t$

| | Drug Volume (ml) | Total Volume (ml) | Pressure Rate (barg/ms) |
|---|---|---|---|
| SipNose | 0.1 | 8.1 | −0.22 |
| SipNose | 0.5 | 8.5 | −0.045 |
| Saline, via Alrin ™ nasal pump | 0.1 | 0.1 | −5 × 10−4 |
| Simply Saline | same as total volume | dependent on release duration | −3 × 10−4 |

It is clear that the pressure rate for the SipNose device is on the order of 2 orders of magnitude greater than for the commercial devices.

The pressure as a function of time for pressures above 2 barg for a gas volume of 8 ml, a drug volume of 0.1 ml and an orifice diameter of 0.8 mm can be calculated from $$P=471 V_{sub}^{-1.5}$$

The pressure as a function of time for pressures above 2 barg for a gas volume of 8 ml, a drug volume of 0.5 ml and an orifice diameter of 0.8 mm can be calculated from $$P=8510 V_{sub}^{-1.5}$$

In general, for an orifice diameter of 0.8 mm and pressures above 2 barg, the pressure can be calculated from $$P=a_{p1} V_{sub}^{-bp1}$$

where $a_{p1}$ is in a range from 1 to 20,000 and $b_{p1}$ is in a range from 1 to 2.

The drug volume rate $\Delta V_{sub}/\Delta t$ is shown in Table 18. For the SipNose device, the orifice diameter was 0.8 mm orifice and the gas volume was 8 ml.

TABLE 18

Drug Volume Rate $\Delta V_{sub}/\Delta T$

| Pressure (barg) | Drug Volume Rate (ml/ms) |
|---|---|
| Drug volume less than 250 µl | |
| 2 | 0.97 |
| 6 | 2.54 |
| Drug volume more than 250 µl | |
| 2 | 5.95 |
| 6 | 10 |

The release time for a pressure of 2 barg, a gas volume of 8 ml and an orifice diameter of 0.8 mm can be calculated from $$T=37+\exp(2+0.018 V_{sub})$$

The release time for a pressure of 6 barg, a gas volume of 8 ml and an orifice diameter of 0.8 mm can be calculated from $$T=-2.9+2 \exp(2.86+0.025 V_{sub})$$

In general, for an orifice diameter of 0.8 mm, the release time if the drug volume only is varied can be calculated from $$T=a_{v1}+b_{v1} \exp(c_{v1}+d_{v1} V_{sub})$$

where $a_{v1}$ is in a range from −50 to 50, $b_{v1}$ is in a range from 0.1 to 5, $c_{v1}$ is in a range from 1 to 5 and $d_{v1}$ is in a range from 0.01 to 0.05.

The gas volume rate $\Delta V_{gas}/\Delta t$ is shown in Table 19. For the SipNose device, the orifice diameter was 0.8 mm. For the SipNose device, the pressure was 2 barg, while, for the MAD Nasal device, the device was pressed by hand; the delivery pressure was not measured.

TABLE 19

Gas Volume Rate $\Delta V_{gas}/\Delta T$

| Device | Pressure (barg) | Drug volume (µl) | Gas Volume Rate (ml/ms) |
|---|---|---|---|
| SipNose | 2 | 100 | 1.43 |
| SipNose | 2 | 500 | 0.367 |
| SipNose | 6 | 100 | 1.11 |
| SipNose | 6 | 500 | 0.182 |
| MAD Nasal | | 100 | 0.015 |
| MAD Nasal | | 500 | 0.0084 |
| Simply Saline | 6 | | 0.0004 |

The release time for the SipNose device, for a pressure P of 2 barg and a drug volume $V_{sub}$ of 100 µl can be calculated from $$T=-38+1.43 V_{gas}$$

The release time for the SipNose device for a pressure P of 2 barg and a drug volume $V_{sub}$ of 500 µl can be calculated from $$T=68.5-0.367 V_{gas}$$

The release time for the SipNose device, for a pressure P of 6 barg and a drug volume $V_{sub}$ of 100 µl can be calculated from $$T=-20+1.11 V_{gas}$$

The release time for the SipNose device, for a pressure P of 6 barg and a drug volume $V_{sub}$ of 500 µl can be calculated from $$T=-16+0.182 V_{gas}$$

In general, for an orifice diameter of 0.8 mm, the release time can be calculated from $$T=a_{v2}+b_{v2} V_{gas}$$

where $a_{v2}$ is in a range of −100 to 100 and $b_{v2}$ is in a range of −5 to 5.

EXAMPLE 18

Carrying distance and spread width area were compared for the SipNose device and two commercial devices, the Alrin and the Otrivin devices, by firing them at a target (9200) 50 cm from the tip of the nozzle (9100) of the device being fired. FIG. 60A-C shows the devices during firing.

For the SipNose device (FIG. 60A), the aerosol (9150) is visible for the majority of the distance between the nozzle (9100) and the target (9200) and the material deposited forms a distinct patch (9300) on the target (9200).

For the Alrin device (FIG. 60B) and the Otrivin device (FIG. 60C), the aerosol is virtually invisible, even near the tip or the nozzle (9100) and no evidence that any of the material has reached the target (9200).

EXAMPLE 19

For a distance between nozzle and target of 30 cm, dispensing 100 µl a liquid in a carrier volume, the penetration of the aerosol through 4 mm of a fabric medium was compared for different operating conditions for the SipNose device and three commercial devices, the Alrin, the MAD Nasal from Wolfe Tory and the Otrivin devices. In all cases, the aerosol from the SipNose device penetrated the 4 mm of fabric (FIG. 61A-E and Table 20).

TABLE 20

Spread on absorbing surface

| | | Diameter | | Area | | |
|---|---|---|---|---|---|---|
| | Pressure (barg) | Volume (ml) | Inner (cm) | Outer (cm) | Inner (cm$^2$) | Outer (cm$^2$) | Penetration? |
| SipNose | | | | | | | |
| 1 | 5.6 | 18 | 2.5 | 6 | 4.9 | 28.3 | YES |
| 2 | 4 | 8 | 2 | 6.5 | 3.1 | 33.2 | YES |
| 3 | 6 | 8 | 3 | 5 | 7.1 | 19.6 | YES |
| Commercial | | | | | | | |
| Alrin ™ nasal pump | — | — | — | 15 | — | 177 | NO |
| MAD Nasal | — | — | 8 | 12 | 50.2 | 113 | NO |
| Otrivin ™ nasal pump | — | — | — | 23 | — | 415 | NO |

FIG. 61A-C shows that, for the three typical operating conditions, significant amounts of the material penetrate through the 4 mm of fabric, consistent with what was seen for the nasal cast example (Example 14, FIG. 37).

FIG. 61A-C also shows the inner area (dashed circle) delineating the area of heavier deposition and the outer area (solid circle) delineating the area of lighter deposition. For the two commercial devices, the MAD Nasal from Wolfe Tory (FIG. 61D) and the Alrin (FIG. 61E), deposition is light across the entire area, and the edges of the deposition region are not well define

EXAMPLE 20

The diameter of the inner (more dense) area was measured for different operating conditions for the SipNose device, and the total diameter was measured for four commercial devices, the Otrivin device from Novartis, the Otrimer device from Novartis, the Alrin device from Teva and the MAD device from Wolfe Tory.

As shown in FIG. 62, the plume width is significantly smaller for the SipNose device for all operating conditions where the valve opening time was less than 500 msec Four tests were made with a valve that opened slowly (opening time>500 msec). In two cases, where the diameter of the open valve was small (0.22 mm), no aerosol was formed. In the other two cases (valve diameter 0.8 mm, open squares), the plume was wide (12 and 10 cm). This indicates that, in preferred embodiments, the valve opening time should be less than 500 msec and that, as long as the opening time is in this range, the plume with is both much narrower than that for the commercial devices and is better defined.

EXAMPLE 21

FIG. 63 compares the repeatability of the SipNose device to that of a typical commercial device, an Otrimer delivery device. In both cases, the devices were repeatedly activated, for a total of five activations. The pressure was measured before and after activation for both devices.

For the SipNose device, the pressure before activation was, within 1%, the same each time (6.13±0.02 bar) whereas, for the Otrimer delivery device, the pressure decreased each time the device was used; the pressure before the last activation was less than 60% of the initial pressure (first activation, 6.14 bar, last activation, 3.57 bar).

Furthermore, for the SipNose device, the pressure was completely discharged for each activation (pressure after=0 each time; ratio current/first=1). For the Otrimer delivery device, on the other hand, only a small fraction of the pressure was discharged. The pressure difference was less than 5% of the pressure before activation for the first activation and decreased with activation number, being less than 1% for the fifth activation.

Other types of delivery devices include pressurized metered dose inhalers (pMDIs), dry powder inhalers and nebulizers.

In a pMDI, the delivery pressure will necessarily decrease with activation number, as a portion of the fixed initial pressure is discharged on each activation. Dry powder inhalers tend to have poor repeatability because the patient inhales to deliver the medication, which is inherently poorly controllable. As demonstrated above, nasal sprays tend to have a fairly long "recovery time", decreasing repeatability for subsequent activations.

Nebulizers can have good repeatability. In a typical nebulizer, a gas at high pressure flows through the device, combines with an aerosol, and is then delivered to the patient. If a regulator is used to control the pressure of the gas flowing through the device, the repeatability of the nebulizer can be as good as the accuracy and reliability of the regulator.

The Respimat® Soft Mist inhaler from Boehringer Ingelheim is a carrier-free inhaler. It comprises a medicament cartridge with a stiff outer shell and a flexible inner bag which contains the medicament and a holder. The holder comprises a bottom part, into which the cartridge fits, which is rotatable relative to the upper part. Rotating the bottom part tensions a spring, which moves the cartridge downward toward the base of the device. This induces pressure in the region between the base and the cartridge and forces air through a hole in the base of the cartridge, compressing the flexible inner bag and causing the liquid medicament to rise through a capillary tube into a holding chamber.

Pressure on a triggering device releases the spring and activates the device. The released spring contracts back to its inactivated position, which pushes the cartridge and attached capillary tube upward into the holding chamber. A non-return valve prevents the medicament from returning to the flexible bag. The increased pressure on the medicament in the holding chamber forces the medicament through a nozzle, thereby atomizing it.

Unlike the SipNose device, the Respimat device is designed to produce a low-velocity, "soft" mist with a velocity of less than 30 cm/sec, compared to the velocities of over 10 m/sec for the SipNose device. For the Respimat device, a high-velocity mist is disadvantageous and is to be avoided.

In the Respimat device, the quality of the aerosol is controlled by the design of the nozzle, with the small particle size produced by a number of small openings in the nozzle.

EXAMPLE 22

A comparison was made of the efficacy of delivery of the anesthetic Midazolam, when used for pre-medication, between an embodiment of the SipNose device of the present invention and a prior-art device, the commercial nasal pump based on positive displacement (as the pump used for Alrin™ delivery) and the MAD Nasal from Wolfe Tory.

Comparison with nasal pump (using 5 mg/ml solution): For a pre-medication procedure with commercial nasal pump (positive displacement pump), in order to achieve the desired dose of 3 mg Midazolam, the delivery device was inserted into a nostril and an aliquot of Midazolam is delivered. The delivery device is then inserted into the opposite nostril and a second aliquot of Midazolam is delivered. This is repeated twice more with a 30 sec intervals between each cycle, for a total of six aliquots of Midazolam, three in each nostril. In oppose to that, for SipNose device delivery, a single dose of 0.6 ml was delivered to one nostril.

Comparison with MAD (using a 1 mg/ml solution): For a pre-medication procedure with MAD atomizer, in order to achieve the desired dose of 1.4 mg Midazolam, the delivery device was delivered to one nostril and an aliquot of Midazolam within a volume of 1.4 ml was delivered. For SipNose device delivery the Midazolam was delivered in 2 separate aliquots of 0.7 ml, one to each nostril.

In order to determine the efficacy of anesthetization a BIS EEG monitoring was used, where the BIS values for brain activity are calculated from the EEG activity. Awake, unsedated individuals typically have BIS values ≥97. Mildly sedated individuals typically have BIS values in the 80's, moderately sedated individuals typically have BIS values in the 70's, while fully sedated individuals typically have BIS values below about 70; BIS values between about 45 and about 60 are commonly used for general anesthesia during the maintenance phase of an operation.

Two comparisons were made between the commercial device and the present, SipNose, device. In the first, 3 mg of Midazolam was administered and the commercial device was a commercial nasal pump (positive displacement), in the second, 1.4 mg of Midazolam was administered and the commercial device was a MAD applicator.

As can be seen from Table 21, the SipNose device effectively sedated the patient in all 8 cases, while the commercial nasal pump was only effective for 3 out of 4 patients. In no case were there adverse events. The mean onset times are not significantly different for the SipNose device and the commercial device, since the range of variability is large.

The administration time was significantly shorter for the SipNose device, 1 sec vs. 1 min.

The rate of sedation was greater with the SipNose device, with a minimum BIS of 74.5±9 for the SipNose device compared to a minimum BIS of 87.5±5.3 for the commercial device.

TABLE 21

Comparison of SipNose and Commercial Nasal Pump in sedation with Midazolam

|  | SipNose | Commercial Nasal Pump |
|---|---|---|
| Number of Patients | 8 | 4 |
| Number of Positive Sedations | 8 | 3 |
| Mean onset time (min) | 5.9 ± 4.6 | 6.7 ± 4.6 |
| Adverse events | 0 | 0 |
| Time to administer (sec) | 1 | 60 |
| level of Maximum BIS | 97 | 97 |
| Level of minimum BIS | 74.5 ± 9 | 87.5 ± 5.3 |
| Minimum BIS excluding failure | — | 85 |

Figure 64:
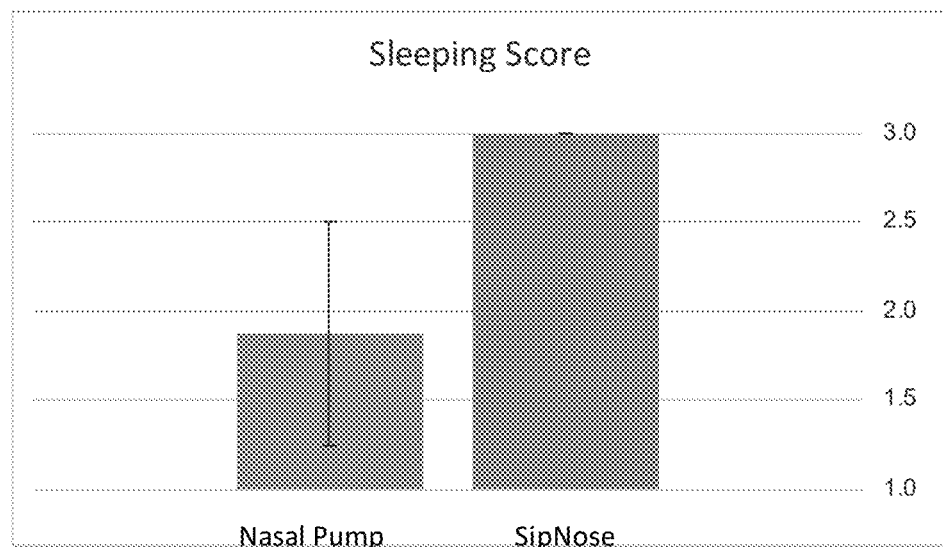

If sleep scores are taken for the patients, where a 1 means the patients was not sleepy, 2 means that the patient is sleepy or calm, and 3, that the patient is sleeping, the SipNose device (FIG. 64) achieved a score of 3, with all patients sleeping, whereas the score for the commercial device was less than 2.

In the second comparison, the total dose of Midazolam was 1.4 mg in a total volume of carrier of 1.4 ml. For the SipNose device, it was administered in two aliquots of 0.7 ml, whereas it was administered in one aliquot for the commercial MAD Nasal atomizer from Wolfe Tory. Midozolam was administered to four patients, two with the SipNose device and two with the commercial MAD device.

As shown in Table 22, sedation is better with the SipNose device; sedation failed entirely for Patient 2 with the commercial device. For this lower dose, the onset time was significantly shorter for the SipNose device (3 and 5 min vs. 20 and 8 min).

Even for this lower dose, where the SipNose administration was in two aliquots and the commercial device administration was in a single aliquot, administration time was lower for the SipNose device, with each aliquot administered in 1 sec, rather than the 7-10 sec for administration of a single aliquot with the commercial device.

TABLE 22

Comparison of SipNose and
Commercial Nasal Pump on sedation with Midazolam

|  | SipNose | | Commercial Nasal Pump | |
|---|---|---|---|---|
|  | Patient No. | | | |
|  | 1 | 2 | 1 | 2 |
| Positive Sedation | Yes | Yes | Limited | No |
| Onset time (min) | 5 | 3 | 20 | 8 |
| Adverse events | No | No | No | No |
| Time to administer (sec) | 2X1 | 2X1 | 10 | 7 |
| Level of minimum BIS | 84 | 84 | 83 | 92 |

In addition to the BIS values, a sleeping score was found by observation of the patients. The sleeping score was 3 for SipNose administration and averaged 1.5 for the commercial nasal pump.

As can be seen from this example, the SipNose device is at least as good as the commercial device in terms of efficacy and onset time for the delivery of the small molecule Midazolam, with onset time being no greater for the SipNose device than for the commercial device. The SipNose device appears to be more reliable in inducing anesthesia, with no failures in 10 patients compared to 2 failures and one partial failure in 6 patients with the commercial devices. Administration of a single aliquot is faster with the SipNose device, approximately 1 sec vs. approximately 10 sec for the commercial device.

In addition, larger does can be administered in a single aliquot with the SipNose device, reducing the number of aliquots needed for delivery of a total dose and thereby decreasing the chances of error in administration and the discomfort of the patient. The more rapid administration (1 sec vs. 7-10 sec or 1 min) will also reduce patient discomfort and reduce chances of error (e.g., releasing a patient before an aliquot is completely delivered).

EXAMPLE 23

In this example, epileptic seizures were induced in rats by administration of 47.5-50 mg/kg of Pentylenetetrazol (PTZ) for 5 min before the start of treatment with Midazolam. The Midazolam was administered either via IV or using a SipNose device, via the nasal passages. There were two dosing levels, 0.6 mg/kg (FIG. 65) and 6 mg/kg (FIG. 66).

In all cases, the Racine grading standard was used to determine the severity of the seizures. PZT was at t=−5 min; the start of treatment was at time t=0.

Treatment consisted of saline (control, diamonds), Midazolam administered by IV (triangles) or Midazolam administered nasally by a SipNose device (squares).

0.6 mg/kg

Figure 65:
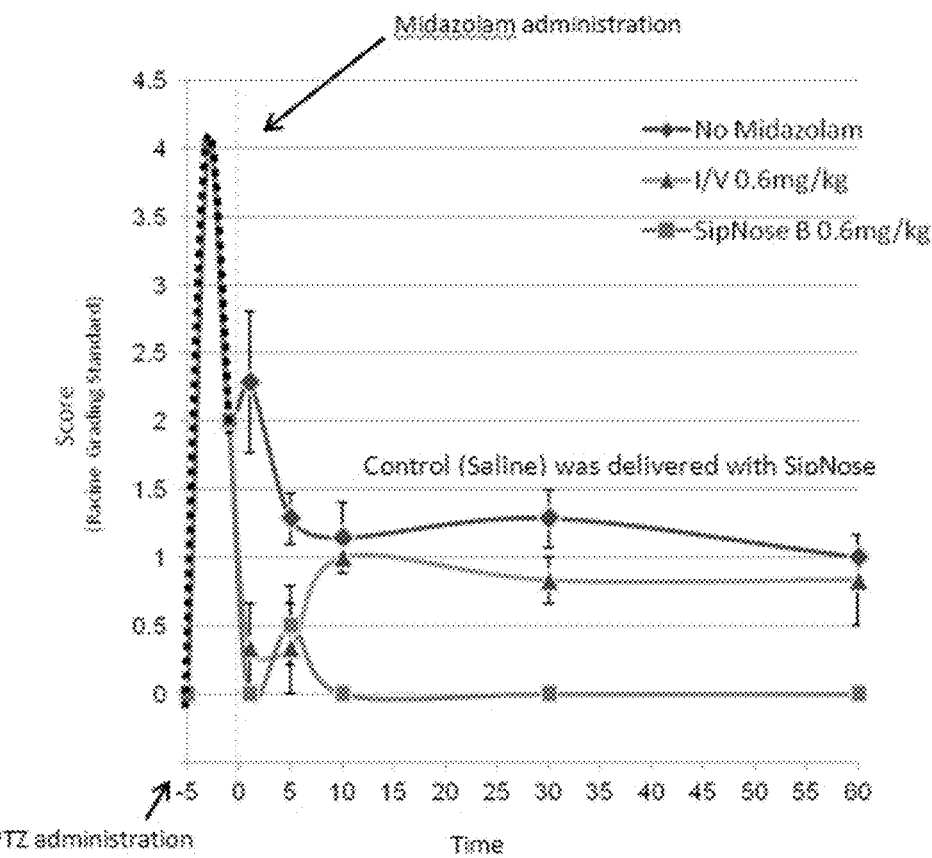
Figure 66:
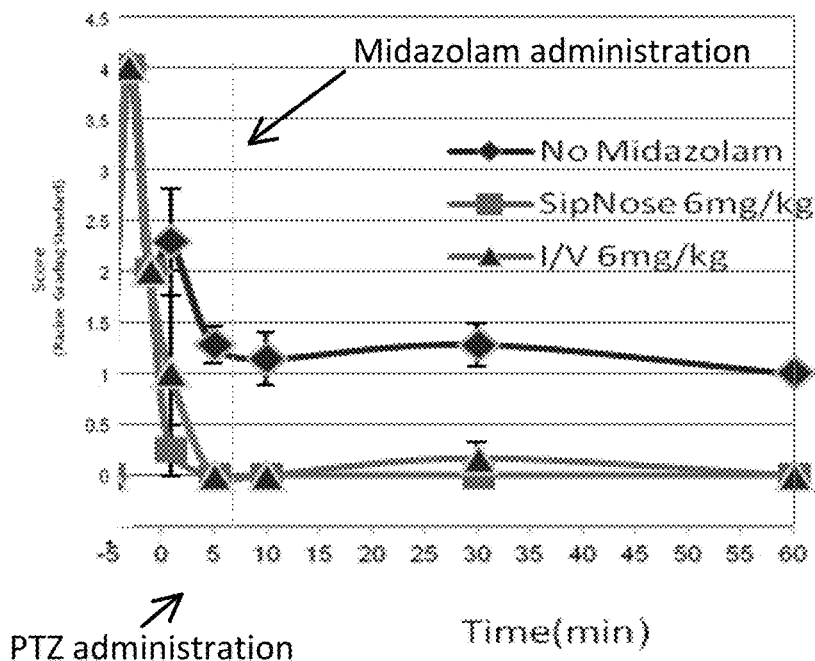

As can be seen in FIG. 65, the seizure severity rose from 0 to 4 by time t=0. After time t=0, seizure severity decreased. For saline administration, the Racine severity stabilized by about time t=5 min; it remained between about 1 and about 1.5 for the entire time between about t=10 min and about t=60 min. After IV administration of Midazolam, it remained between about 0.5 and about 1, whereas after SipNose administration, it was zero, no seizures were seen, for the entire time period between about time t=10 min and time t=60 min.

6 mg/kg

As can be seen in FIG. 66, the seizure severity rose from 0 to 4 by time t=0. After time t=0, seizure severity decreased. For saline administration, the Racine severity stabilized by about time t=5 min; it remained between about 1 and about 1.5 for the entire time between about t=10 min and about t=60 min.

For this larger dose, the IV and SipNose responses were more alike; both remained below a Racine severity of 0.5. no seizures were seen (Racine score 0) for the entire time period between about time t=10 min and time t=60 min.

EXAMPLE 24

In this example, doses of Midazolam between about 0.6 mg/kg and about 6 mg/kg were administered to rats and the concentration of Midazolam in the brain was measured 60 minutes after administration.

Figure 67:
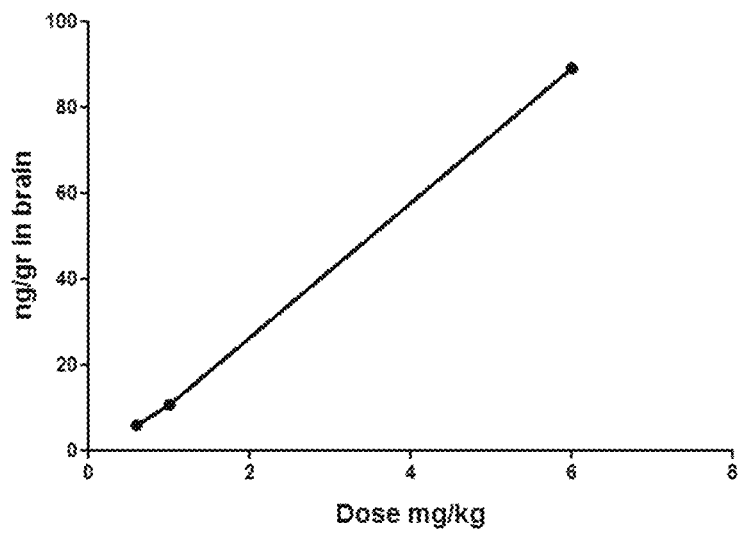

As shown in FIG. 67, for doses between about 0.6 mg/kg and about 6 mg/kg, the dose-response curve is essentially linear.

In other cases, the dose-response curve may not be linear, even if the amount reaching the target location (e.g., the brain) increases linearly with increasing dose, since, for some drugs, a subjects' dose-response curve will be non-linear (e.g., no response below a threshold, response independent of dose for doses above a threshold, etc.).

EXAMPLE 25

Figure 68:
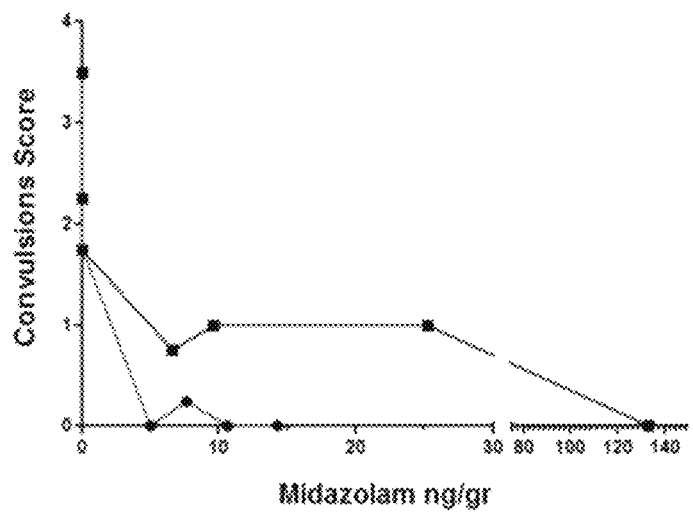

Epileptic seizures were induced in rats by administration of Pentylenetetrazol (PTZ) and the severity of the seizures was measured 60 minutes after administration of Mizadolam. Doses of Mizadolam varied from zero to 6 mg/kg with SipNose nasal delivery device and with an I/V administration. Brain concentrations of Midazolam were measured and a correlation between brain concentration and convulsions score is shown in FIG. 68. Brain concentrations varied from zero to 130 ng/gr brain tissue. Black squares represent the I/V administrated animals and black dots represent the SipNose administrated animals.

As can be seen from FIG. 68, the Racine severity (convulsion score) remained at about 1 until the IV administration of Mizadolam was about 25 ng/gm. The Racine severity then dropped slowly, not reaching zero until the IV administration of Mizadolam was about 130 ng/gm. In contrast, a SipNose concentration of Mizadolam of only about than 11 ng/gm was needed to completely prevent seizures (score=0).

As the examples disclosed hereinabove demonstrate, the SipNose device is stable with respect to minor changes in device parameters (e.g., pressure, volume, etc.); minor changes in device parameters do not significantly change the results.

EXAMPLE 26

Anti-Epileptic Treatment of Status Epilepticus (SE) in Human

Case study of a patient age of 39 years old, suffering from epileptic seizures (SE) was treated with a dose of 2 mg Midazolam with sipNose delivery device to deliver Midazolam via the nasal cavity.

Figure 69A:
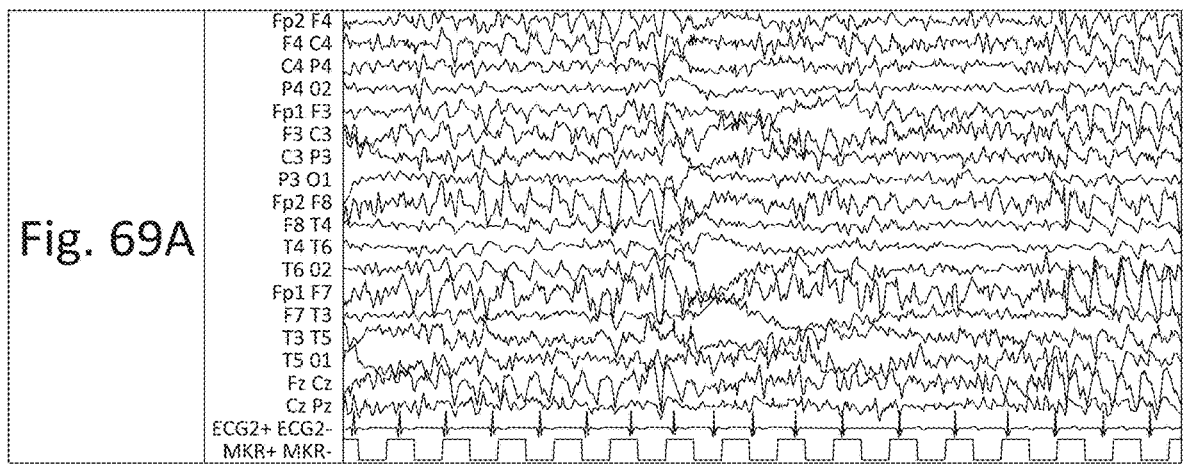
Figure 69B:
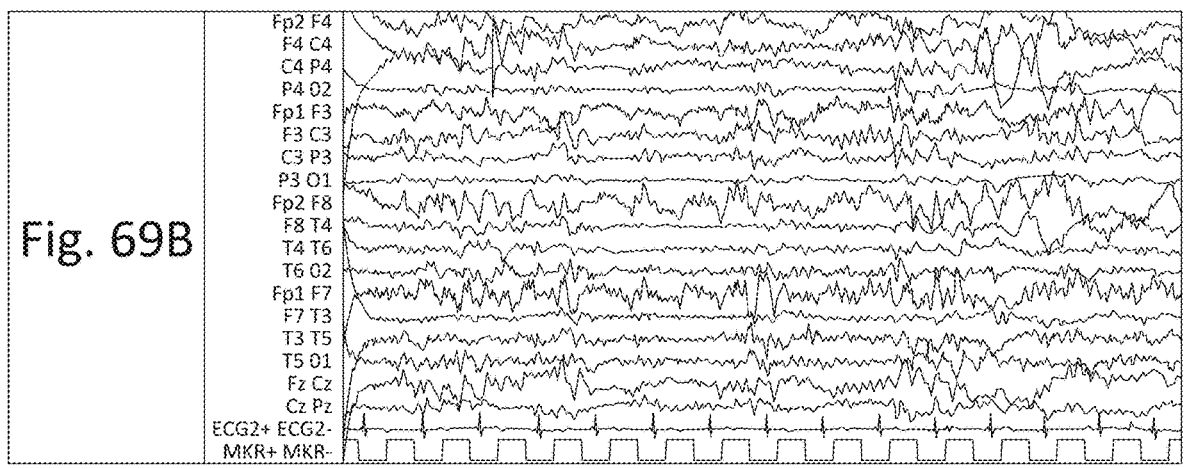

Administration of Midazolam was done by administrating of 1 ml of Midazolam to each nostril in a carrier volume of 1 ml. EEG recordings were measured before (FIGS. 69A and 69B) and 3 minutes following to the nasal administration of the drug with SipNose device. As can be seen from the recordings, brain signaling went back to normal with a short onset time following the administration of the drug.

Figure 70:
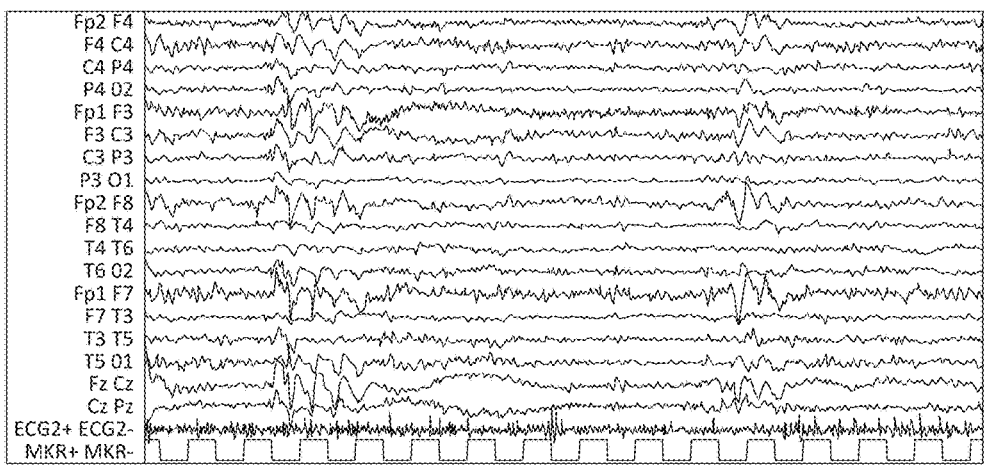

FIG. 70 illustrates the EEG recordings 3 minutes following to the nasal administration of the drug with SipNose device.

As can be seen, administration of the drug via the SipNose nasal delivery device results in reducing the repetitive un-normal brain activity during the seizures. Brain activity is back to normal 3 min following administration which reflects a fast onset and efficient delivery of the drug to its targets in the brain.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for delivering a predetermined volume $V_{sub}$ [ml] of at least one substance within at least one body cavity of a subject, said device comprising:
    at least one capsule sized and shaped for containing said predetermined volume $V_{sub}$ [ml] of said at least one substance; wherein said predetermined volume $V_{sub}$ [ml] is in a range of 0.01-7 ml;
    a nozzle configured for placement in proximity to said at least one body cavity, said nozzle being in fluid communication with said at least one capsule; said nozzle comprises at least one orifice, wherein a diameter D [mm] of the least one orifice is in a range of 0.2-6 mm;
    at least one valve mechanically connectable to said at least one capsule, characterized by at least two configurations: (i) an active configuration in which said at least one valve enables delivery of the predetermined volume $V_{sub}$ [ml] of said at least one substance from said at least one capsule to said at least one body cavity via said nozzle; and, (ii) an inactive configuration, in which said at least one valve prevents delivery of said predetermined volume $V_{sub}$ [ml] of said at least one substance from said at least one capsule to said at least one body cavity;
    said at least one valve is reconfigurable from said inactive configuration to said active configuration within a predetermined period of time, dT, in response to activation of said at least one valve; wherein said predetermined period of time dT is less than or equal to 200 ms; and
    a fluid tight chamber configured to contain predetermined volume $V_{gas}$ [ml] of pressurized gas at a predetermined pressure, $P_{gas}$ [barg]; wherein said predetermined volume $V_{gas}$ [ml] is in a range of 1-21 ml and said predetermined pressure $P_{gas}$ [barg] is in a range of 1-10 barg;
    said pressurized gas, once said at least one valve is reconfigured from said inactive configuration to said active configuration, is configured to entrain said at least one substance and deliver said at least one substance via said at least one orifice in said nozzle within said at least one body cavity;
    wherein said device is configured to deliver said predetermined volume $V_{sub}$ [ml] of said at least one substance and said predetermined volume $V_{gas}$ [ml] of said pressurized gas through said at least one orifice into said at least one body cavity, such that a release time of substantially the entirety of said predetermined volume $V_{sub}$ [ml] of said at least one substance and said predetermined volume $V_{gas}$ [ml] of said pressurized gas, $dT_{deliver}$, is less than 500 ms,
    wherein the $dT_{deliver}$ is maintained less than 500 milliseconds independent of the predetermined volume $V_{gas}$ [ml], the predetermined volume $V_{sub}$ [ml], and the predetermined pressure $P_{gas}$ [barg], and
    wherein a velocity of particles of the at least one substance, after exit from the device, is in a range of about 5 m/s to 50 m/s.

2. The device of claim 1, wherein at least one of the following is true:
    (a) said at least one body cavity is selected from a group consisting of a nasal cavity, a mouth, a throat, an ear, a vagina, a rectum, a urethra, and any combination thereof;
    (b) viscosity η of said at least one substance is in a range of $1\times10^{-3}$ poise to 1 poise;
    (c) DV50 diameter of particles of said at least one substance, after exit from said device, is less than 100 μm;
    (d) DV90 diameter of said particles of said at least one substance, after exit from said device, is less than 1000 μm;
    (e) said pressurized gas comprises air, nitrogen, oxygen, carbon dioxide, helium, neon, xenon and any combination thereof;
    (f) during dispensing of said at least one substance, a mixture of said predetermined volume $V_{gas}$ [ml] of said pressurized gas with said predetermined volume $V_{sub}$ [ml] of said at least one substance entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, which are determinable from characteristics of said device selected from a group consisting of: said predetermined volume of said pressurized gas, said predetermined volume of said at least one substance, said predetermined pressure of said pressurized gas, said diameter D [mm] of said at least one orifice, and any combination thereof;

(g) said at least one substance is selected from a group consisting of a gas, a liquid, a powder, an aerosol, a slurry, a gel, a suspension and any combination thereof;

(h) said at least one substance is stored under either an inert atmosphere or under vacuum to prevent reaction during storage;

(i) a dose-response curve is substantially linear for brain concentration of said at least one substance when administered nasally via said device; and (j) a dose-response curve for brain concentration having a fit selected from a group consisting of logarithmic, parabolic, exponential, sigmoid, power-low, and any combination thereof; of said at least one substance when administered nasally via said device.

3. The device of claim 1, wherein said at least one capsule has a main longitudinal axis, said at least one capsule comprising a number n of compartments, said at least one capsule configured to contain said predetermined volume $V_{sub}$ [ml] of said at least one substance, said predetermined volume $V_{sub}$ [ml] of said at least one substance containable in at least one of said n compartments; at least one of the following being true:
   (a) the number n of said compartments is an integer greater than or equal to 1; said compartments being annular; at least one of said compartments has cross-section with shape selected from a group consisting of: circular, oval, elliptical, polygonal and any combination thereof;
   (b) for said number n of compartments being an integer greater than 1, at least two said compartments have different volumes;
   (c) for said number n of compartments being an integer greater than 1, at least two said compartments have the same volume;
   (d) for said number n of compartments being an integer greater than 1, at least two said compartments have different cross-sectional areas;
   (e) for said number n of compartments being an integer greater than 1, at least two said compartments have the same cross-sectional area;
   (f) for said number n of compartments being an integer greater than 1, at least two said compartments contain different substances;
   (g) for said number n of compartments being an integer greater than 1, at least two said compartments contain the same substance;
   (h) for said number n of compartments being an integer greater than 1, at least two said compartments are disposed coaxially around said main longitudinal axis of said at least one capsule;
   (i) for said number n of compartments being an integer greater than 1, at least two said compartments are disposed sequentially along said main longitudinal axis of said at least one capsule;
   (j) for said number n of compartments greater than 1, there is mixing of said at least one substance in at least one of said n compartments with said at least one substance in at least one other of said n compartments during dispensing; and
   (k) for said number n of compartments greater than 1, there is reaction of said at least one substance in at least one of said n compartments with said at least one substance in at least one other of said n compartments during said dispensing.

4. The device of claim 1, wherein said at least one capsule comprises a port fluidly connectable to the exterior of said device, said port configured such that said at least one substance is insertable into said fluid-tight chamber via said port.

5. The device of claim 4, wherein said device comprises a port cover configured to provide an air-tight closure for said port, said port cover selected from a group consisting of slidable along said device, rotatable around said device, rotatable around a hinge on an exterior of said device and any combination thereof.

6. The device of claim 1, wherein, when said at least one substance is delivered into a tube, a distance travelled down the tube is L, at least one of the following being true:

(a) the distance L is substantially independent of said viscosity η of said at least one substance;
(b) the distance $L=a_{1a}P+b_{1a}$; the units of L are cm and the units of P are barg, $a_{1a}$ is in a range of 0 to 70 and $b_{1a}$ is in a range of 0 to 130;
(c) the distance L is substantially independent of said predetermined volume $V_{sub}$ [ml];
(d) the distance L, $L=a_{1b}P^3-b_{1b}P^2+c_{1b}P$; the units of L are cm and the units of P are barg, $a_{1b}$ is in a range of 2 to 6, $b_{1b}$ is in a range of 20 to 60 and $c_{1b}$ is in a range of 70 to 230;
(e) the distance $L=a_{1c}P^{b1c}$; the units of L are cm and the units of P are barg, a1c is in a range of 71 to 120 and b1c is in a range of 0.30 to 0.63;
(f) the distance $L=a_{2a}/(1+b_{2a}\exp(-c_{2a}D))$; the units of L are cm and the units of P are barg, $a_{2a}$ is in a range of 325 to 363, $b_{2a}$ is in a range of 47 to 163 and $c_{2a}$ is in a range of 7 to 15;
(g) the distance $L=a_{2b}D^2+b_{2b}D+c_{2b}$; the units of L are cm and the units of P are barg, $a_{2b}$ is in a range of 928 to 229, $b_{2b}$ is in a range of 600 to 1378 and $c_{2b}$ is in a range of 160 to 15;
(h) the distance $L=a_{3a}V_{sub}+b_{3a}$; the units of L are cm and the units of P are barg, $a_{3a}$ is in a range of 0.55 to 0.59 and $b_{3a}$ is in a range of 96 to 467;
(i) the distance $L=a_{5a}V_{gas}+b_{5a}$; the units of L are cm and the units of P are barg, $a_{5a}$ is in a range of 3.7 to 13.5 and $b_{5a}$ is in a range of 152 to 248;
(j) the $L=b_{5b}V_{gas}/(a_{5b}+V_{gas})$; the units of L are cm and the units of P are barg, $a_{5b}$ is in a range of 0.18 to 5.3 and $b_{5b}$ is in a range of 268 to 498; and
(k) the distance $L=a_{5c}V_{gas}^{b5c}$; the units of L are cm and the units of P are barg, $a_{5c}$ is in a range of 19 to 250 and $b_{5c}$ is in a range of 0.09 to 0.9.

7. The device of claim 1, wherein the nozzle comprises a nozzle tip portion and a tip extension that surrounds the nozzle tip portion and has a larger diameter than the nozzle tip portion,
   wherein the nozzle tip portion defines the at least one orifice through which the at least one substance exits longitudinally from the nozzle, wherein the tip extension defines at least one hole through which the at least one substance exits laterally from the nozzle.

8. The device of claim 1, wherein the $dT_{deliver}$ is maintained less than 500 milliseconds independent of how a user may operate the device.

9. The device of claim 1, wherein the velocity of the particles of the at least one substance, after the exit from the device, is maintained in the range of about 5 m/s to 50 m/s, independent of at least one of the predetermined volume $V_{gas}$ [ml] and the predetermined pressure $P_{gas}$ [barg].

10. The device of claim 1, wherein, during delivery of the at least one substance, a mixture of the predetermined volume $V_{gas}$ [ml] of the pressurized gas with the predetermined volume $V_{sub}$ [ml] of the at least one substance entrained within the predetermined volume $V_{gas}$ [ml] of the pressurized gas forms a plume of aerosol, wherein a full width of the plume of aerosol subtends an angle θ of less than 25°.

11. The device of claim 10, wherein the full width of the plume of aerosol is maintained at the angle θ of less than 25°, independent of at least one of the predetermined volume $V_{gas}$ [ml], the predetermined volume $V_{sub}$ [ml], and the predetermined pressure $P_{gas}$ [barg].

12. The device of claim 10, wherein the full width of the plume of aerosol, as measured at 6 cm from the nozzle, is 21 mm or less.

13. The device of claim 1, wherein said at least one valve is characterized by an internal diameter, through which said pressurized gas exits said fluid tight chamber and enters said nozzle, which is above 0.22 mm, such that said $dT_{deliver}$ is maintained less than 500 milliseconds independent of at least one of the predetermined volume $V_{gas}$ [ml], the predetermined volume $V_{sub}$ [ml], and the predetermined pressure $P_{gas}$ [barg].

14. A device for delivering a predetermined mass $M_{sub}$ [mg] of at least one substance within at least one body cavity of a subject, said device comprising:
   at least one capsule sized and shaped for containing said predetermined mass $M_{sub}$ [mg] of said at least one substance; wherein said predetermined mass $M_{sub}$ [mg] is in a range of 1-1000 mg;
   a nozzle configured for placement in proximity to said at least one body cavity, said nozzle being in fluid communication with said at least one capsule; said nozzle comprises at least one orifice, wherein a diameter D [mm] of the at least one orifice is in a range of 0.2-6 mm;
   at least one valve mechanically connectable to said at least one capsule, characterized by at least two configurations: (i) an active configuration in which said at least one valve enables delivery of said predetermined mass $M_{sub}$ [mg] of said at least one substance from said at least one capsule to said at least one body cavity via said nozzle; and, (ii) an inactive configuration, in which said at least one valve prevents delivery of said predetermined mass $M_{sub}$ [mg] of said at least one substance from said at least one capsule to said at least one body cavity,
   said at least one valve is reconfigurable from said inactive configuration to said active configuration within a predetermined period of time, dT, in response to activation of said at least one valve; wherein said predetermined period of time dT is less than or equal to 200 ms; and
   a fluid tight chamber configured to contain a predetermined volume $V_{gas}$ [ml] of pressurized gas at a predetermined pressure, $P_{gas}$ [barg]; wherein said predetermined volume $V_{gas}$ is in a range of 1-21 ml and said predetermined pressure $P_{gas}$ is in a range of 1-10 barg;
   said pressurized gas, once said at least one valve is reconfigured from said inactive configuration to said active configuration, is configured to entrain said at least one substance and deliver said at least one substance via said at least one orifice in said nozzle within said at least one body cavity;
   wherein said device is configured to deliver said predetermined mass $M_{sub}$ [mg] of said at least one substance and said predetermined volume $V_{gas}$ [ml] of said pressurized gas through said at least one orifice into said at least one body cavity, such that a release time of substantially the entirety of a predetermined volume $V_{sub}$ [ml] of said at least one substance and said predetermined volume $V_{gas}$ [ml] of said pressurized gas, $dT_{deliver}$, is less than 500 ms,
   wherein the $dT_{deliver}$ is maintained less than 500 milliseconds independent of the predetermined volume $V_{gas}$ [ml], the predetermined volume $V_{sub}$ [ml], and the predetermined pressure $P_{gas}$ [barg],
   wherein a velocity of particles of the at least one substance, after exit from the device, is in a range of about 5 m/s to 50 m/s.

15. The device of claim 14, wherein at least one of the following is true:
   (a) said at least one body cavity is selected from a group consisting of a nasal cavity, the mouth, the throat, an ear, a vagina, a rectum, a urethra, and any combination thereof;
   (b) viscosity η of said at least one substance is in a range of $1\times10^{-3}$ poise to 1 poise;
   (c) DV50 diameter of said particles of said at least one substance, after exit from said device, is less than 100 μm;
   (d) DV90 diameter of said particles of said at least one substance, after exit from said device, is less than 1000 μm;
   (e) said pressurized gas comprises air, nitrogen, oxygen, carbon dioxide, helium, neon, xenon and any combination thereof;
   (f) during dispensing of said at least one substance, a mixture of said predetermined volume $V_{gas}$ [ml] of said pressurized gas with said predetermined mass $M_{sub}$ [mg] of said at least one substance entrained within it forms a plume of aerosol, said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, which are determinable from characteristics of said device selected from a group consisting of: said predetermined volume of said pressurized gas, said predetermined volume of said at least one substance, said predetermined pressure of said pressurized gas, said diameter D [mm] of said at least one orifice, and any combination thereof;
   (g) a full width of the plume of aerosol comprising said at least one substance and said pressurized gas subtends an angle θ of less than 25°;
   (h) said at least one substance is selected from a group consisting of a gas, a liquid, a powder, an aerosol, a slurry, a gel, a suspension and any combination thereof;
   (i) said at least one substance is stored under either an inert atmosphere or under vacuum to prevent reactions during storage;
   (j) a dose-response curve is substantially linear for brain concentration of said at least one substance when administered nasally via said device; and
   (k) a dose-response curve for brain concentration having a fit selected from a group consisting of logarithmic, parabolic, exponential, sigmoid, power-low, and any combination thereof; of said at least one substance when administered nasally via said device.

16. The device of claim 14, wherein said at least one capsule has a main longitudinal axis, said at least one capsule comprising a number n of compartments, said at least one capsule configured to contain said predetermined mass $M_{sub}$ [mg] of said at least one substance, said predetermined mass $M_{sub}$ [mg] of said at least one substance containable in at least one of said n compartments; at least one of the following being true:
   (a) the number n of said compartments is an integer greater than or equal to 1; said compartments being annular; at least one of said compartments has cross-section with shape selected from a group consisting of: circular, oval, elliptical, polygonal and any combination thereof;

(b) for said number n of compartments being an integer greater than 1, at least two said compartments have different volumes;

(c) for said number n of compartments being an integer greater than 1, at least two said compartments have the same volume;

(d) for said number n of compartments being an integer greater than 1, at least two said compartments have different cross-sectional areas;

(e) for said number n of compartments being an integer greater than 1, at least two said compartments have the same cross-sectional area;

(f) for said number n of compartments being an integer greater than 1, at least two said compartments contain different substances;

(g) for said number n of compartments being an integer greater than 1, at least two said compartments contain the same substance;

(h) for said number n of compartments being an integer greater than 1, at least two said compartments are disposed coaxially around said main longitudinal axis of said at least one capsule;

(i) for said number n of compartments being an integer greater than 1, at least two said compartments are disposed sequentially along said main longitudinal axis of said at least one capsule;

(j) for said number n of compartments greater than 1, there is mixing of said at least one substance in at least one of said n compartments with said at least one substance in at least one other of said n compartments during dispensing; and (k) for said number n of compartments greater than 1, there is reaction of said at least one substance in at least one of said n compartments with said at least one substance in at least one other of said n compartments during said dispensing.

17. The device of claim 14, wherein said at least one capsule comprises a port fluidly connectable to the exterior of said device, said port configured such that a substance is insertable into said fluid-tight chamber via said port.

18. The device of claim 17, wherein said device comprises a port cover configured to provide an air-tight closure for said port, said port cover selected from a group consisting of slidable along said device, rotatable around said device, rotatable around a hinge on an exterior of said device and any combination thereof.

19. The device of claim 14, wherein, when said at least one substance is delivered into a tube, a distance travelled down the tube is L, at least one of the following being true:

(a) the distance L is substantially independent of said viscosity η of said at least one substance;

(b) the distance $L=a_{6a}P+b_{6a}$; the units of L are cm and the units of P are barg, $a_{6a}$ is in a range of 0 to 116 and $b_{6a}$ is in a range of 0 to 306;

(c) the distance $L=a_{6b}P^3-b_{6b}P^2+c_{6b}P$; the units of L are cm and the units of P are barg, $a_{6b}$ is in a range of 6.5 to 9.75, $b_{6b}$ is in a range of 65 to 97.5 and $c_{6b}$ is in a range of 202 to 303;

(d) the distance $L=a_{6c}P^{b6c}$; the units of L are cm and the units of P are barg, $a_{6c}$ is in a range of 0 to 902 and $b_{6c}$ is in a range of 0 to 3.72;

(e) the distance $L=a_{7a}V_{gas}{}^{b7a}$; the units of L are cm and the units of P are barg, $a_{7a}$ is in a range of 0 to 10 and $b_{7a}$ is in a range of 165 to 282;

(f) the distance $L=b_{7b}V_{gas}/(a_{7b}+V_{gas})$; the units of L are cm and the units of P are barg, $a_{7b}$ is in a range of 0.26 to 2.05 and $b_{7b}$ is in a range of 235 to 350; and (g) the distance $L=a_{7c}V_{gas}{}^{b7c}$; the units of L are cm and the units of P are barg, $a_{7c}$ is in a range of 0 to 320 and $b_{7c}$ is in a range of 0 to 0.96.

20. The device of claim 14, wherein said $dT_{deliver}$ is maintained less than 500 ms independent of how a user may operate the device.

21. The device of claim 14, wherein at least one of the following is being held true:

(a) a pressure rate $dP_{gas}/dT$ or $dP_{gas}/dT_{deliver}$ is greater than 0.001 barg/ms;

(b) a volume rate $dV_{sub}/dT$ or $dV_{sub}/dT_{deliver}$ is greater than 0.0001 ml/ms; and (c) a volume rate $dV_{gas}/dT$ or $dV_{gas}/dT_{deliver}$ is greater than 0.001 ml/ms.

22. A method of delivering a predetermined volume $V_{sub}$ [ml] of at least one substance within at least one body cavity of a subject, comprising:

providing a device comprising:

at least one capsule sized and shaped for containing said predetermined volume $V_{sub}$ [ml] of said at least one substance; wherein said predetermined volume $V_{sub}$ [ml] is in a range of 0.01-7 ml, a nozzle in fluid communication with said at least one capsule; said nozzle comprising at least one orifice, wherein a diameter D [mm] of the at least one orifice is in a range of 0.2-6 mm, at least one valve mechanically connected to said at least one capsule, characterized by at least two configurations: (i) an active configuration in which said at least one valve enables delivery of said predetermined volume $V_{sub}$ [ml] of said at least one substance from said at least one capsule to said at least one body cavity via said nozzle; and, (ii) an inactive configuration, in which said at least one valve prevents delivery of said predetermined volume $V_{sub}$ [ml] of said at least one substance from said at least one capsule to said at least one body cavity, said at least one valve is reconfigurable from said inactive configuration to said active configuration within a predetermined period of time, dT, in response to activation of said at least one valve; wherein said predetermined period of time dT is less than or equal to 200 ms, and a fluid tight chamber configured to contain predetermined volume $V_{gas}$ [ml] of pressurized gas at a predetermined pressure, $P_{gas}$ [barg]; wherein said predetermined volume $V_{gas}$ [ml] is in a range of 1-21 ml and said predetermined pressure $P_{gas}$ is in a range of 1-10 barg;

placing said nozzle in proximity to said at least one body cavity;

reconfiguring said at least one valve from said inactive configuration to said active configuration thereby entraining said at least one substance in said predetermined volume $V_{gas}$ [ml] of said pressurized gas; thereby delivering said predetermined volume $V_{sub}$ [ml] of said at least one substance and said predetermined volume $V_{gas}$ [ml] of said pressurized gas through said at least one orifice in (a) a pressure rate of $dP_{gas}/dT$, (b) a volume rate of $dV_{gas}/dT$; and (c) a volume rate of $dV_{sub}/dT$; wherein said predetermined volume $V_{gas}$ [ml] of said pressurized gas at said predetermined pressure $P_{gas}$ [barg] is released from said fluid-tight chamber upon activation of said at least one valve, said predetermined volume $V_{gas}$ [ml] of said pressurized gas entrains said at least one substance, erupts via said at least one orifice into said at least one body cavity, such that a release time of substantially the entirety of said predetermined volume $V_{sub}$ [ml] of said at least one substances and said predetermined volume $V_{gas}$ [ml] of said pressurized gas, $dT_{delver}$, is less than 500 ms, wherein the $dT_{delver}$ is maintained less than 500 milliseconds independent of the predetermined volume $V_{gas}$ [ml], the predetermined volume $V_{sub}$ [ml], and the predetermined pressure $P_{gas}$ [barg]; and characterizing a velocity of particles of the at least one substance, after exit from the device, as being in a range of about 5 m/s to 50 m/s.

23. The method of claim 22, additionally comprising at least one of the following steps:
  (a) selecting said at least one body cavity from a group consisting of: a nasal cavity, a mouth, a throat, an ear, a vagina, a rectum, a urethra, and any combination thereof;
  (b) selecting viscosity η of said at least one substance to be in a range of $1 \times 10^{-3}$ poise to 1 poise;
  (c) characterizing particles of said at least one substance, after exit from said device, by a DV50 diameter, said DV50 diameter being less than 150 μm;
  (d) characterizing said particles of said at least one substance, after exit from said device, by a DV90 diameter of less than 1000 μm;
  (e) selecting said gas from a group consisting of: air, nitrogen, oxygen, carbon dioxide, helium, neon, xenon and any combination thereof;
  (f) dispensing said at least one substance, and during said step of dispensing, forming a plume of aerosol with predetermined distribution from a mixture of said predetermined volume $V_{gas}$ [ml] of said pressurized gas and said predetermined volume $V_{sub}$ [ml] entrained within it; selecting said predetermined distribution from a group consisting of: a homogeneous distribution, and a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, which are determinable from characteristics of said device selected from a group consisting of: said predetermined volume of said pressurized gas, said predetermined volume of said at least one substance, said predetermined pressure of said pressurized gas, said diameter D [mm] of said at least one orifice, and any combination thereof;

(g) characterizing the plume of said aerosol by a plume angle θ, said plume angle θ subtending a full width of said plume, said plume angle θ subtending an angle of less than 25°;

(h) selecting said at least one substance from a group consisting of: a gas, a liquid, a powder, a slurry, a gel, a suspension, and any combination thereof;

(i) storing at least one said at least one substance under either an inert atmosphere or under vacuum, thereby preventing reactions during storage; and (j) characterizing a dose-response curve for brain concentration of said at least one substance to be of substantially linear form; and (k) a dose-response curve for brain concentration having a fit selected from a group consisting of logarithmic, parabolic, exponential, sigmoid, power-low, and any combination thereof; of said at least one substance when administered nasally via said device.

24. The method of claim 22, additionally comprising steps of providing said at least one capsule having a main longitudinal axis, said at least one capsule comprising a number n of compartments, configuring said at least one capsule to contain said predetermined volume $V_{sub}$ [ml] of said at least one substance, containing said predetermined volume $V_{sub}$ [ml] of said at least one substance in at least one of said n compartments; additionally comprising at least one of the following steps:

(a) providing said at least one capsule with n compartments; n is an integer greater than or equal to 1; said compartments being annular;

(b) selecting a cross-sectional shape of at least one of said n compartments from a group consisting of: circular, oval, elliptical, polygonal and any combination thereof;

(c) for said number n of compartments being an integer greater than 1, providing at least two of said plurality of said compartments having different volumes;

(d) for said number n of compartments being an integer greater than 1, providing at least two said compartments having the same volume;

(e) for said number n of compartments being an integer greater than 1, providing at least two said compartments having different cross-sectional areas;

(f) for said number n of compartments being an integer greater than 1, providing at least two said compartments having the same cross-sectional area;

(g) for said number n of compartments being an integer greater than 1, providing at least two of said compartments containing different substances;

(h) for said number n of compartments being an integer greater than 1, providing at least two of said compartments containing the same substance;

(i) for said number n of compartments being an integer greater than 1, disposing said plurality of compartments coaxially around said main longitudinal axis of said at least one capsule;

(j) for said number n of compartments being an integer greater than 1, disposing said plurality of compartments sequentially along said main longitudinal axis of said at least one capsule;

(k) for said number n of compartments being an integer greater than 1, mixing said at least one substance in at least one of said n compartments with said at least one substance in at least one other of said n compartments during dispensing; and (l) for said number n of compartments being an integer greater than 1, reacting said at least one substance in at least one of said n compartments with said at least one substance in at least one other of said n compartments during said dispensing.

25. The method of claim 22, additionally comprising step of inserting said predetermined volume $V_{sub}$ [ml] of said at least one substance into said at least one capsule via a port fluidly connectable to the exterior of said device.

26. The method of claim 25, additionally comprising step of providing an air-tight closure for said port, and of moving said port cover relative to said device in at least one motion selected from a group consisting of: sliding said port cover along said device, rotating said port cover around said device, rotating said port cover around a hinge on the exterior of said device and any combination thereof.

27. The method of claim 22, additionally comprising steps of delivering said at least one substance into a tube and measuring a distance L said at least one substance travels down the tube; and additionally comprising at least one of the following steps:

(a) selecting said viscosity η such that the distance L is substantially independent of viscosity η of said at least one substance;

(b) selecting said predetermined volume $V_{sub}$ [ml] such that the distance L is substantially independent of said predetermined volume $V_{sub}$ [ml];

(c) the distance $L=a_{1a}P+b_{1a}$ and selecting $a_{1a}$ to be in a range of 0 to 70 and $b_{1a}$ to be in a range of 0 to 130; where the units of L are cm and the units of P are barg;

(d) the distance $L=a_{1b}P^3-b_{1b}P^2+c_{1b}P$ and selecting $a_{1b}$ to be in a range of 2 to 6, $b_{1b}$ to be in a range of 20 to 60 and $c_{1b}$ to be in a range of 70 to 230; where the units of L are cm and the units of P are barg;

(e) the distance $L=a_{1c}P^{b1c}$ and selecting air to be in a range of 71 to 120 and $b_{1c}$ to be in a range of 0.30 to 0.63; where the units of L are cm and the units of P are barg;

(f) the distance $L=a_{2a}/(1+b_{2a}\exp(-c_{2a}D))$ and selecting $a_{2a}$ to be in a range of 325 to 363, $b_{2a}$ to be in a range of 47 to 163 and $c_{2a}$ to be in a range of 7 to 15; where the units of L are cm and the units of P are barg;

(g) the distance $L=a_{2b}D^2+b_{2b}D+c_{2b}$ and selecting am to be in a range of 928 to 229, $b_{2b}$ to be in a range of 600 to 1378 and cab to be in a range of 160 to 15; where the units of L are cm and the units of P are barg;

(h) the distance $L=a_{3a}V_{sub}+b_{3a}$ and selecting $a_{3a}$ to be in a range of 0.55 to 0.59 and $b_{3a}$ to be in a range of 96 to 467; where the units of L are cm and the units of P are barg;

(i) the distance $L=a_{5a}V_{gas}b_{5a}$ and selecting $a_{5a}$ to be in a range of 3.7 to 13.5 and $b_{5a}$ to be in a range of 152 to 248; where the units of L are cm and the units of P are barg;

(j) the distance $L=b_{5b}V_{gas}/(a_{5b}+V_{gas})$ and selecting $a_{5b}$ to be in a range of 0.18 to 5.3 and $b_{5b}$ to be in a range of 268 to 498; and (k) the distance $L=a_{5c}V_{gas}^{b5c}$ and selecting $a_{5c}$ to be in a range of 19 to 250 and $b_{5c}$ to be in a range of 0.09 to 0.9; where the units of L are cm and the units of P are barg.

28. The method of claim 22, additionally comprising step of either pre-pressurizing said fluid-tight chamber with said gas to said predetermined pressure; or pressurizing said fluid-tight chamber with said gas to said predetermined pressure before reconfiguring said valve from said inactive configuration to said active configuration.

29. The method of claim 22, further comprising storing the at least one substance within the at least one capsule prior to being dispensed, wherein the at least one substance is dispensed during activation.

30. The method of claim 22, wherein said $dT_{deliver}$ is maintained less than 500 ms independent of how a user may operate the device.

31. The method of claim 22, wherein at least one of the following is being held true:

(a) said pressure rate $dP_{gas}/dT$ or a pressure rate $dP_{gas}/dT_{deliver}$ is greater than 0.001 barg/ms;

(b) said volume rate $dV_{sub}/dT$ or a volume rate $dV_{sub}/dT_{deliver}$ is greater than 0.0001 ml/ms; and (c) said volume rate $dV_{gas}/dT$ or a volume rate $dV_{gas}/dT_{deliver}$ is greater than 0.001 ml/ms.

32. A method of delivering a predetermined mass $M_{sub}$ [mg] of at least one substance within at least one body cavity of a subject, comprising:

providing a device comprising:

at least one capsule sized and shaped for containing said predetermined mass $M_{sub}$ [mg] of said at least one substance; wherein said predetermined mass $M_{sub}$ [mg] is in a range of 1-1000 mg, a nozzle in fluid communication with said at least one capsule; said nozzle comprising at least one orifice, wherein a diameter D [mm] of the at least one orifice is in a range of 0.2-6 mm, at least one valve mechanically connected to said at least one capsule, characterized by at least two configurations: (i) an active configuration in which said at least one valve enables delivery of said predetermined mass $M_{sub}$ [mg] of said at least one substance from said at least one capsule to said at least one body cavity via said nozzle; and, (ii) an inactive configuration, in which said at least one valve prevents delivery of said predetermined mass $M_{sub}$ [mg] of said at least one substance from said at least one capsule to said at least one body cavity, said at least one valve is reconfigurable from said inactive configuration to said active configuration, within a predetermined period of time, dT, in response to activation of said at least one valve; wherein said predetermined period of time dT is less than or equal to 200 ms, and a fluid tight chamber adapted to contain predetermined volume $V_{gas}$ [ml] of pressurized gas at a predetermined pressure, $P_{gas}$ [barg]; wherein said predetermined volume $V_{gas}$ [ml] is in a range of 1-21 ml and said predetermined pressure $P_{gas}$ is in a range of 1-10 barg;

placing said nozzle in proximity to said at least one body cavity;

reconfiguring said at least one valve from said inactive configuration to said active configuration thereby entraining said at least one substance in said predetermined volume $V_{gas}$ [ml] of said pressurized gas; thereby delivering said predetermined mass $M_{sub}$ [mg] of said at least one substance and said predetermined volume $V_{gas}$ [ml] of said pressurized gas through said at least one orifice in (a) a pressure rate of $dP_{gas}/dT$, (b) a volume rate of $dV_{gas}/dT$; and (c) a volume rate of $dV_{sub}/dT$; wherein said predetermined volume $V_{gas}$ [ml] of said pressurized gas at said predetermined pressure $P_{gas}$ [barg] is released from said fluid-tight chamber upon activation of said at least one valve, said predetermined volume $V_{gas}$ [ml] of said pressurized gas entrains said at least one substance, erupts via said at least one orifice into said at least one body cavity, such that a release time of substantially the entirety of a predetermined volume $V_{sub}$ [ml] of said at least one substances and said predetermined volume $V_{gas}$ [ml] of said pressurized gas, $dT_{deliver}$, is less than 500 ms, wherein the $dT_{deliver}$ is maintained less than 500 milliseconds independent of the predetermined volume $V_{gas}$ [ml], the predetermined volume $V_{sub}$ [ml], and the predetermined pressure $P_{gas}$ [barg]; and characterizing a velocity of particles of the at least one substance, after exit from the device, as being in a range of about 5 m/s to 50 m/s.

33. The method of claim 32, additionally comprising at least one of the following:
(a) selecting said at least one body cavity from a group consisting of a nasal cavity, a mouth, a throat, an ear, a vagina, a rectum, a urethra, and any combination thereof;
(b) selecting viscosity η of said at least one substance to be in a range of $1 \times 10^{-3}$ poise to 1 poise;
(c) characterizing particles of said at least one substance, after exit from said device, by a DV50 diameter, said DV50 diameter being less than 100 μm;
(c) characterizing said particles of said at least one substance, after exit from said device, by a DV90 diameter of less than 1000 μm;
(e) selecting said gas from a group consisting of: air, nitrogen, oxygen, carbon dioxide, helium, neon, xenon and any combination thereof;
(f) dispensing said at least one substance, and during said step of dispensing, forming a plume of aerosol with predetermined distribution from a mixture of said predetermined volume $V_{gas}$ [ml] of said pressurized gas and said predetermined mass $M_{sub}$ [mg] entrained within it; selecting said predetermined distribution from a group consisting of: a homogeneous distribution, a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, which are determinable from characteristics of said device selected from a group consisting of: said predetermined volume of said pressurized gas, said predetermined volume of said at least one substance, said predetermined pressure of said pressurized gas, said diameter D [mm] of said at least one orifice, and any combination thereof;
(g) characterizing said plume of said aerosol by a plume angle θ, said plume angle θ subtending a full width of said plume, said plume angle θ subtending an angle of less than 25°;
(h) selecting said at least one substance from a group consisting of: a gas, a liquid, a powder, a slurry, a gel, a suspension, and any combination thereof;
(i) storing at least one said at least one substance under either an inert atmosphere or under vacuum, thereby preventing reactions during storage;
(j) characterizing a dose-response curve for brain concentration of said at least one substance to be of substantially linear form; and
(k) a dose-response curve for brain concentration having a fit selected from a group consisting of logarithmic, parabolic, exponential, sigmoid, power-low, and any combination thereof; of said at least one substance when administered nasally via said device.

34. The method of claim 32, additionally comprising step of either pre-pressurizing said fluid-tight chamber with said gas to said predetermined pressure; or pressurizing said fluid-tight chamber with said gas to said predetermined pressure before reconfiguring said valve from said inactive configuration to said active configuration.

35. The method of claim 32, further comprising storing the at least one substance within the at least one capsule prior to being dispensed, wherein the at least one substance is dispensed during activation.

36. The method of claim 32, wherein said $dT_{deliver}$ is maintained less than 500 ms independent of how a user may operate the device.

37. The method of claim 32, wherein at least one of the following is being held true:
(a) said pressure rate $dP_{gas}/dT$ or a pressure rate $dP_{gas}/dT_{deliver}$ is greater than 0.001 barg/ms;
(b) a mass rate $dM_{sub}/dT$ or $dM_{sub}/dT_{deliver}$ is greater than 0.0001 ml/ms; and
(c) said volume rate $dV_{gas}/dT$ or a volume rate $dV_{gas}/dT_{deliver}$ is greater than 0.001 ml/ms.

38. A device for delivering a predetermined volume $V_{sub}$ [ml] of at least one substance within at least one body cavity of a subject, said device comprising:
at least one capsule sized and shaped for containing said predetermined volume $V_{sub}$ [ml] of said at least one substance, wherein said predetermined volume $V_{sub}$ [ml] is in a range of 0.01-7 ml;
a nozzle configured for placement in proximity to said at least one body cavity, said nozzle being in fluid communication with said at least one capsule, said nozzle comprising at least one orifice, wherein a diameter D [mm] of the least one orifice is in a range of 0.2-6 mm;
at least one valve mechanically connectable to said at least one capsule, characterized by at least two configurations: (i) an active configuration in which said at least one valve enables delivery of the predetermined volume $V_{sub}$ [ml] of said at least one substance from said at least one capsule to said at least one body cavity via said nozzle; and (ii) an inactive configuration, in which said at least one valve prevents delivery of said predetermined volume $V_{sub}$ [ml] of said at least one substance from said at least one capsule to said at least one body cavity, said at least one valve being reconfigurable from said inactive configuration to said active configuration within a predetermined period of time, dT, in response to activation of said at least one valve, wherein said predetermined period of time dT is less than or equal to 200 ms; and
a fluid tight chamber configured to contain predetermined volume $V_{gas}$ [ml] of pressurized gas at a predetermined pressure, $P_{gas}$ [barg], wherein said predetermined volume $V_{gas}$ [ml] is in a range of 1-21 ml and said predetermined pressure $P_{gas}$ [barg] is in a range of 1-10 barg;
said pressurized gas, once said at least one valve is reconfigured from said inactive configuration to said active configuration, is configured to entrain said at least one substance and deliver said at least one substance via said at least one orifice in said nozzle within said at least one body cavity,
wherein said device is configured to deliver said predetermined volume $V_{sub}$ [ml] of said at least one substance and said predetermined volume $V_{gas}$ [ml] of said pressurized gas through said at least one orifice into said at least one body cavity, such that a release time of substantially the entirety of said predetermined volume $V_{sub}$ [ml] of said at least one substance and said predetermined volume $V_{gas}$ [ml] of said pressurized gas, $dT_{delivery}$, is less than 500 ms, and
wherein said at least one valve is characterized by an internal diameter, through which said pressurized gas exits said fluid tight chamber and enters said nozzle, which is above 0.22 mm, such that said dTdelivery is maintained less than 500 milliseconds independent of at least one of the predetermined volume Vgas [ml], the predetermined volume Vsub [ml], and the predetermined pressure Pgas [barg].

\* \* \* \* \*